United States Patent
Enquist et al.

(10) Patent No.: US 12,162,896 B2
(45) Date of Patent: Dec. 10, 2024

(54) SALTS AND POLYMORPHS OF CERTAIN MCL-1 INHIBITORS

(71) Applicant: Gilead Sciences, Inc., Foster City, CA (US)

(72) Inventors: John Enquist, San Mateo, CA (US); Michael A. Ischay, San Mateo, CA (US); Olga V. Lapina, Newark, CA (US); David W. Lin, Berkeley, CA (US); Christopher S. Regens, San Francisco, CA (US); David A. Siler, San Mateo, CA (US); Eric A. Standley, Foster City, CA (US); Sarah E. Wortman, Sacramento, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 18/311,708

(22) Filed: May 3, 2023

(65) Prior Publication Data

US 2023/0357274 A1 Nov. 9, 2023

Related U.S. Application Data

(60) Provisional application No. 63/338,119, filed on May 4, 2022.

(51) Int. Cl.
C07D 513/10 (2006.01)
A61P 35/00 (2006.01)
C07D 513/08 (2006.01)

(52) U.S. Cl.
CPC ............ C07D 513/10 (2013.01); A61P 35/00 (2018.01); C07D 513/08 (2013.01); C07B 2200/13 (2013.01)

(58) Field of Classification Search
CPC ............... C07D 513/10; C07D 513/08; C07B 2200/13; A61P 35/00
See application file for complete search history.

(56) References Cited

U.S. PATENT DOCUMENTS

| | | | | |
|---|---|---|---|---|
| 10,703,733 B2* | 7/2020 | Chu | ............... | A61P 35/00 |
| 10,988,451 B2* | 4/2021 | Chu | ............... | C07D 413/12 |
| 11,643,400 B2* | 5/2023 | Chu | ............... | C07D 267/20 |
| | | | | 540/543 |
| 2023/0312602 A1 | 10/2023 | Morrison et al. | | |

FOREIGN PATENT DOCUMENTS

| | | | |
|---|---|---|---|
| WO | WO-2019222112 A1 * | 11/2019 | ........... A61K 31/553 |
| WO | WO-2021/096860 A1 | 5/2021 | |
| WO | WO-2021/108254 A1 | 6/2021 | |
| WO | WO-2022/108984 A1 | 5/2022 | |
| WO | WO-2023/150249 A1 | 8/2023 | |
| WO | WO-2023/150250 A1 | 8/2023 | |
| WO | WO-2023/196360 A1 | 10/2023 | |
| WO | WO-2023/196361 A1 | 10/2023 | |

OTHER PUBLICATIONS

Guo et. al. (Aug. 2021), Pharmaceutical cocrystals: A review of preparations, physicochemical properties and applications, Acta Pharmaceutica Sinica B, 11, 2537-2564 (Year: 2021).*
ChemDraw Professional Version 20.0 (Year: 2024).*
Cue et. al. (Nov. 10, 2009), Green Process chemistry in the pharmaceutical industry, Green Chemistry Letters and Reviews, 2, 193-211 (Year: 2009).*
Liang, C. M. (2007) "Screening Polymorphic Forms of Drug Substances by Using Generalized Crystallization Techniques", Master's Thesis, National Taipei University of Technology, 149 pages. (English Abstract Only).
Intl. Search Report—Written Opinion dated Aug. 4, 2023 for Intl. Appl. No. PCT/US2023/020873.
Office Action dated Jan. 3, 2024 for Taiwanese Appl. No. 112116367.

* cited by examiner

*Primary Examiner* — Kortney L. Klinkel
*Assistant Examiner* — Dawanna Shar-Day White

(57) ABSTRACT

The present disclosure relates salts and the crystalline forms of certain 3',4,4',5-tetrahydro-2H,2'H-spiro[benzo[b][1,4] oxazepine-3,1'-naphthalene] derivatives as well as pharmaceutical formulations and therapeutic uses thereof. The present disclosure also relates to preparing such salts, crystalline forms and pharmaceutical formulations.

6 Claims, 58 Drawing Sheets

SALTS AND POLYMORPHS OF CERTAIN MCL-1 INHIBITORS

CROSS-REFERENCE TO RELATED APPLICATIONS

This application claims the benefit of priority of U.S. Provisional Application No. 63/338,119, filed May 4, 2022, the contents of which are incorporated herein by reference in its entirety for all purposes.

FIELD

The present disclosure relates salts and the crystalline forms of certain 3',4,4',5-tetrahydro-2H,2'H-spiro[benzo[b][1,4]oxazepine-3,1'-naphthalene] derivatives as well as pharmaceutical formulations and therapeutic uses thereof. The present disclosure also relates to preparing such salts, crystalline forms and pharmaceutical formulations.

BACKGROUND

Apoptosis (programmed cell death) is a process for eliminating unwanted or potentially dangerous cells from an organism. Avoidance of apoptosis is critical for the development and sustained growth of tumors. Myeloid cell leukemia 1 protein (MCL-1) is an anti-apoptotic member of the Bcl-2 family of proteins. MCL-1 is necessary to sustain the growth of diverse tumors, including acute myeloid leukemia (AML), MYC- or BCR-ABL-driven pre-B/B lymphomas and certain breast cancers. See, e.g., "Discovery of S64315, a Potent and Selective Mcl-1 Inhibitor" by Z. Szlavik, *J. Med. Chem.*, 2020, 63(22):13762-13795.

Research has shown that MCL-1 inhibitors can be used to treat a variety of cancers. See, e.g., "The MCL1 inhibitor S63845 is tolerable and effective in diverse cancer models" by A. Kotschy et al., *Nature*, 2016(538): 477-482; "Structure Based Design of Non-Natural Peptidic Macrocyclic Mcl-1 Inhibitors" by J. Johannes et al., *ACS Med. Chem. Lett.*, 2017, 8(2):239-244 & *ACS Med. Chem. Lett.*, 2017, 8(11): 1204; "Synergistic action of the MCL-1 inhibitor S63845 with current therapies in preclinical models of triple-negative and HER2-amplified breast cancer" by D. Merino et al., *Sci. Transl. Med.*, 2017 Aug. 2, 9(401): eaam7049; "Discovery of Mcl-1-specific inhibitor AZD5991 and preclinical activity in multiple myeloma and acute myeloid leukemia" by A. Tron et al., *Nature Comm.* 2018(9): Article No. 5341; "AMG 176, a Selective MCL1 Inhibitor, Is Effective in Hematologic Cancer Models Alone and in Combination with Established Therapies" by S. Caenepeel et al., Cancer Discov., 2018 Dec. 8(12):1582-1597; "Discovery of S64315, a Potent and Selective Mcl-1 Inhibitor" by Z. Szlavik at al., J. Med. Chem., 2020, 63(22):13762-13795.

WO 2019/222112 discloses novel 3',4,4',5-tetrahydro-2H,2'H-spiro[benzo[b][1,4]oxazepine-3,1'-naphthalene] derivatives that are active against MCL-1. For example, Compound 1 (below) has been shown to be an effective MCL-1 inhibitor.

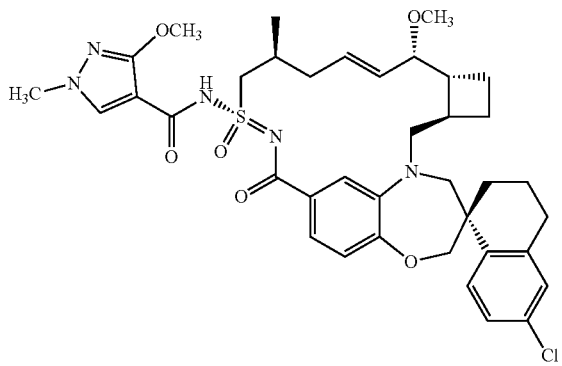

Compound 1

While WO 2019/222112 provides a synthesis of Compound 1, the synthesis therein provides an amorphous free base product. Amorphous products tend to be less stable than their crystalline counterparts, which can create problems for manufacturing and stability of pharmaceutical formulations. Thus, a need exists to develop more stable forms of Compound 1.

SUMMARY

In certain embodiments, the present disclosure relates to a crystalline form of Compound 1:

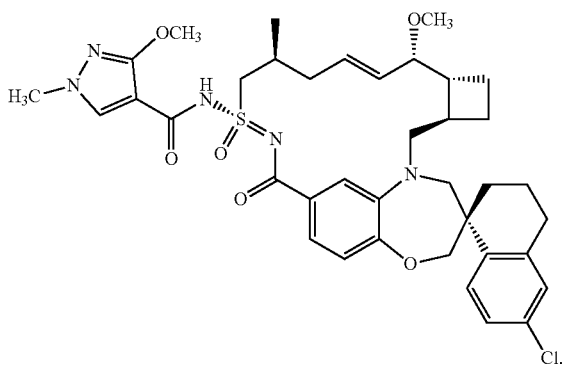

Compound 1

In certain embodiments, the present disclosure relates to crystalline Form I of Compound 1. In certain embodiments, the present disclosure relates to crystalline Form II of Compound 1. In certain embodiments, the present disclosure relates to crystalline Form III of Compound 1. In certain embodiments, the present disclosure relates to crystalline Form IV of Compound 1.

In certain embodiments, the present disclosure relates to a crystalline form of a pharmaceutically acceptable salt of Compound 1:

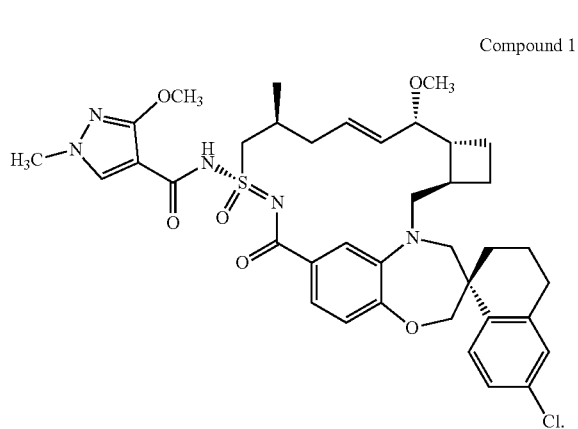 [SMILES: COc1nn(C)cc1C(=O)N[S@@]1(=O)=NC(=O)c2ccc3c(c2)N(C[C@@H]2CC[C@H]2[C@@H](OC)/C=C/C[C@H](C)C1)C[C@@]1(CCCc2cc(Cl)ccc21)CO3]

Compound 1

In certain embodiments, the present disclosure relates to a crystalline form of a sodium salt of Compound 1. In certain embodiments, the present disclosure relates to crystalline Form 1 of a sodium salt of Compound 1. In certain embodiments, the present disclosure relates to crystalline Form 2 of a sodium salt of Compound 1. In certain embodiments, the present disclosure relates to crystalline Form 3 of a sodium salt of Compound 1. In certain embodiments, the present disclosure relates to crystalline Form 4 of a sodium salt of Compound 1. In certain embodiments, the present disclosure relates to crystalline Form 5 of a sodium salt of Compound 1.

In certain embodiments, the present disclosure relates to a crystalline form of a potassium salt of Compound 1. In certain embodiments, the present disclosure relates to crystalline Form 1 of a potassium salt of Compound 1.

In certain embodiments, the present disclosure relates to a crystalline form of a diethylamine salt of Compound 1. In certain embodiments, the present disclosure relates to crystalline Form 1 of a diethylamine salt of Compound 1.

In certain embodiments, the present disclosure relates to a crystalline form of a choline salt of Compound 1. In certain embodiments, the present disclosure relates to crystalline Form 1 of a choline salt of Compound 1.

In certain embodiments, the present disclosure relates to a pharmaceutical composition comprising a crystalline form of Compound 1 or a crystalline form of a pharmaceutically acceptable salt of Compound 1 and a pharmaceutically acceptable carrier or excipient.

In certain embodiments, the present disclosure relates to a method for inhibiting MCL-1 in a patient comprising administering to the patient a crystalline form of Compound 1, a crystalline form of a pharmaceutically acceptable salt of Compound 1, or a pharmaceutical composition comprising a crystalline form of Compound 1 or a crystalline form of a pharmaceutically acceptable salt of Compound 1 and a pharmaceutically acceptable carrier or excipient.

In certain embodiments, the present disclosure relates to a method for treating cancer in a patient comprising administering to the patient a crystalline form of Compound 1 according, a crystalline form of a pharmaceutically acceptable salt of Compound 1, or the pharmaceutical composition comprising a crystalline form of Compound 1 or a crystalline form of a pharmaceutically acceptable salt of Compound 1 and a pharmaceutically acceptable carrier or excipient.

In certain embodiments, the present disclosure relates to a use of a crystalline form of Compound 1, a crystalline form of a pharmaceutically acceptable salt of Compound 1, or the pharmaceutical composition comprising a crystalline form of Compound 1 or a crystalline form of a pharmaceutically acceptable salt of Compound 1 and a pharmaceutically acceptable carrier or excipient for treating cancer.

In certain embodiments, the present disclosure relates to a use of a crystalline form of Compound 1, a crystalline form of a pharmaceutically acceptable salt of Compound 1, or the pharmaceutical composition comprising a crystalline form of Compound 1 or a crystalline form of a pharmaceutically acceptable salt of Compound 1 and a pharmaceutically acceptable carrier or excipient for the manufacture of a medicament for treating cancer.

In certain embodiments, the present disclosure relates to a crystalline form of Compound 1, a crystalline form of a pharmaceutically acceptable salt of Compound 1, or a pharmaceutical composition comprising a crystalline form of Compound 1 or a crystalline form of a pharmaceutically acceptable salt of Compound 1 and a pharmaceutically acceptable carrier or excipient for use in a method of treating cancer.

Additional objects and advantages will be set forth in part in the description which follows, and in part will be understood from the description, or may be learned by practice. The objects and advantages will be realized and attained by means of the elements and combinations particularly pointed out in the appended claims.

It is to be understood that both the foregoing summary and the following detailed description are exemplary and explanatory only and are not restrictive of the claims. The headings used throughout this disclosure are provided for convenience only and are not to be construed to limit the claims in any way.

The accompanying drawings, which are incorporated in and constitute a part of this specification, illustrate several embodiments and together with the description, serve to explain the principles described herein.

DESCRIPTION OF THE EMBODIMENTS

I. Definitions

Figure 1:
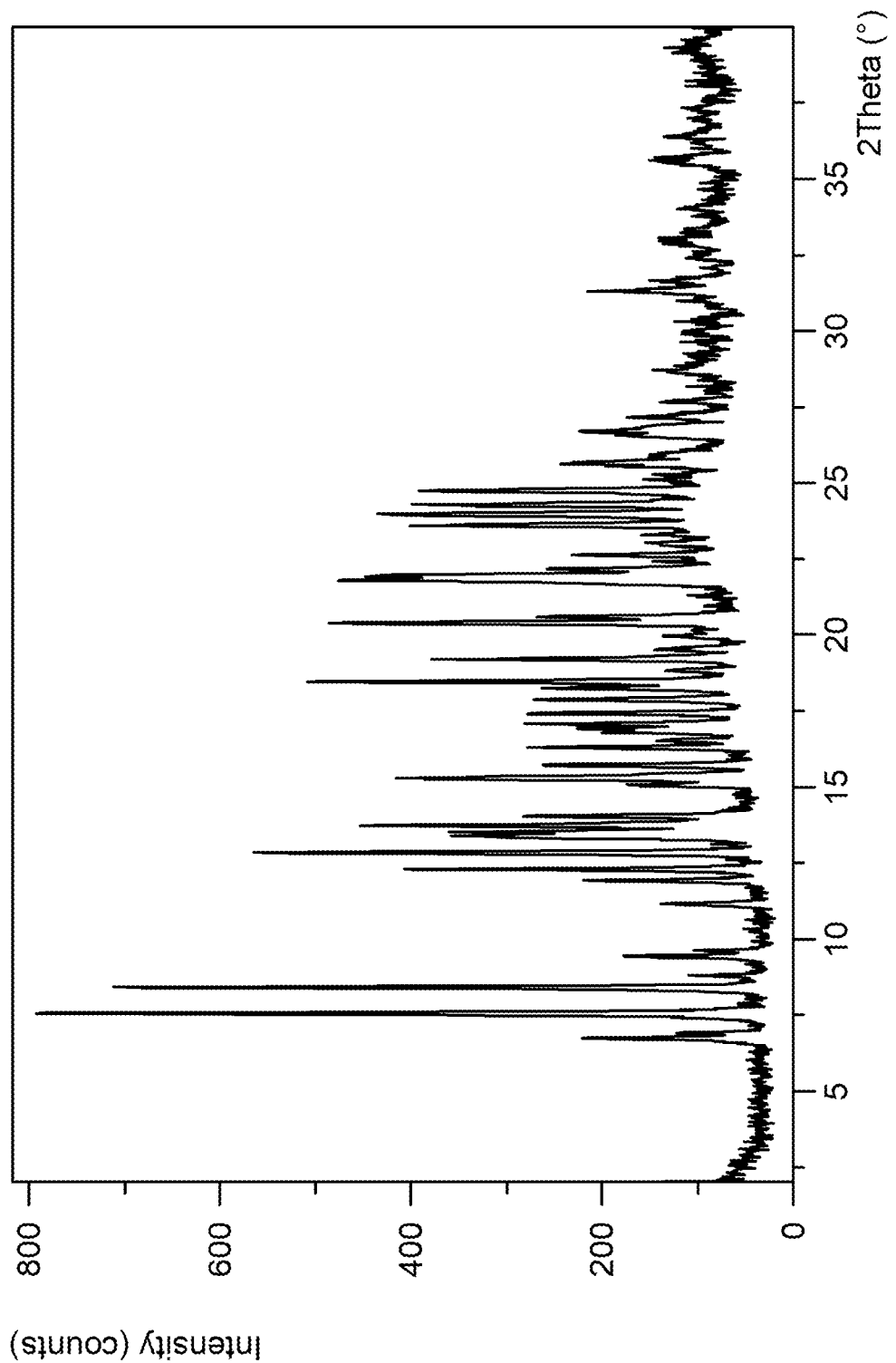
FIG. 1 provides an XRPD pattern for Na Salt Form 1.

Unless the context requires otherwise, throughout the present specification and claims, the word "comprise" and variations thereof, such as "comprises" and "comprising," are to be construed in an open, inclusive sense, that is as "including, but not limited to".

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

It should be understood that the salts and polymorphs of Compound 1 encompass all isotopically-labeled compounds, which have one or more atoms replaced by an atom having a different atomic mass or mass number. Examples of isotopes that can be incorporated into the disclosed compounds include isotopes of hydrogen, carbon, nitrogen, oxygen, sulfur and chlorine, such as $^{2}H$, $^{3}H$, $^{11}C$, $^{13}C$, $^{14}C$, $^{13}N$, $^{15}N$, $^{15}O$, $^{17}O$, $^{18}O$, $^{35}S$, and $^{36}Cl$. These radiolabeled compounds could be useful to help determine or measure the effectiveness of the compounds, by characterizing, for example, the site or mode of action, or binding affinity to pharmacologically important site of action. Certain isotopically-labeled compounds, for example, those incorporating a radioactive isotope, may be useful in drug and/or substrate tissue distribution studies. The radioactive isotopes tritium, i.e. $^{3}H$, and carbon-14, i.e. $^{14}C$, may be particularly useful for this purpose in view of their ease of incorporation and ready means of detection.

Substitution with heavier isotopes such as deuterium, i.e. $^{2}H$, may afford certain therapeutic advantages resulting from greater metabolic stability. For example, in vivo half-life may increase or dosage requirements may be reduced. Thus, heavier isotopes may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds can generally be prepared by conventional techniques known to those skilled in the art or by processes analogous to those described in the Examples as set out below using an appropriate isotopically-labeled reagent in place of the non-labeled reagent previously employed.

The terms "crystalline" or "crystal" refer to a form of matter in which the atoms, molecules, or ions are arranged in a highly ordered three-dimensional lattice.

The term "substantially as shown in" when referring, for example, to an XRPD pattern, a DSC thermogram, or a TGA graph includes a pattern, thermogram or graph that is not necessarily identical to those depicted herein, but that falls within the limits of experimental error or deviations when considered by one of ordinary skill in the art.

"Stable compound" and "stable structure" are meant to indicate a compound that is sufficiently robust to survive isolation to a useful degree of purity from a reaction mixture, and/or formulation into an efficacious therapeutic agent.

"Optional" or "optionally" means that the subsequently described event or circumstances may or may not occur, and that the description includes instances where said event or circumstance occurs and instances in which it does not.

The phrase "pharmaceutically acceptable carrier or excipient" includes, without limitation, any additive that is acceptable for use in humans or animals. Such additives include, for example, any and all types of adjuvants, carriers, glidants, sweetening agents, diluents, preservatives, dye/colorants, flavor enhancers, surfactants, wetting agents, dispersing agents, suspending agents, stabilizers, isotonic agents, solvents, or emulsifiers.

A "pharmaceutical composition" refers to a formulation of a compound for the delivery to an animal, e.g., humans.

"Effective amount" or "therapeutically effective amount" refers to an amount of a compound, which when administered to a patient in need thereof, is sufficient to effect treatment for a disease, condition, and/or disorder. Such an amount would be sufficient to elicit a biological or medical response of a tissue system or patient. An "effective amount" or "therapeutically effective amount" will vary depending on such factors as the compound and its biological activity, the composition used for administration, the time of administration, the route of administration, the rate of excretion of the compound, the duration of the treatment, the type of disease, condition, and/or disorder being treated and its severity, drugs used in combination with or coincidentally with the compounds of the invention, and the age, body weight, general health, sex and diet of the patient. The "effective amount" or "therapeutically effective amount" can be determined routinely by one of ordinary skill in the art having regard to their own knowledge, the state of the art, and this disclosure.

The terms "inhibit" and "inhibiting" as used herein refer to blocking a particular biological pathway. In some embodiments, the term "inhibiting" refers to the administration of a compound or composition to block MCL-1 activity.

The terms "treatment" and "treating" as used herein refer to the administration of a compound or composition to try to cure or heal a disease, condition, and/or disorder in a patient, or to alleviate or eliminate symptoms of such diseases, conditions and/or disorders.

Prevention" or "preventing" means any treatment of a disease, condition, and/or disorder that causes the clinical symptoms of the disease, condition and/or disorder not to develop.

The terms "subject" or "patient" refer to an animal, such as a mammal (including a human). The methods and uses described herein may be useful in human therapy and/or veterinary applications. In some embodiments, the subject is a mammal (or the patient). In some embodiments, the subject (or the patient) is human, domestic animals (e.g., dogs and cats), farm animals (e.g., cattle, horses, sheep, goats and pigs), and/or laboratory animals (e.g., mice, rats, hamsters, guinea pigs, pigs, rabbits, dogs, and monkeys). In one embodiment, the subject (or the patient) is a human. "Human (or patient) in need thereof" refers to a human (or patient) who may have or is suspect to have a disease, condition, and/or disorder that would benefit from certain treatment.

A "tautomer" refers to a proton shift from one atom of a molecule to another atom of the same molecule. The salts and crystalline forms of Compound 1 include tautomers of any said compounds.

As used herein, the term "about" refers to a numeric value, including, for example, whole numbers, fractions, and percentages, whether or not explicitly indicated. The term "about" generally refers to a range of numerical values (e.g., +/−5-10% of the recited range) that one of ordinary skill in the art would consider equivalent to the recited value (e.g., having the same function or result). When terms such as "about" precede a list of numerical values or ranges, the terms modify all of the values or ranges provided in the list. In some instances, the term "about" may include numerical values that are rounded to the nearest significant figure.

Also, the singular forms "a" and "the" include plural references unless the context clearly dictates otherwise. Thus, e.g., reference to "the compound" may refer to a plurality of such compounds.

"Pharmaceutically acceptable" or "physiologically acceptable" refer to compounds, salts, compositions, dosage forms and other materials which are acceptable for use in humans or animals.

"Unit dosage forms" are physically discrete units suitable as unitary dosages for subjects (e.g., human subjects and other mammals), each unit containing a predetermined quantity of active material calculated to produce a desired therapeutic effect.

Abbreviations

| | |
|---|---|
| ° | Degree |
| ° C. | Degree Celsius |
| ° K | Degree Kelvin |
| α | Angle Between Lattice Parameters |
| β | Angle Between Lattice Parameters |
| γ | Angle Between Lattice Parameters |
| Å | Angstrom |
| 2-MeTHF or | 2-Methyltetrahydrofuran |
| a | Lattice Parameter of Unit Cell |
| ACN or MeCN | Acetonitrile |
| API | Active Pharmaceutical Ingredient |
| Aq | Aqueous |
| $a_w$ | Water activity |
| b | Lattice Parameter of Unit Cell |
| BSA | Benzenesulfonic Acid |
| c | Lattice Parameter of Unit Cell |
| CF | Co-Former |
| Conc. HCl | Concentrated Hydrochloric Acid (~37%) |
| Conv. | Conversion |
| d | Diameter |
| DCM | Dichloromethane |
| DMAc | N,N-Dimethylacetamide |
| DSC | Differential Scanning Calorimetry |
| DVS | Dynamic Vapor Sorption |
| eq. or equiv | Equivalent |
| EtOAc | Ethyl Acetate |
| EtOH | Ethanol |
| $H_2O$ | Water |
| HCl | Hydrochloric Acid |
| Hept | n-Heptane or Heptanes |
| IPA | Isopropanol |
| IPAc | Isopropyl Acetate |
| IPC | In-Process Control |
| IR | Infrared |
| KF | Karl Fisher Titration |
| M | Molar |
| MeOH | Methanol |
| MEK | Methyl Ethyl Ketone |
| MIBK | Methyl Isobutyl Ketone |
| ML | Mother Liquor |
| MSA | Methanesulfonic Acid |

| | |
|---|---|
| MTBE | Methyl tert-Butyl Ether |
| MW | Molecular Weight |
| n/a | Not Analyzed or Not Applicable |
| NMR | Nuclear Magnetic Resonance |
| NMT | Not More Than |
| p-TSA | p-Toluenesulfonic Acid |
| PLM | Polarized Light Microscopy |
| ppm | Parts Per Million |
| PSD | Particle Size Distribution |
| RH | Relative Humidity |
| rxn | Reaction |
| soln. | Solution |
| TGA | Thermogravimetric Analysis |
| TGA-MS or | Thermogravimetric Analysis-Mass |
| THF | Tetrahydrofuran |
| V | Volume of Unit Cell |
| V or Vols | Volumes (L/kg limiting reagent) |
| VT-XRPD | Variable temperature X-ray powder |
| wt | Weight |
| wt % | Weight percent |
| XRPD or XRD | X-Ray Powder Diffraction |

II. Compounds

One aspect of the present disclosure relates to a crystalline form of Compound 1:

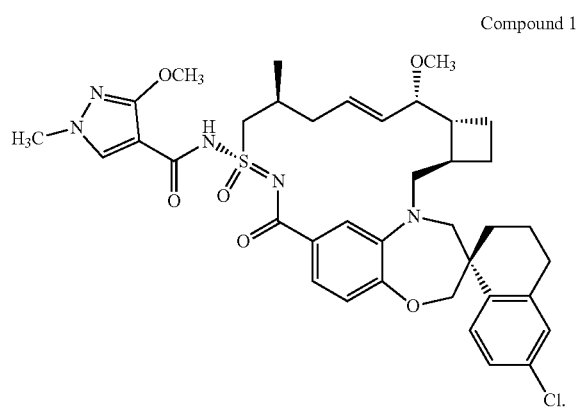 [SMILES: COc1nn(C)cc1C(=O)N[S@@]1(=O)=NC(=O)c2ccc3c(c2)N(C[C@@H]2CC[C@H]2[C@@H](OC)/C=C/C[C@H](C)C1)C[C@@]1(CCCc2cc(Cl)ccc21)CO3]

Compound 1

Another aspect of the present disclosure relates to a crystalline form of a solvate of Compound 1.

One aspect of the present disclosure relates to a pharmaceutically acceptable salt of Compound 1:

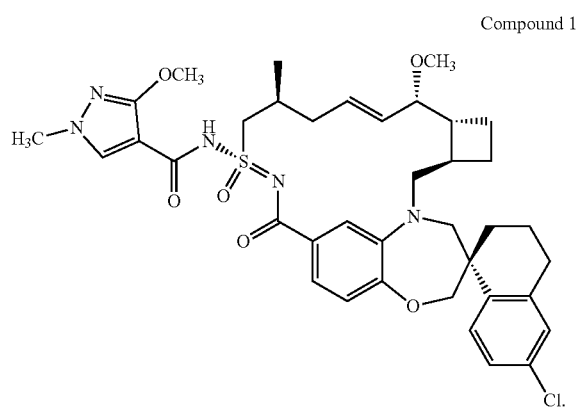 [SMILES: COc1nn(C)cc1C(=O)N[S@@]1(=O)=NC(=O)c2ccc3c(c2)N(C[C@@H]2CC[C@H]2[C@@H](OC)/C=C/C[C@H](C)C1)C[C@@]1(CCCc2cc(Cl)ccc21)CO3]

Compound 1

Another aspect of the present disclosure relates to a solvate of a pharmaceutically acceptable salt of Compound 1.

One aspect of the present disclosure relates to a crystalline form of a pharmaceutically acceptable salt of Compound 1:

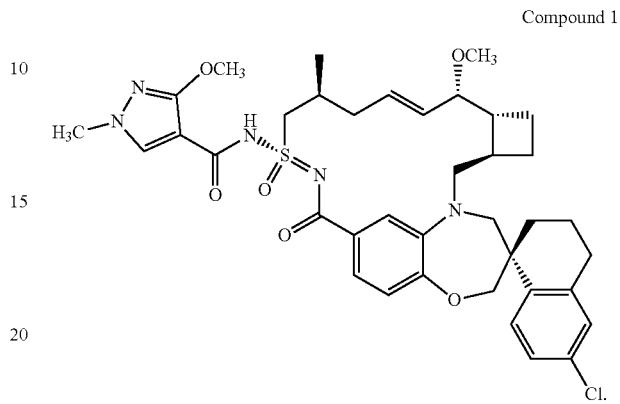

Compound 1

Another aspect of the present disclosure relates to a crystalline form of a solvate of a pharmaceutically acceptable salt of Compound 1.

A. Crystalline Forms of Compound 1

One aspect of the present disclosure relates to a crystalline form of Compound 1:

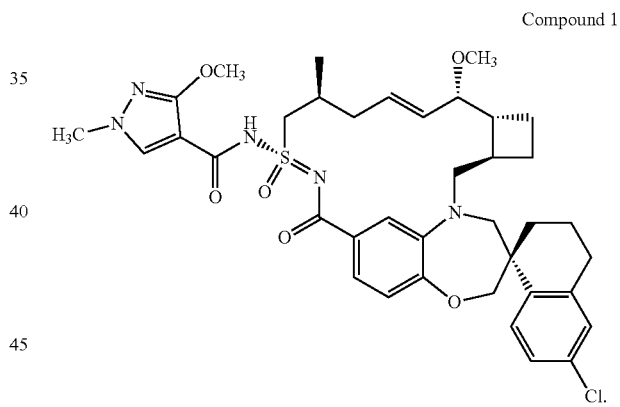

Compound 1

In some embodiments, the crystalline form is Form I. In some embodiments, the crystalline form is Form II. In some embodiments, the crystalline form is Form III. In some embodiments, the crystalline form is Form IV.

In some embodiments, the crystalline form of Compound 1 is characterized by an x-ray powder diffraction pattern comprising peaks at about 4.9°±0.2°, 8.6°±0.2° and 14.3°±0.2° 2-θ. In some embodiments, the x-ray powder diffraction pattern comprises one or more additional peaks chosen from peaks at about 16.2°±0.2°, 18.3°±0.2° and 22.1°±0.2° 2-θ. In some embodiments, the x-ray powder diffraction pattern comprises one or more additional peaks chosen from peaks at about 17.8°±0.2°, 19.3°±0.2° and 21.5°±0.2° 2-θ. In some embodiments, the x-ray powder diffraction pattern comprises one or more additional peaks chosen from peaks at about 13.5°±0.2°, 14.6°±0.2°, 16.0°±0.2°, 17.5°±0.2°, 18.8°±0.2°, 20.2°±0.2°, 20.7°±0.2°, 23.0°±0.2°, 24.6°±0.2°, 26.3°±0.2° and 26.8°±0.2° 2-θ. In some embodiments, the crystalline form is characterized by an x-ray powder diffraction pattern that is substantially as set forth in FIG. 31.

In some embodiments, the crystalline form of Compound 1 is Form I. In some embodiments, Form I is characterized by having a differential scanning calorimetry thermogram comprising an endothermic peak with onset at about 180° C. In some embodiments, the differential scanning calorimetry thermogram is substantially as set forth in FIG. 32.

In some embodiments, Form I is characterized by having a thermogravimetric analysis thermogram showing a weight loss of about 1.0% over a temperature of from ambient temperature to about 170° C. In some embodiments, the thermogravimetric analysis thermogram is substantially as set forth in FIG. 33.

Figure 34:
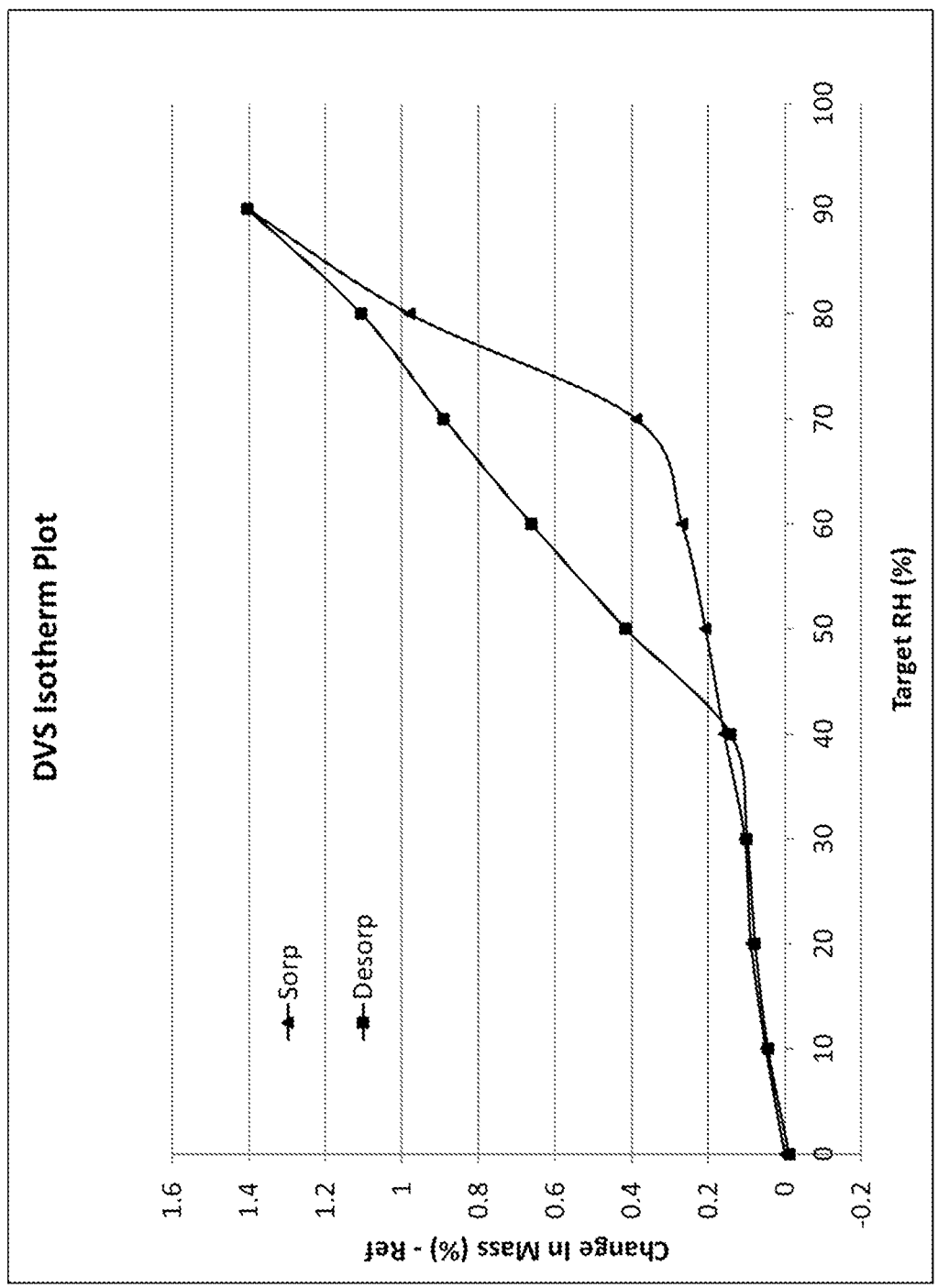
FIG. 34 provides a DVS analysis for Compound 1—Polymorph Form I.

In some embodiments, Form I is characterized by absorbing about 1.4 wt % water at about 25° C. and between about 0% and 90% relative humidity. In some embodiments, the dynamic vapor sorption mass uptake profile is substantially as set forth in FIG. 34.

In some embodiments, Form I is prepared by a process comprising: (1) contacting Compound 1 or a salt thereof with a solvent chosen from acetone, ethyl acetate, an alcohol, methyl ethyl ketone, methyl isobutyl ketone, tetrahydrofuran, dichloromethane, and di-butyl ether and mixtures of such solvents; and (2) isolating the solid product. In some embodiments, the solvent comprises acetone. In some embodiments, the solvent comprises ethyl acetate. In some embodiments, the solvent comprises an alcohol chosen from ethanol and isopropyl alcohol. In some embodiments, the solvent comprises ethanol.

In some embodiments, the process further comprises filtering the mixture of Compound 1 or a salt thereof and the solvent prior to isolating the solid product. In some embodiments, the process further comprises heating the mixture of Compound 1 or a salt thereof and the solvent. In some embodiments, the mixture is heated to about 50-70° C., for example about 60° C. In some embodiments, the filtering is conducted prior to heating. In some embodiments, the filtering is conducted before and after heating. In some embodiments, the process further comprises drying the solid product and/or the filtrate.

In some embodiments, the process further comprises washing and/or crystallizing the solid product with a second solvent chosen from acetone, ethyl acetate, an alcohol or a mixture of such solvents and optionally drying. In some embodiments, the washing comprises washing the solid product with an ethyl acetate and alcohol mixture. In some embodiments, the washing comprises washing the solid product with an ethyl acetate and ethanol mixture.

In some embodiments, Form I is prepared by a process comprising: (1) contacting Compound 1 or a salt thereof with a buffer to produce a mixture; (2) adding a solvent chosen from acetonitrile and an acetonitrile/water mix to the mixture to produce a slurry; (3) mixing the slurry; and (4) isolating the solid product. In some embodiments, the salt is a sodium salt of Compound 1. In some embodiments, the pH of the buffer is from about 1 to about 6. In some embodiments, the pH of the buffer is from about 2 to about 4. In some embodiments, the pH of the buffer is about 2.

In some embodiments, Form I is prepared by a process comprising: (1) contacting Form II of Compound 1, Form III of Compound 1, or Form IV of Compound 1, or a salt thereof, with an alcohol; and (2) isolating the solid product.

In some embodiments, the alcohol is chosen from ethanol and isopropyl alcohol. In some embodiments, the alcohol is ethanol.

In some embodiments, the crystalline form of Compound 1 is characterized by an x-ray powder diffraction pattern comprising peaks at about 6.1°±0.2°, 15.7°±0.2° and 16.1°±0.2° 2-θ. In some embodiments, the x-ray powder diffraction pattern one or more additional peaks chosen from peaks at about 15.4°±0.2°, 16.9°±0.2° and 19.9°±0.2° 2-θ. In some embodiments, the x-ray powder diffraction pattern comprises one or more additional peaks chosen from peaks at about 12.8°±0.2°, 13.9°±0.2° and 22.8°±0.2° 2-θ. In some embodiments, the x-ray powder diffraction pattern comprises one or more additional peaks chosen from peaks at about 10.5°±0.2°, 12.2°±0.2°, 13.3°±0.2°, 18.2°±0.2°, 19.0°±0 2° 19.4°±0.2°, 20.3°±0.2°, 21.1°±0.2°, 23.4°±0.2°, 25.2°±0.2°, 25.7°±0.2°, 26.7°±0.2° and 27.9°±0.2° 2-θ. In some embodiments, the crystalline form is characterized by an x-ray powder diffraction pattern that is substantially as set forth in FIG. 36.

In some embodiments, the crystalline form of Compound 1 is Form II. In some embodiments, Form II is characterized by having a differential scanning calorimetry thermogram comprising an endothermic peak with onset at about 163° C. In some embodiments, the differential scanning calorimetry thermogram is substantially as set forth in FIG. 37.

In some embodiments, Form II is characterized by having a thermogravimetric analysis thermogram showing a weight loss of about 0.6% over a temperature of from ambient temperature to about 210° C. In some embodiments, the thermogravimetric analysis thermogram is substantially as set forth in FIG. 38.

Figure 39:
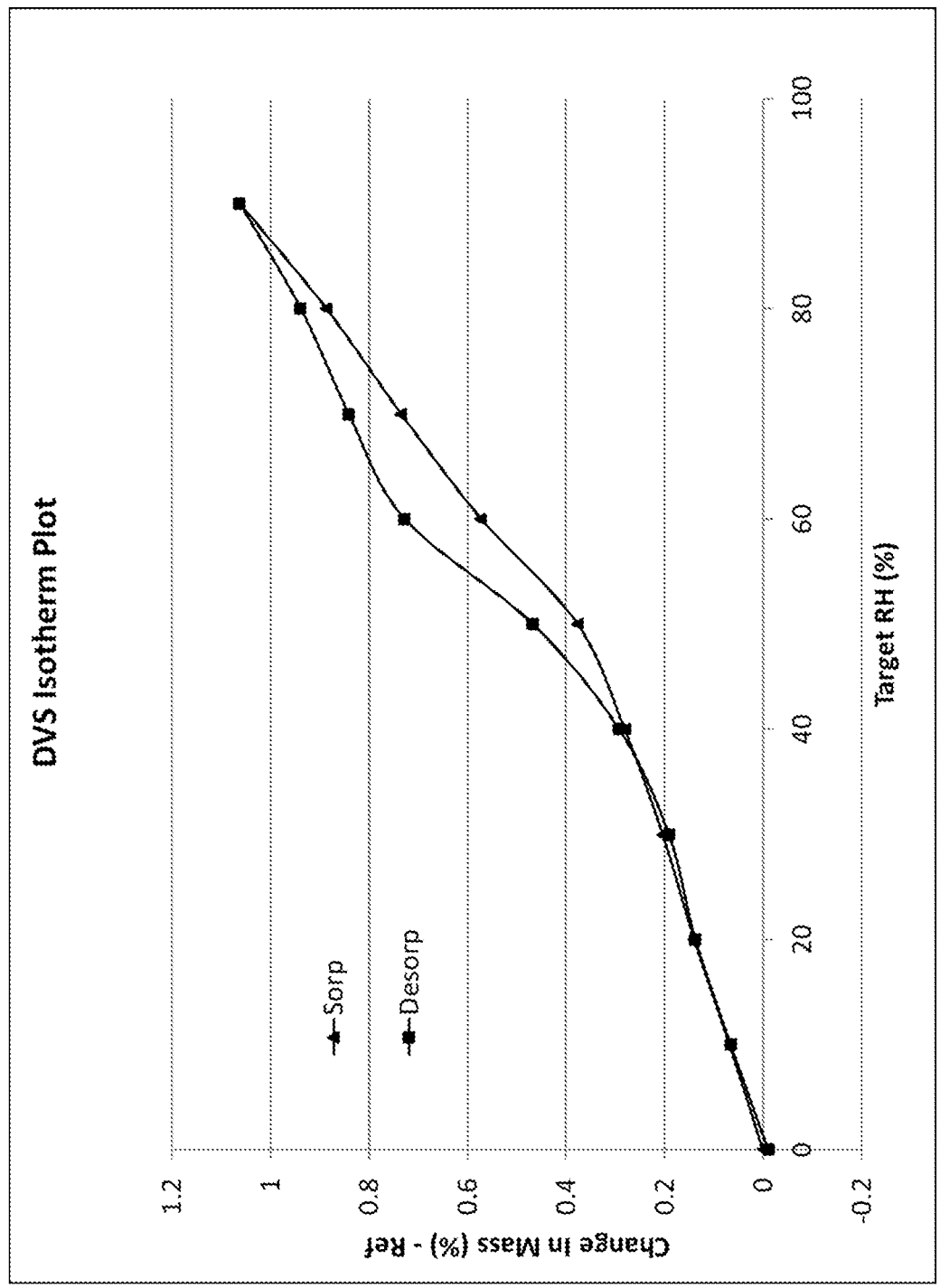
FIG. 39 provides a DVS analysis for Compound 1—Polymorph Form II.

In some embodiments, Form II is characterized by absorbing up to about 1.1 wt % water between about 0% and 90% relative humidity at about 25° C. In some embodiments, Form II is characterized by having a dynamic vapor sorption mass uptake profile substantially as set forth in FIG. 39.

In some embodiments, Form II is prepared by a process comprising: (1) contacting Compound 1 or a salt thereof with acetonitrile and optionally an acid; and (2) isolating the solid product. In some embodiments, the acid is HCl. In some embodiments, the process further comprises drying the solid product. In some embodiments, the salt of Compound 1 is the sodium salt.

In some embodiments, the crystalline form of Compound 1 is characterized by an x-ray powder diffraction pattern comprising peaks at about 8.0°±0.2°, 15.0°±0.2° and 18.4°±0.2° 2-θ. In some embodiments, the x-ray powder diffraction pattern comprises one or more additional peaks chosen from peaks at about 16.5°±0.2°, 22.1°±0.2° and 22.9°±0.2° 2-θ. In some embodiments, the x-ray powder diffraction pattern comprises one or more additional peaks chosen from peaks at about 12.5°±0.2°, 19.5°±0.2° and 23.6°±0.2° 2-θ. In some embodiments, the x-ray powder diffraction pattern comprises one or more additional peaks chosen from peaks at about 6.5°±0.2°, 12.3°±0.2°, 12.9°±0.2°, 13.6°±0.2°, 14.3°±0 2° 16.0°±0.2°, 18.1°±0.2°, 20.7°±0.2°, 24.1°±0.2°, 24.7°±0.2°, 26.8°±0.2° and 28.3°±0.2° 2-θ. In some embodiments, the crystalline form is characterized by an x-ray powder diffraction pattern that is substantially as set forth in FIG. 40.

In some embodiments, the crystalline form of Compound 1 is Form III. In some embodiments, Form III is characterized by having a differential scanning calorimetry thermogram comprising at least one endothermic peak chosen from peaks with onsets at about 20° C., 133° C. and 153° C. In some embodiments, the differential scanning calorimetry thermogram is substantially as set forth in FIG. 41.

In some embodiments, Form III is characterized by having a thermogravimetric analysis thermogram showing a weight loss of about 2.9% over a temperature of from about ambient temperature to about 90° C. In some embodiments, Form III is characterized by having a thermogravimetric analysis thermogram showing a weight loss of about 1.1% over a temperature of from about 90° C. to about 175° C. In some embodiments, Form III is characterized by having a thermogravimetric analysis thermogram showing a weight loss of about 1.6% over a temperature of from about 175° C. to about 225° C. In some embodiments, the thermogravimetric analysis thermogram is substantially as set forth in FIG. 42.

Figure 43:
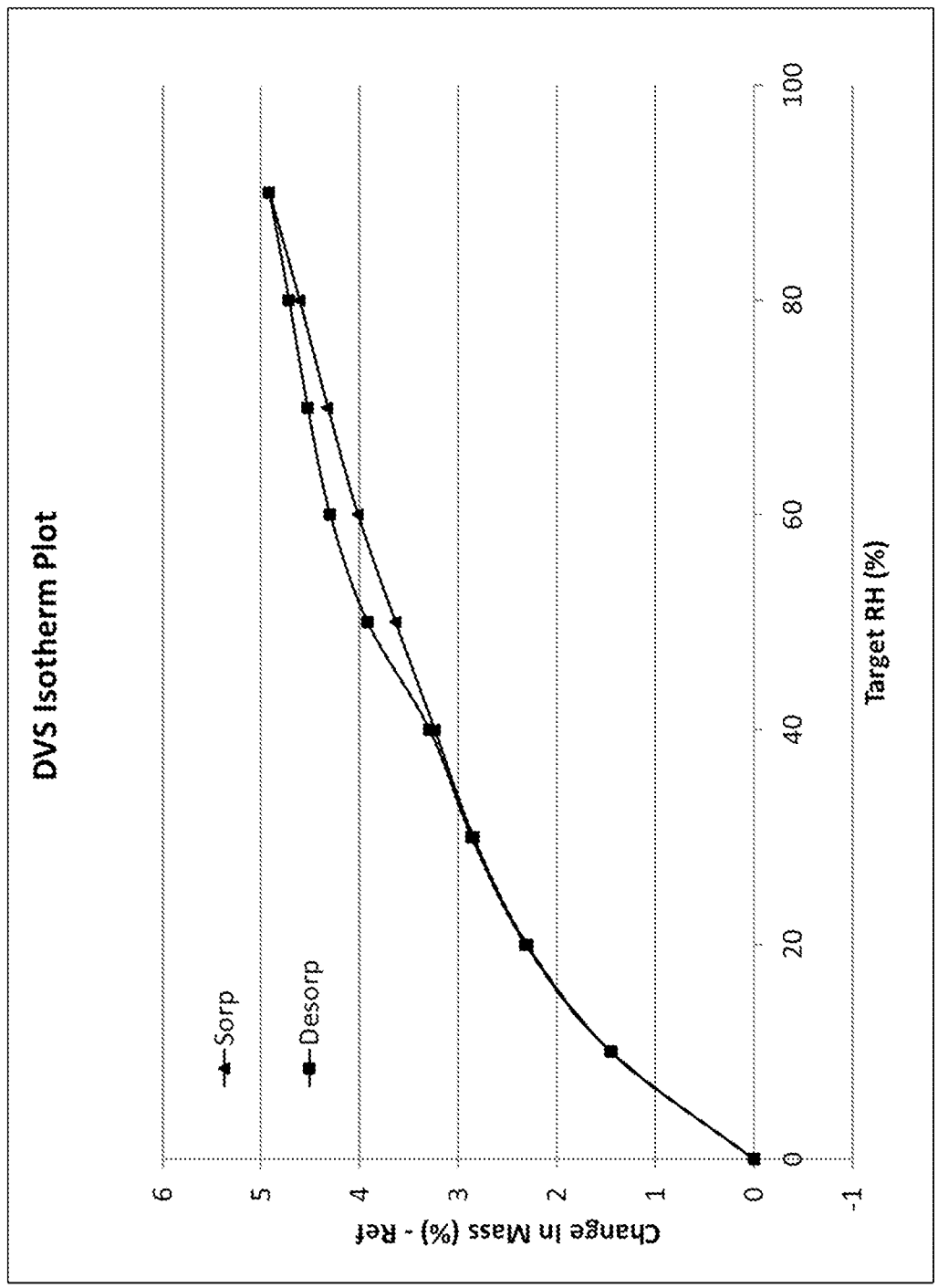
FIG. 43 provides a DVS analysis for Compound 1—Polymorph Form III.

In some embodiments, Form III is characterized by absorbing up to about 5 wt % water between about 0% and 90% relative humidity at about 25° C. In some embodiments, Form III is characterized by having a dynamic vapor sorption mass uptake profile substantially as set forth in FIG. 43.

In some embodiments, Form III is prepared by a process comprising: (1) contacting Compound 1 or a salt thereof with methanol and optionally an acid; and (2) isolating the solid product. In some embodiments, the acid is chosen from oxalic acid, phosphoric acid, citric acid, malic acid, and malonic acid. In some embodiments, the process further comprises drying the solid product. In some embodiments, the salt of Compound 1 is the sodium salt.

In some embodiments, the crystalline form of Compound 1 is characterized by an x-ray powder diffraction pattern comprising peaks at about 0.1°±0.2°, 8.7°±0.2° and 10.6°±0.2° 2-θ. In some embodiments, the x-ray powder diffraction pattern comprises one or more additional peaks chosen from peaks at about 10.3°±0.2°, 11.2°±0.2° and 18.2°±0.2° 2-θ. In some embodiments, the x-ray powder diffraction pattern comprises one or more additional peaks chosen from peaks at about 14.2°±0.2°, 20.5°±0.2° and 24.9°±0.2° 2-θ. In some embodiments, the x-ray powder diffraction pattern comprises one or more additional peaks chosen from peaks at about 3.3°±0.2°, 13.2°±0.2°, 15.4°±0.2° 16.2°±0.2°, 17.9°+0.2° 19.0°±0.2°, 21.3°±0.2°, 21.9°±0.2°, 23.3°±0.2°, 26.1°±0.2° and 28.3°±0.2° 2-θ. In some embodiments, the crystalline form is characterized by an x-ray powder diffraction pattern that is substantially as set forth in FIG. 44.

In some embodiments, the crystalline form of Compound 1 is Form IV. In some embodiments, Form IV is characterized by having a differential scanning calorimetry thermogram comprising at least one endothermic peak chosen from peaks with onsets at about 119° C. and 166° C. In some embodiments, the differential scanning calorimetry thermogram is substantially as set forth in FIG. 45.

In some embodiments, Form IV is characterized by having a thermogravimetric analysis thermogram showing a weight loss of about 0.6% over a temperature of from ambient temperature to about 200° C. In some embodiments, the thermogravimetric analysis thermogram is substantially as set forth in FIG. 46.

In some embodiments, Form IV is prepared by a process comprising: (1) contacting Compound 1 or a salt thereof with ethanol and/or heptane; and (2) isolating the solid product.

One aspect of the present disclosure relates to a crystalline form of a solvate of Compound 1.

Figure 47:
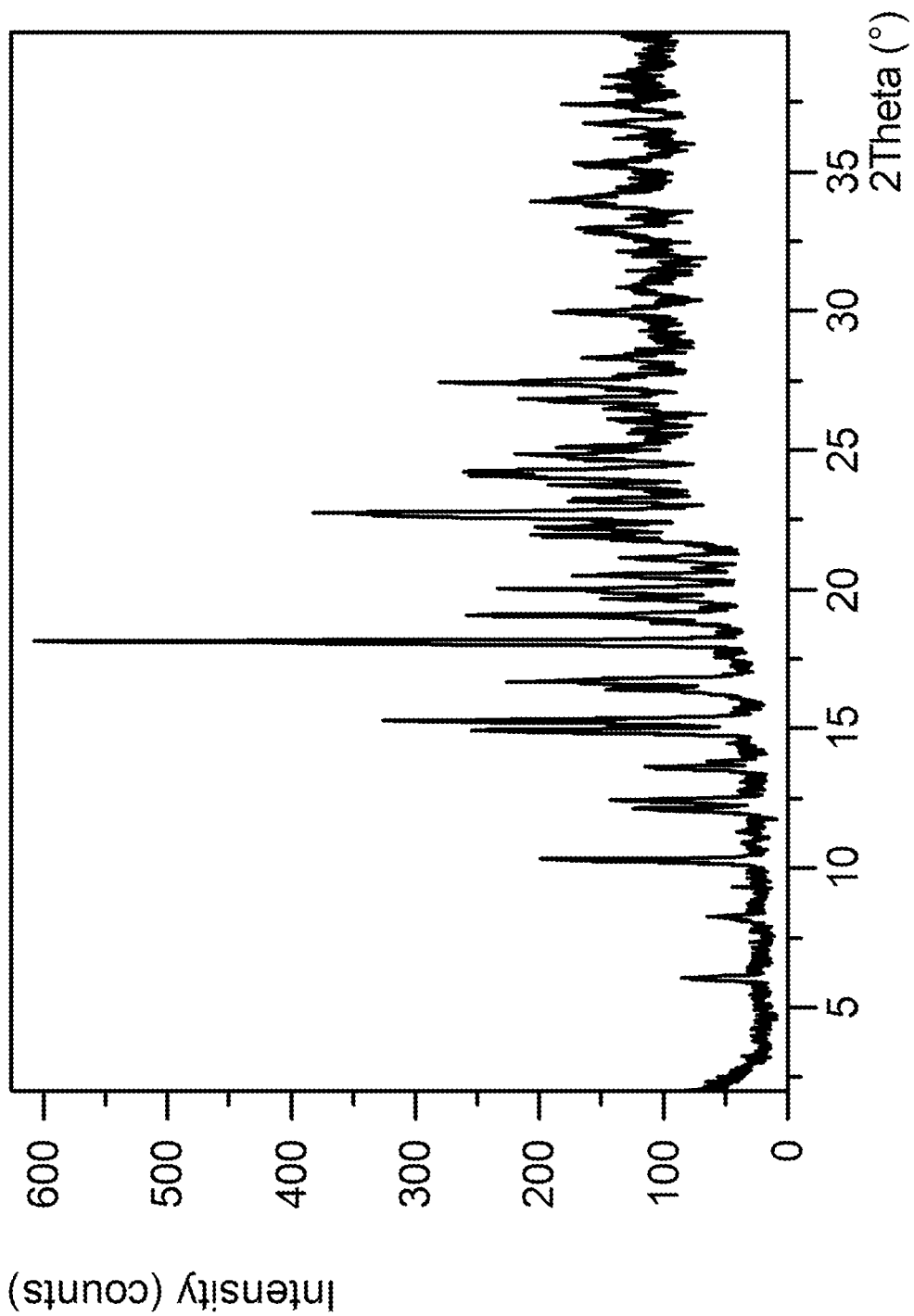
FIG. 47 provides an XRPD pattern for Compound 1—MeCN Solvate.

In some embodiments, the crystalline form of a solvate of Compound 1 is characterized by an x-ray powder diffraction pattern that is substantially as set forth in FIG. 47. In some embodiments, the crystalline form is the MeCN Solvate of Compound 1.

Figure 48:
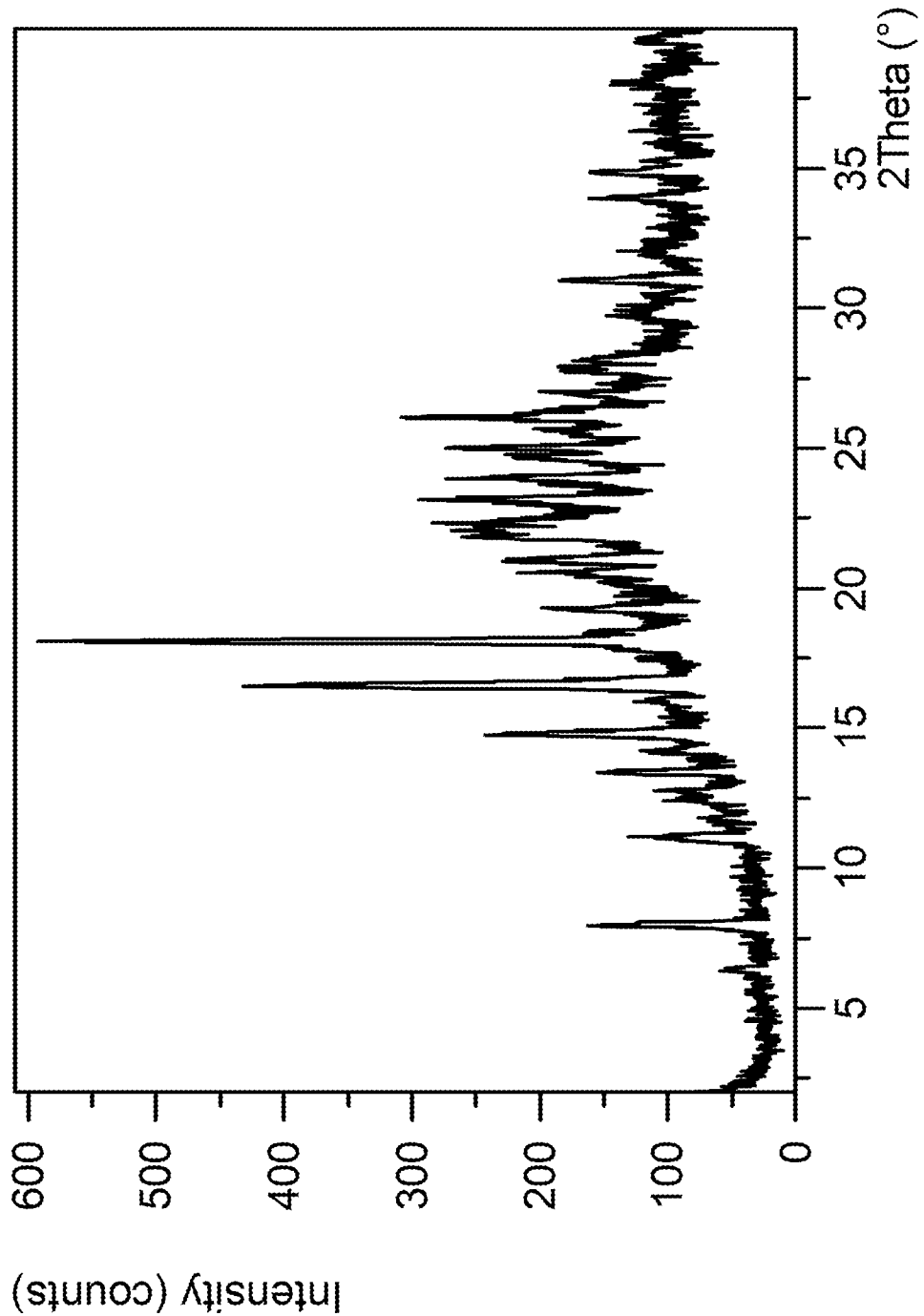
FIG. 48 provides an XRPD pattern for Compound 1—MeOH Solvate.

In some embodiments, the crystalline form of a solvate of Compound 1 is characterized by an x-ray powder diffraction pattern that is substantially as set forth in FIG. 48. In some embodiments, the crystalline form is the MeOH Solvate of Compound 1.

Figure 49:
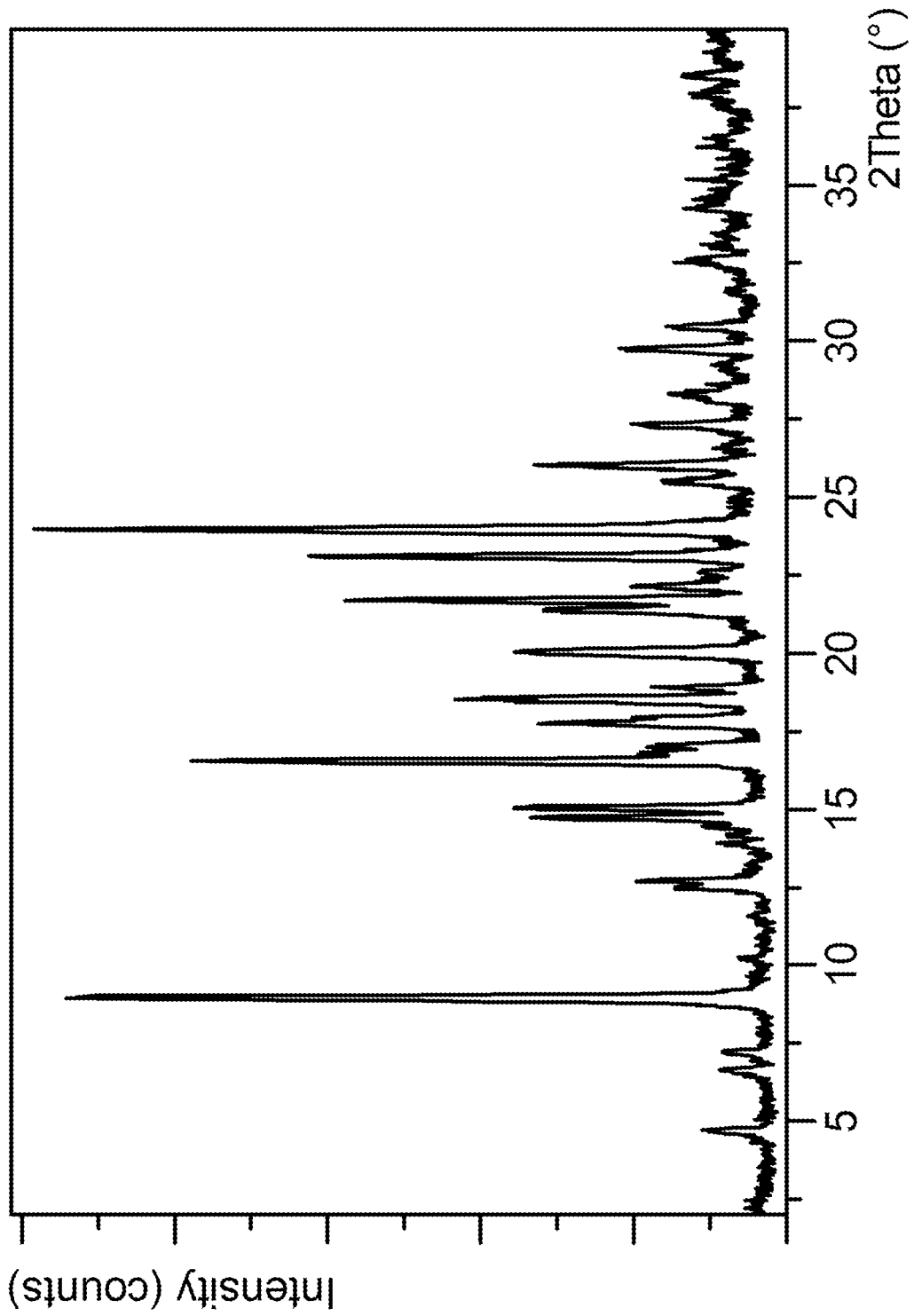
FIG. 49 provides an XRPD pattern for Compound 1—EtOAc Solvate.

In some embodiments, the crystalline form of a solvate of Compound 1 is characterized by an x-ray powder diffraction pattern that is substantially as set forth in FIG. 49. In some embodiments, the crystalline form is the EtOAC Solvate of Compound 1.

Figure 50:
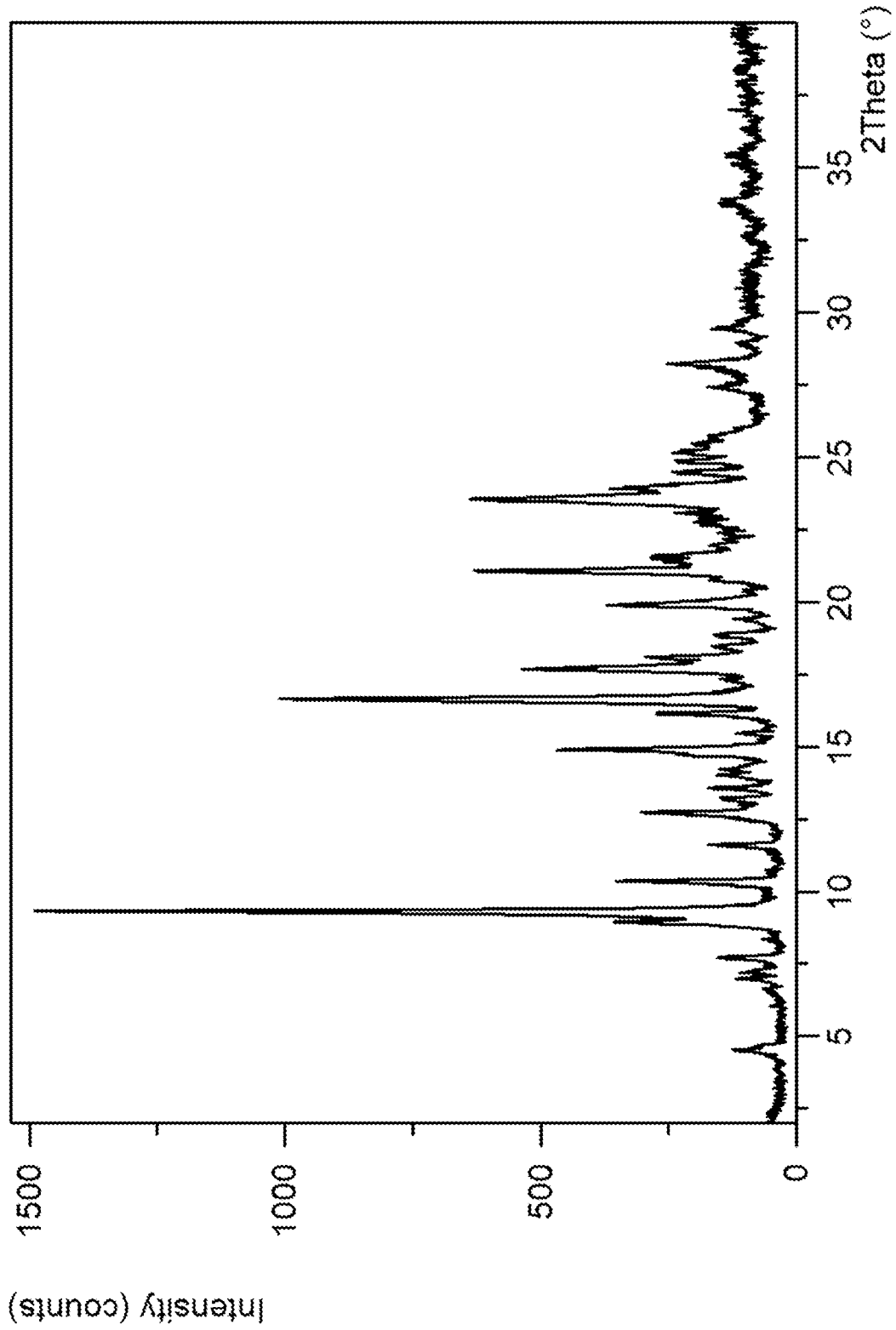
FIG. 50 provides an XRPD pattern for Compound 1—EtOAc Solvate, partially converted.

In some embodiments, the crystalline form of a solvate of Compound 1 is characterized by an x-ray powder diffraction pattern that is substantially as set forth in FIG. 50. In some embodiments, the crystalline form is the partially desolvated EtOAC Solvate of Compound 1.

Figure 51:
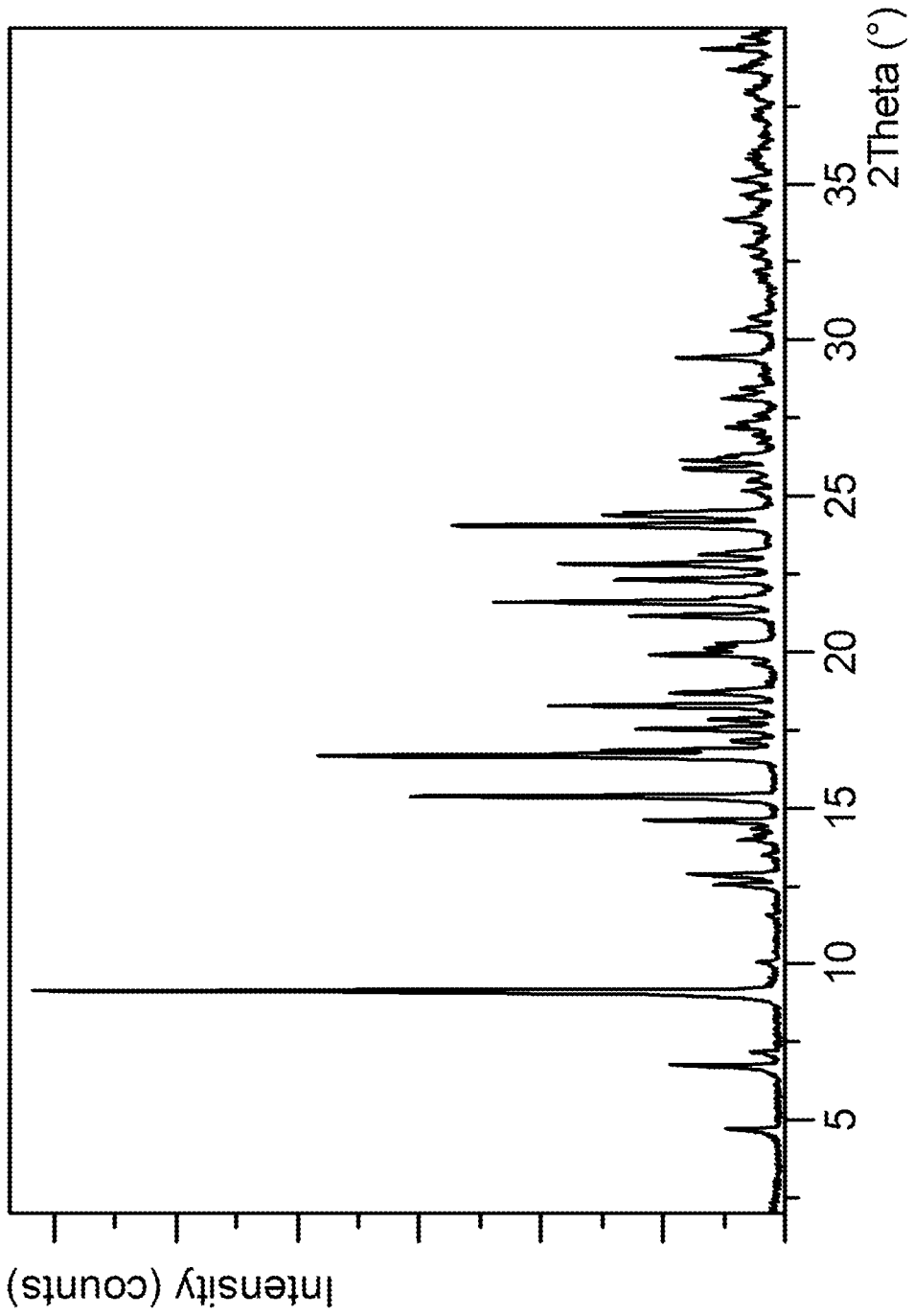
FIG. 51 provides an XRPD pattern for Compound 1—MeTHF Solvate.

In some embodiments, the crystalline form of a solvate of Compound 1 is characterized by an x-ray powder diffraction pattern that is substantially as set forth in FIG. 51. In some embodiments, the crystalline form is the MeTHF Solvate of Compound 1.

Figure 52:
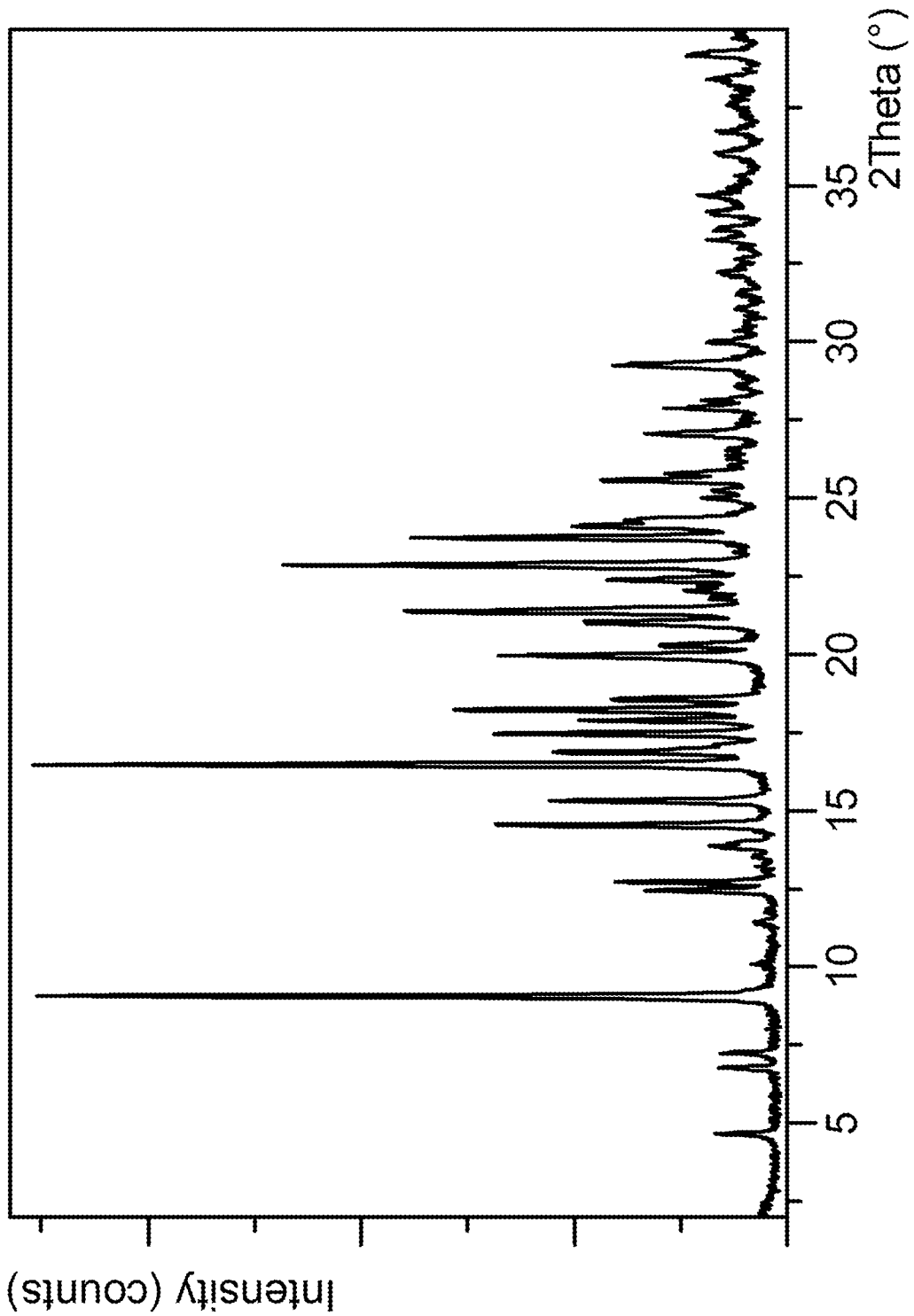
FIG. 52 provides an XRPD pattern for Compound 1—Toluene Solvate.

In some embodiments, the crystalline form of a solvate of Compound 1 is characterized by an x-ray powder diffraction pattern that is substantially as set forth in FIG. 52. In some embodiments, the crystalline form is the Toluene Solvate of Compound 1.

Figure 53:
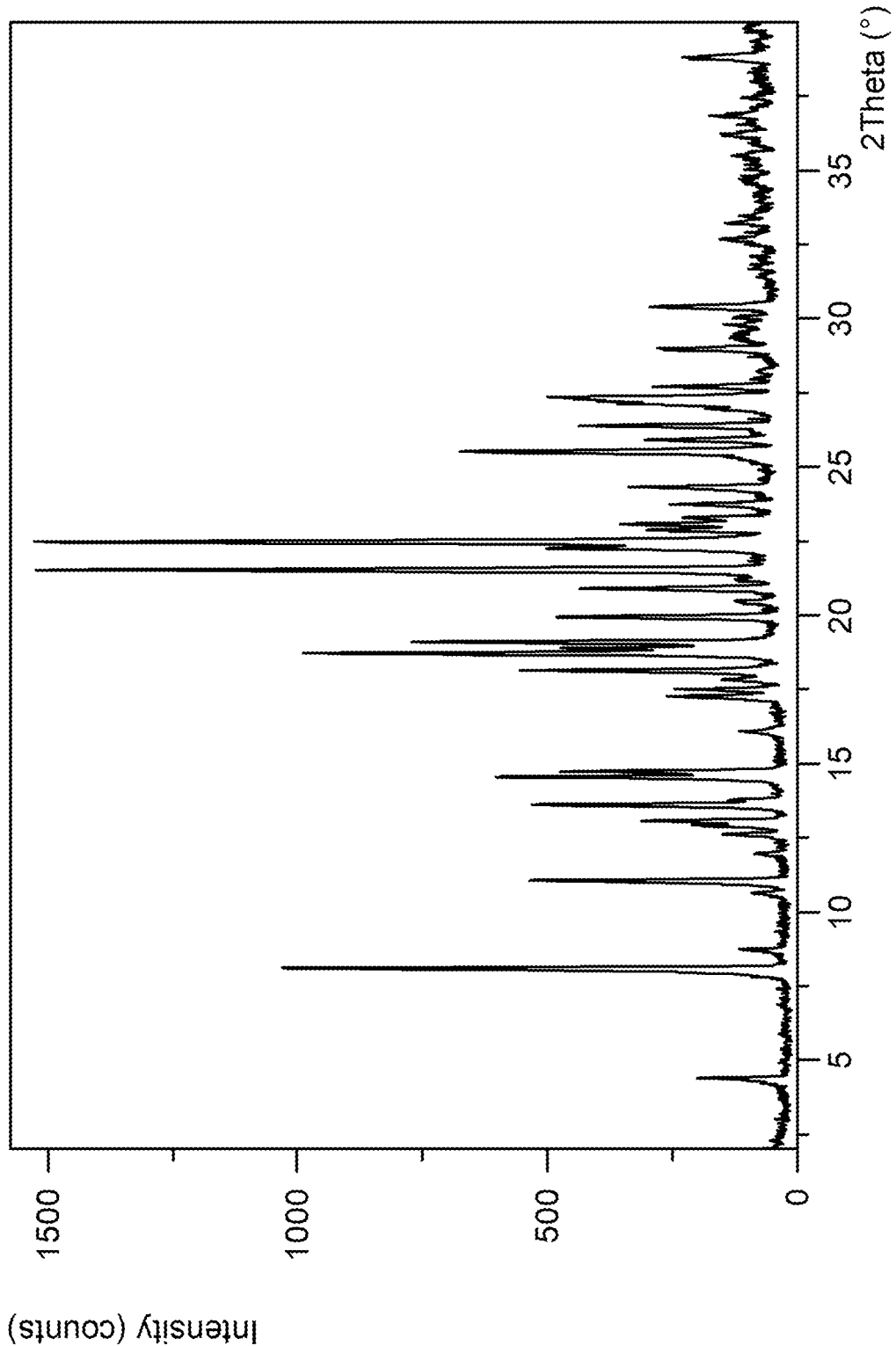
FIG. 53 provides an XRPD pattern for Compound 1—n-BuOAc Solvate.

In some embodiments, the crystalline form of a solvate of Compound 1 is characterized by an x-ray powder diffraction pattern that is substantially as set forth in FIG. 53. In some embodiments, the crystalline form is the nBuOAc Solvate of Compound 1.

Figure 54:
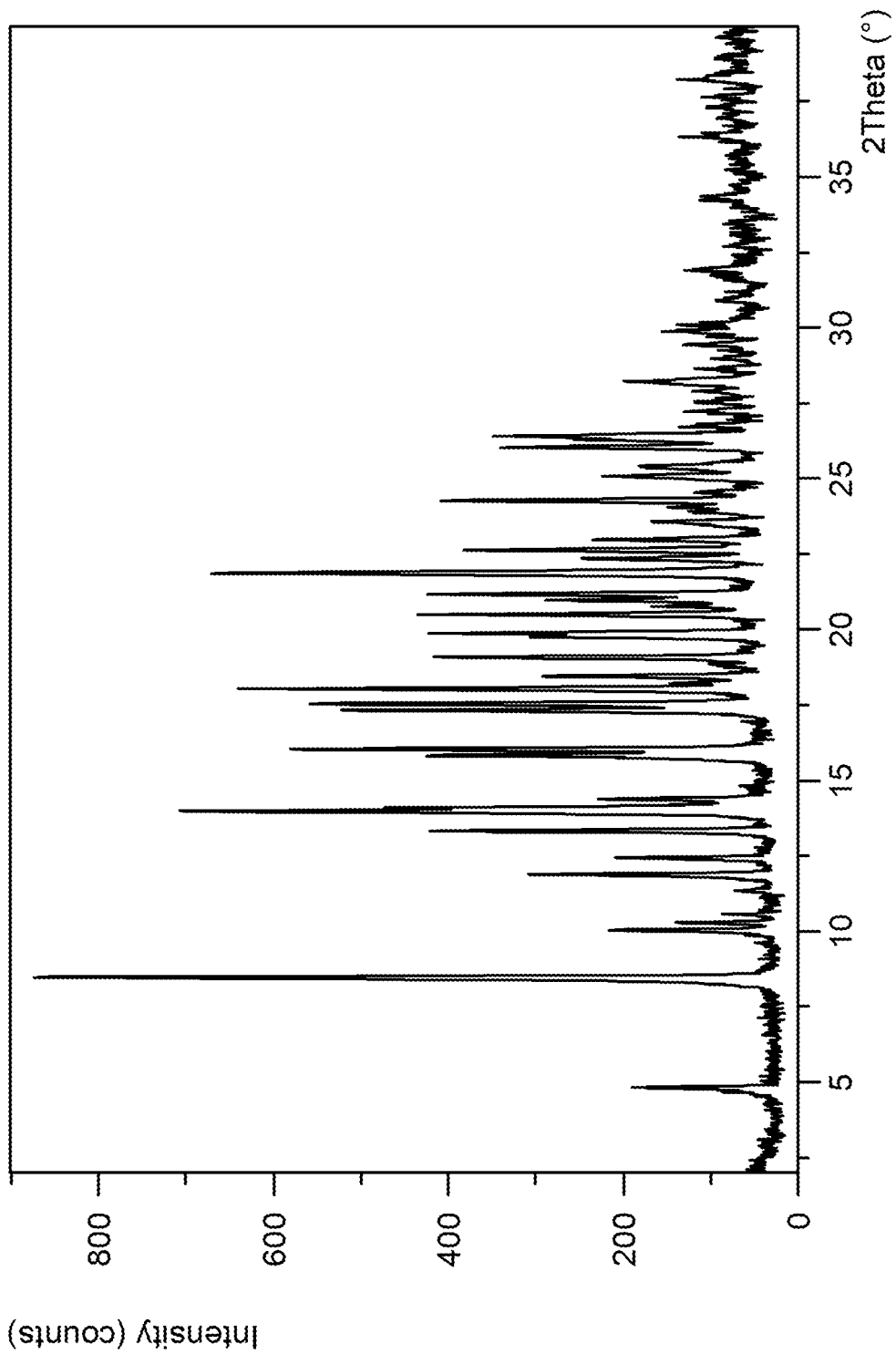
FIG. 54 provides an XRPD pattern for Compound 1—MTBE Solvate 1.

In some embodiments, the crystalline form of a solvate of Compound 1 is characterized by an x-ray powder diffraction pattern that is substantially as set forth in FIG. 54. In some embodiments, the crystalline form is the MTBE Solvate 1 of Compound 1.

Figure 55:
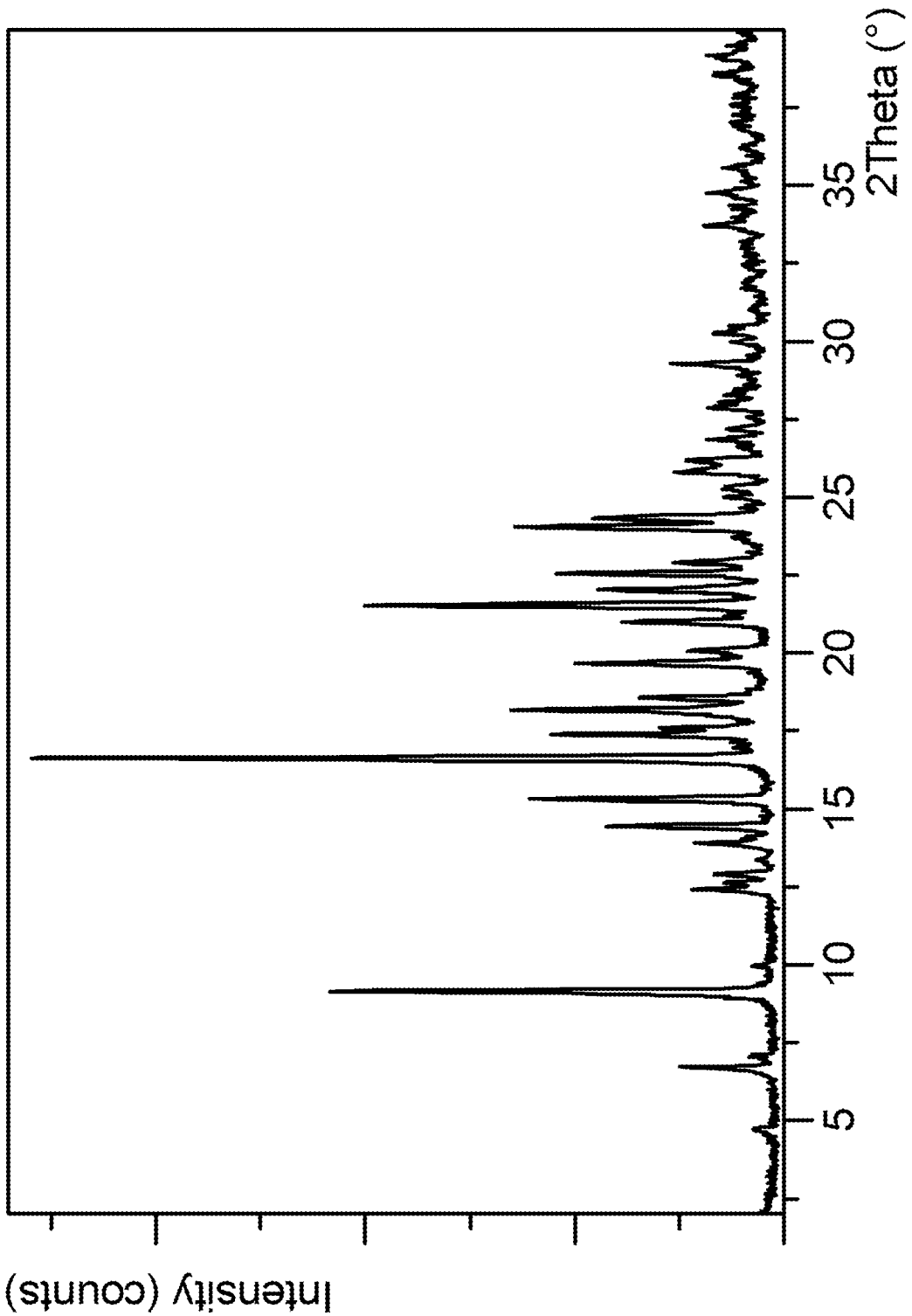
FIG. 55 provides an XRPD pattern for Compound 1—MTBE Solvate 2.

In some embodiments, the crystalline form of a solvate of Compound 1 is characterized by an x-ray powder diffraction pattern that is substantially as set forth in FIG. 55. In some embodiments, the crystalline form is the MTBE Solvate 2 of Compound 1.

Figure 56:
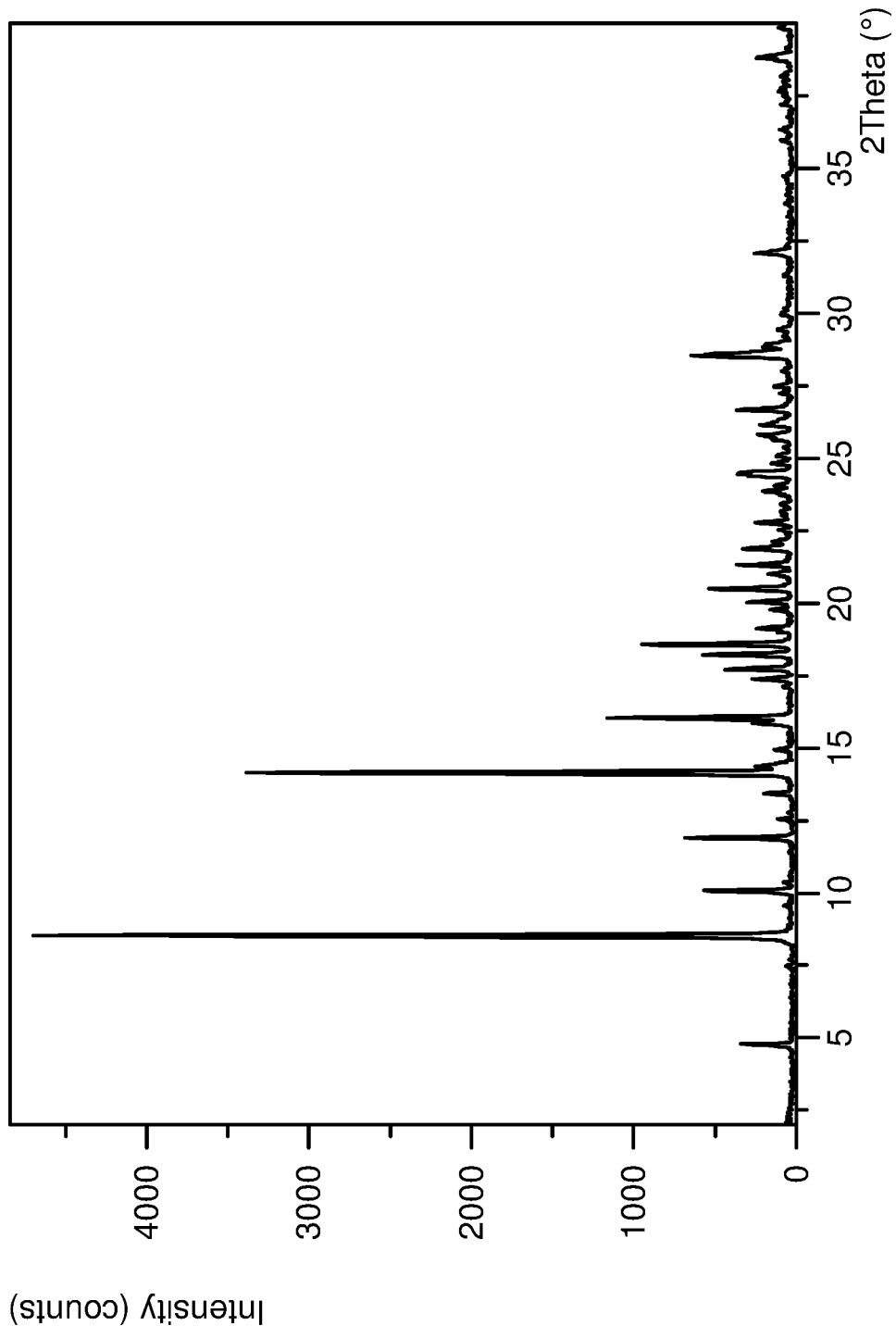
FIG. 56 provides an XRPD pattern for Compound 1—Isopropanol Hemi-solvate.

In some embodiments, the crystalline form of a solvate of Compound 1 is characterized by an x-ray powder diffraction pattern that is substantially as set forth in FIG. 56. In some embodiments, the crystalline form is the Isopropanol Hemisolvate of Compound 1.

B. Salts of Compound 1

One aspect of the present disclosure relates to a pharmaceutically acceptable salt of Compound 1:

Compound 1

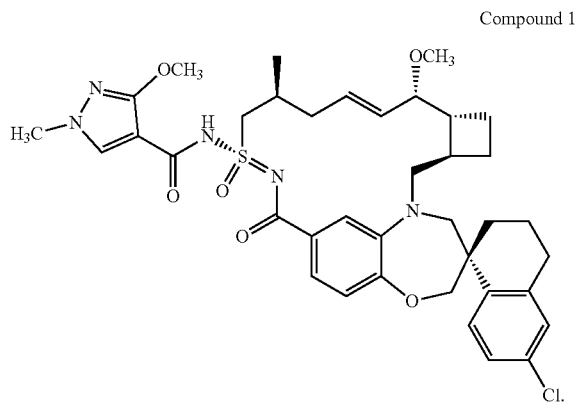 [SMILES: COc1nn(C)cc1C(=O)N[S@@]1(=O)=NC(=O)c2ccc3c(c2)N(C[C@@H]2CC[C@H]2[C@@H](OC)/C=C/C[C@H](C)C1)C[C@@]1(CCCc2cc(Cl)ccc21)CO3]

In some embodiments, the pharmaceutically acceptable salt is chosen from a sodium salt, potassium salt, diethylamine salt and a choline salt.

Another aspect of the present disclosure relates to crystalline forms of a pharmaceutically acceptable salt of Compound 1:

Compound 1

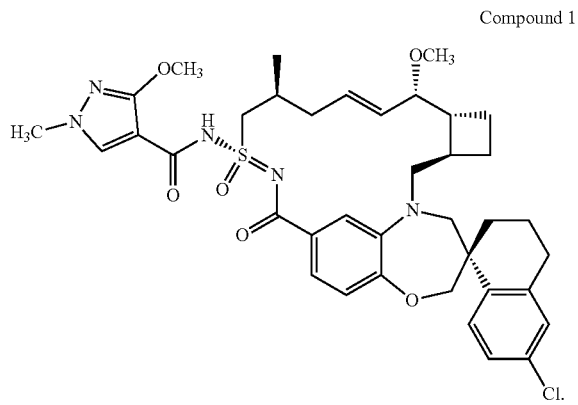 [SMILES: COc1nn(C)cc1C(=O)N[S@@]1(=O)=NC(=O)c2ccc3c(c2)N(C[C@@H]2CC[C@H]2[C@@H](OC)/C=C/C[C@H](C)C1)C[C@@]1(CCCc2cc(Cl)ccc21)CO3]

In some embodiments, the pharmaceutically acceptable salt is chosen from a sodium salt, potassium salt, diethylamine salt and a choline salt.

In some embodiments, the pharmaceutically acceptable salt of Compound 1 is a sodium salt. In some embodiments, the sodium salt of Compound 1 is characterized by an x-ray powder diffraction pattern comprising peaks at about 7.6°±0.2°, 8.4°±0.2° and 12.8°±0.2° 2-θ. In some embodiments, the x-ray powder diffraction pattern comprises one or more additional peaks chosen from peaks at about 15.3°±0.2°, 18.4°±0.2° and 20.4°±0.2° 2-θ. In some embodiments, the x-ray powder diffraction pattern comprises one or more additional peaks chosen from peaks at about 12.3°±0.2°, 13.4°±0.2° and 24.0°±0.2° 2-θ. In some embodiments, the x-ray powder diffraction pattern comprises one or more additional peaks chosen from peaks at about 6.7°±0.2°, 13.7°±0.2°, 14.0°±0.2°, 15.7°±0.2°, 17.1°±0.2°, 17.40±0.20, 17.90±0.20, 19.20±0.20, 22.00±0.20, 22.20±0.20, 23.60±0.20, 24.30±0.20 and 24.8°±0.2° 2-θ. In some embodiments, the pharmaceutically acceptable Na Salt Form 1 of Compound 1 is characterized by an x-ray powder diffraction pattern that is substantially as set forth in FIG. 1.

In some embodiments, the crystalline form of a pharmaceutically acceptable salt of Compound 1 is Na Salt Form 1. In some embodiments, the Na Salt Form 1 is characterized by having a differential scanning calorimetry thermogram comprising at least one endothermic peak chosen from peaks with onsets at about 14° C., 83° C. and 232° C. In some embodiments, the differential scanning calorimetry thermogram is substantially as set forth in FIG. 2.

In some embodiments, the Na Salt Form 1 is characterized by having a thermogravimetric analysis thermogram showing a weight loss of about 4.2% over a temperature of from ambient temperature to about 200° C. In some embodiments, the thermogravimetric analysis thermogram is substantially as set forth in FIG. 3.

In some embodiments, the Na Salt Form 1 is characterized by absorbing about 7.5 wt % water between about 0% and 90% relative humidity at about 25° C. In some embodiments, the Na Salt Form 1 is characterized by having a dynamic vapor sorption mass uptake profile substantially as set forth in FIG. 4.

In some embodiments, the sodium salt of Compound 1 is characterized by an x-ray powder diffraction pattern comprising peaks at about 7.2°±0.2°, 14.7°±0.2° and 19.3°±0.2° 2-θ. In some embodiments, the x-ray powder diffraction pattern comprises one or more additional peaks chosen from peaks at about 11.1°±0.2°, 17.1°±0.2° and 20.7°±0.2° 2-θ. In some embodiments, the x-ray powder diffraction pattern comprises one or more additional peaks chosen from peaks at about 13.1°±0.2°, 14.5°±0.2° and 16.9°±0.2° 2-θ. In some embodiments, the x-ray powder diffraction pattern comprises one or more additional peaks chosen from peaks at about 6.7°±0.2°, 9.1±0.2°, 9.7°±0.2°, 12.1°±0.2°, 15.2°±0.2°, 17.3°±0.20, 17.50±0.20, 17.80±0.20, 18.20±0.20, 19.10±0.20, 21.60±0.20, 22.00±0.20, 22.80±0.2°, 24.4°±0.2° and 25.1°±0.2° 2-θ. In some embodiments, the pharmaceutically acceptable salt of Compound 1 is characterized by an x-ray powder diffraction pattern that is substantially as set forth in FIG. 5.

In some embodiments, the crystalline form of a pharmaceutically acceptable salt of Compound 1 is Na Salt Form 2. In some embodiments, the Na Salt Form 2 is characterized by having a differential scanning calorimetry thermogram comprising at least one endothermic peak chosen from peaks with onsets at about 21° C. and 224° C. In some embodiments, the Na Salt Form 2 is characterized by having a differential scanning calorimetry thermogram comprising an exothermic peak with onset at about 109° C. In some embodiments, the differential scanning calorimetry thermogram is substantially as set forth in FIG. 6.

In some embodiments, the Na Salt Form 2 is characterized by having a thermogravimetric analysis thermogram showing a weight loss of about 4.8% over a temperature of from ambient temperature to about 200° C. In some embodiments, the thermogravimetric analysis thermogram is substantially as set forth in FIG. 7.

In some embodiments, the sodium salt of Compound 1 is characterized by an x-ray powder diffraction pattern comprising peaks at about 4.1°±0.2°, 13.2°±0.2° and 18.8°±0.2° 2-θ. In some embodiments, the x-ray powder diffraction pattern comprises one or more additional peaks chosen from peaks at about 12.1°±0.2°, 20.0°±0.2° and 24.2°±0.2° 2-θ. In some embodiments, the x-ray powder diffraction pattern comprises one or more additional peaks chosen from peaks at about 14.8°±0.2°, 20.9°±0.2° and 22.9°±0.2° 2-θ. In some embodiments, the x-ray powder diffraction pattern comprises one additional peak at about 8.2°±0.2° 2-θ. In some embodiments, the pharmaceutically acceptable salt of Compound 1 is characterized by an x-ray powder diffraction pattern that is substantially as set forth in FIG. 8.

In some embodiments, the crystalline form of a pharmaceutically acceptable salt of Compound 1 is Na Salt Form 3. In some embodiments, the Na Salt Form 3 is characterized by having a differential scanning calorimetry thermogram comprising at least one endothermic peak chosen from peaks with onsets at about 19° C. and 219° C. In some embodiments, the differential scanning calorimetry thermogram is substantially as set forth in FIG. 9.

In some embodiments, the Na Salt Form 3 is characterized by having a thermogravimetric analysis thermogram showing a weight loss of about 5.1% over a temperature of from ambient temperature to about 200° C. In some embodiments, the thermogravimetric analysis thermogram is substantially as set forth in FIG. 10.

In some embodiments, the sodium salt form of Compound 1 is characterized by an x-ray powder diffraction pattern comprising peaks at about 6.7°±0.2°, 13.3°±0.2° and 20.2°±0.2° 2-θ. In some embodiments, the x-ray powder diffraction pattern comprises one or more additional peaks chosen from peaks at about 16.0°±0.2°, 21.0°±0.2° and 23.4°±0.2° 2-θ. In some embodiments, the x-ray powder diffraction pattern comprises one or more additional peaks chosen from peaks at about 7.2°±0.2°, 21.5°±0.2° and 22.8°±0.2° 2-θ. In some embodiments, the x-ray powder diffraction pattern comprises one or more additional peaks chosen from peaks at about 7.5°±0.2°, 8.3°±0.2°, 9.4°±0.2°, 11.9°±0.2°, 12.8°±0.2°, 14.8°±0.20, 15.50±0.20, 16.50±0.20, 16.80±0.20, 18.20±0.20, 18.90±0.20, 24.20±0.20, 25.90±0.2° and 26.8°±0.2° 2-θ. In some embodiments, the pharmaceutically acceptable salt of Compound 1 is characterized by an x-ray powder diffraction pattern that is substantially as set forth in FIG. 11.

In some embodiments, the crystalline form of a pharmaceutically acceptable salt of Compound 1 is Na Salt Form 4.

In some embodiments, the sodium salt of Compound 1 is characterized by an x-ray powder diffraction pattern comprising peaks at about 7.6°±0.2°, 13.9°±0.2° and 15.4°±0.2° 2-θ. In some embodiments, the x-ray powder diffraction pattern comprises one or more additional peaks chosen from peaks at about 6.0°±0.2°, 8.9°±0.2° and 12.1°±0.2° 2-θ. In some embodiments, the x-ray powder diffraction pattern comprises one or more additional peaks chosen from peaks at about 17.0°±0.2°, 21.7°±0.2° and 23.0°±0.2° 2-θ. In some embodiments, the x-ray powder diffraction pattern comprises one or more additional peaks chosen from peaks at about 5.2°±0.2°, 12.7°±0.2°, 14.5°±0.2°, 17.3°±0.2°, 17.7°±0.2°, 18.6°±0.2°, 18.9°±0.2°, 19.7°±0.2°, 20.2°±0.2°, 22.1°±0.2°, 22.4°±0.2°, 23.5°±0.2°, 24.3°±0.2°, 25.4°±0.2°, 28.0°±0.2°, 29.5°±0.2° and 37.2°±0.2° 2-θ. In some embodiments, the pharmaceutically acceptable salt of Compound 1 is characterized by an x-ray powder diffraction pattern that is substantially as set forth in FIG. 12.

In some embodiments, the crystalline form of a pharmaceutically acceptable salt of Compound 1 is Na Salt Form 5. In some embodiments, the Na Salt Form 5 is characterized by having a differential scanning calorimetry thermogram comprising at least one endothermic peak chosen from peaks with onsets at about 29° C. and 143° C. In some embodiments, the Na Salt Form 5 is characterized by having a differential scanning calorimetry thermogram comprising an exothermic peak with onset at about 198° C. In some embodiments, the differential scanning calorimetry thermogram is substantially as set forth in FIG. 13.

In some embodiments, the Na Salt Form 5 is characterized by having a thermogravimetric analysis thermogram showing a weight loss of about 4.2% over a temperature of from ambient temperature to about 200° C. In some embodiments, the thermogravimetric analysis thermogram is substantially as set forth in FIG. 14.

In some embodiments, the pharmaceutically acceptable salt of Compound 1 is a potassium salt. In some embodiments, the potassium salt of Compound 1 is characterized by an x-ray powder diffraction pattern comprising peaks at about 7.6°±0.2°, 8.2°±0.2° and 12.7°±0.2° 2-θ. In some embodiments, the x-ray powder diffraction pattern comprises one or more additional peaks chosen from peaks at about 13.4°±0.2°, 18.2°±0.2° and 21.9°±0.2° 2-θ. In some embodiments, the x-ray powder diffraction pattern comprises one or more additional peaks chosen from peaks at about 12.3°±0.2°, 15.3°±0.2° and 20.1°±0.2° 2-θ. In some embodiments, the x-ray powder diffraction pattern comprises one or more additional peaks chosen from peaks at about 6.7°±0.2°, 9.3°±0.2°, 11.1°±0.2°, 13.7°±0.2°, 14.0°±0.2° 16.2°±0.2°, 17.1°±0.2°, 17.7°±0.2°, 19.2°±0.2°, 22.2°±0.2°, 23.5°±0.2°, 24.1°±0.2° and 24.7°±0.2° 2-θ. In some embodiments, the pharmaceutically acceptable salt of Compound 1 is characterized by an x-ray powder diffraction pattern that is substantially as set forth in FIG. 15.

In some embodiments, the crystalline form of a pharmaceutically acceptable salt of Compound 1 is K Salt Form 1. In some embodiments, the K Salt Form 1 is characterized by having a differential scanning calorimetry thermogram comprising at least one endothermic peak chosen from peaks with onsets at about 14° C., 182° C. and 233° C. In some embodiments, the differential scanning calorimetry thermogram is substantially as set forth in FIG. 17.

In some embodiments, the K Salt Form 1 is characterized by having a thermogravimetric analysis thermogram showing a weight loss of about 4.2% over a temperature of from ambient temperature to about 200° C. In some embodiments, the thermogravimetric analysis thermogram is substantially as set forth in FIG. 18.

In some embodiments, the K Salt Form 1 is characterized by absorbing about 11 wt % water between about 0% and 90% relative humidity at about 25° C. In some embodiments, the K Salt Form 1 is characterized by having a dynamic vapor sorption mass uptake profile substantially as set forth in FIG. 19.

In some embodiments, the pharmaceutically acceptable salt of Compound 1 is a diethylamine salt. In some embodiments, the diethylamine salt of Compound 1 is characterized by an x-ray powder diffraction pattern comprising peaks at about 9.0°±0.2°, 9.5°±0.2° and 12.7°±0.2° 2-θ. In some embodiments, the x-ray powder diffraction pattern comprises one or more additional peaks chosen from peaks at about 6.2°±0.2°, 12.5°±0.2° and 13.1°±0.2° 2-θ. In some embodiments, the x-ray powder diffraction pattern comprises one or more additional peaks chosen from peaks at about 4.3°±0.2°, 14.1°±0.2° and 17.0°±0.2° 2-θ. In some embodiments, the x-ray powder diffraction pattern comprises one or more additional peaks chosen from peaks at about 5.2°±0.2°, 8.5°±0.2°, 10.5°±0.2°, 16.1°±0.2°, 19.5°+0.2° 21.1°±0.2° and 26.4°±0.2° 2-θ. In some embodiments, the x-ray powder diffraction pattern is substantially as set forth in FIG. 23.

In some embodiments, the crystalline form of a pharmaceutically acceptable salt of Compound 1 is diethylamine salt Form 1. In some embodiments, the diethylamine salt Form 1 is characterized by having a differential scanning calorimetry thermogram comprising at least one endothermic peak chosen from peaks with onsets at about 17° C. and 145° C. In some embodiments, the differential scanning calorimetry thermogram is substantially as set forth in FIG. 24. In some embodiments, the diethylamine Salt Form 1 is characterized by having a thermogravimetric analysis thermogram showing a weight loss of about 8.4% over a temperature of from ambient temperature to about 170° C. In some embodiments, the thermogravimetric analysis thermogram is substantially as set forth in FIG. 25. In some embodiments, the Diethylamine Salt Form 1 is characterized by absorbing about 5.5 wt % water between about 0% and 90% relative humidity at about 25° C. In some embodiments, the diethylamine Salt Form 1 is characterized by having a dynamic vapor sorption mass uptake profile substantially as set forth in FIG. 26.

In some embodiments, the pharmaceutically acceptable salt of Compound 1 is a choline salt. In some embodiments, the choline salt of Compound 1 is characterized by an x-ray powder diffraction pattern comprising peaks at about 10.4°±0.2°, 20.9°±0.2° and 22.9°±0.2° 2-θ. In some embodiments, the x-ray powder diffraction pattern comprises one or more additional peaks chosen from peaks at about 14.0°±0.2°, 15.7°±0.2° and 24.0°±0.2° 2-θ. In some embodiments, the x-ray powder diffraction pattern comprises one or more additional peaks chosen from peaks at about 14.4°±0.2°, 16.8°±0.2° and 25.1°±0.2° 2-θ. In some embodiments, the x-ray powder diffraction pattern comprises one or more additional peaks chosen from peaks at about 4.8°±0.2°, 11.0°±0.2°, 11.4°±0.2°, 13.2°±0.2°, 15.6°±0.2° 16.1°±0.2°, 17.2°±0.2°, 18.2°±0.2°, 18.9°±0.2°, 19.4°±0.2°, 20.2°±0.2°, 27.0°±0.2° and 28.0°±0.2° 2-θ. In some embodiments, the pharmaceutically acceptable salt of Compound 1 is characterized by an x-ray powder diffraction pattern that is substantially as set forth in FIG. 27.

In some embodiments, the crystalline form of a pharmaceutically acceptable salt of Compound 1 is Choline Salt Form 1. In some embodiments, wherein the Choline Salt Form 1 is characterized by having a differential scanning calorimetry thermogram comprising at least one endothermic peak chosen from peaks with onsets at about 23° C., 99° C. and 156° C. In some embodiments, the differential scanning calorimetry thermogram is substantially as set forth in FIG. 28. In some embodiments, the Choline Salt Form 1 is characterized by having a thermogravimetric analysis thermogram showing a weight loss of about 8.8% over a temperature of from ambient temperature to about 200° C. In some embodiments, the thermogravimetric analysis thermogram is substantially as set forth in FIG. 29.

One aspect of the present disclosure relates to a crystalline form of a solvate of a pharmaceutically acceptable salt of Compound 1.

In some embodiments, the solvate is a potassium salt solvate. In some embodiments, the potassium salt solvate is characterized by an x-ray powder diffraction pattern that is substantially as set forth in FIG. 20. In some embodiments, the solvate is a potassium salt IPA solvate.

Figure 21:
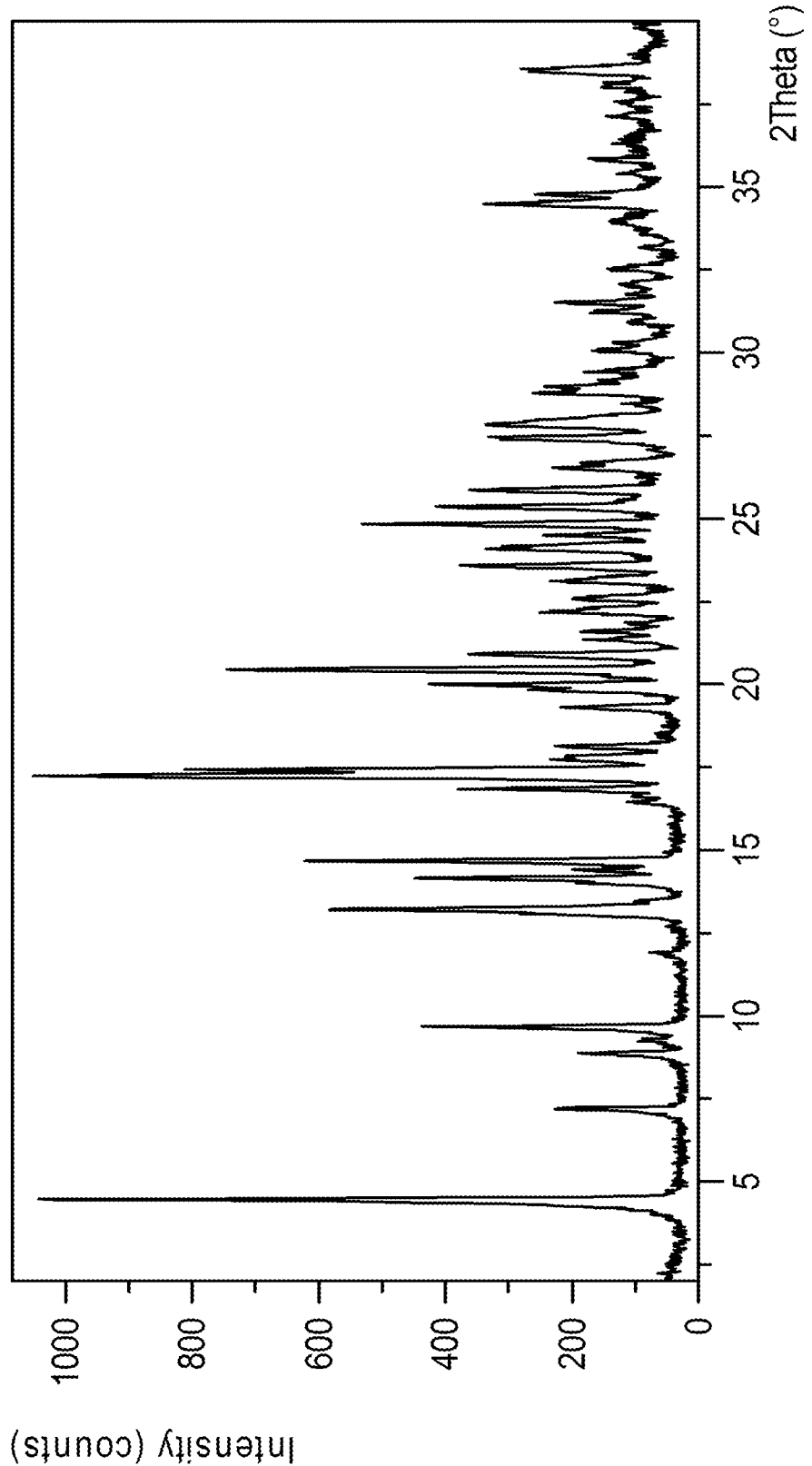
FIG. 21 provides an XRPD pattern for K Salt THF Solvate.

In some embodiments, the potassium salt solvate is characterized by an x-ray powder diffraction pattern that is substantially as set forth in FIG. 21. In some embodiments, the solvate is a potassium salt THF solvate.

In some embodiments, the solvate is a Diethylamine salt solvate. In some embodiments, the Diethylamine salt solvate is characterized by an x-ray powder diffraction pattern that is substantially as set forth in FIG. 20. In some embodiments, the solvate is a Diethylamine salt toluene solvate.

III. Pharmaceutical Compositions

One aspect of the present disclosure relates to pharmaceutical compositions comprising a crystalline form of Compound 1. Another aspect of the present disclosure relates to pharmaceutical compositions comprising a crystalline form of a solvate of Compound 1.

One aspect of the present disclosure relates to pharmaceutical compositions comprising a pharmaceutically acceptable salt of Compound 1. Another aspect of the present disclosure relates to pharmaceutical compositions comprising a solvate of a pharmaceutically acceptable salt of Compound 1.

One aspect of the present disclosure relates to pharmaceutical compositions comprising a crystalline form of a pharmaceutically acceptable salt of Compound 1. Another aspect of the present disclosure relates to pharmaceutical compositions comprising a crystalline form of a solvate of a pharmaceutically acceptable salt of Compound 1.

The pharmaceutical compositions herein comprise a therapeutically effective amount of any of the compounds in Section II for treating or preventing a disease, condition, and/or disorder. A therapeutically effective amount may vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy. Appropriate concentrations and dosages can be determined by one skilled in the art.

In some embodiments, the dosage of compound 1 is in the range of from about 1 mg/kg to 24 mg/kg, although a lower or higher dosage also may be administered as circumstances dictate. A dosage of 1-20 mg/kg for a 70 kg patient, for example, is 70-1,400 mg. The dosage may be repeated as needed, for example, once per week for 4-10 weeks, once per week for 8 weeks, or once per week for 4 weeks. It may also be given less frequently, such as every other week for several months, or monthly or quarterly for many months, as needed in a maintenance therapy. In some embodiments, dosage is 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, 20 mg/kg, 22 mg/kg, 24 mg/kg, 26 mg/kg, 28 mg/kg, 30 mg/kg, 35 mg/kg, 40 mg/kg, 45 mg/kg, 50 mg/kg, 55 mg/kg, 65 mg/kg, 70 mg/kg, 75 mg/kg, 80 mg/kg, 85 mg/kg, 90 mg/kg, 95 mg/kg, 100 mg/kg, 120 mg/kg, 140 mg/kg, 160 mg/kg, 180 mg/kg, 200 mg/kg, 220 mg/kg, 240 mg/kg, 260 mg/kg, 280 mg/kg, 300 mg/kg, 350 mg/kg, 400 mg/kg, 450 mg/kg, 500 mg/kg, 550 mg/kg, 600 mg/kg, 650 mg/kg, 700 mg/kg, 750 mg/kg, or 800 mg/kg.

In some embodiments, the compound is present in the pharmaceutical composition in an amount from about 5 mg to about 1000 mg. In some embodiments, the compound is present in the pharmaceutical composition in an amount of about 5 mg to about 300 mg. In some embodiments, the compound is present in the pharmaceutical composition in an amount of about 5 mg to about 200 mg. In some embodiments, the compound is present in the pharmaceutical composition in an amount of about 5 mg to about 100 mg. In some embodiments, the compound is present in the pharmaceutical composition in an amount of about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, about 120 mg, about 125 mg, about 130 mg, about 135 mg, about 140 mg, about 145 mg, about 150 mg, about 155 mg, about 160 mg, about 165 mg, about 170 mg, about 175 mg, about 180 mg, about 185 mg, about 190 mg, about 195 mg, about 200 mg, about 300 mg, about 400 mg, about 500 mg, or about 1000 mg.

In some embodiments, the compound is present in the pharmaceutical composition in an amount of about 5 mg. In some embodiments, the compound is present in the pharmaceutical composition in an amount of about 15 mg. In some embodiments, the compound is present in the pharmaceutical composition in an amount of about 25 mg. In some embodiments, the compound is present in the pharmaceutical composition in an amount of about 50 mg.

In some embodiments, the compound is administered in a 21-day cycle with 2 days dosing followed by 5 days off. In some embodiments, the compound is administered on days 1, 2, 8, 9, 15 and 16 of each 21-day cycle for up to 105 weeks.

In some embodiments, the compound is administered once per week, 1 day dosing followed by 6 days off. In some embodiments, the compound is administered twice every three weeks.

The pharmaceutical compositions disclosed herein can be prepared by combining a compound disclosed herein with an appropriate pharmaceutically acceptable carrier or excipient, and may be formulated into preparations in solid, semi solid, liquid or gaseous forms, such as tablets, capsules, powders, granules, ointments, solutions, suppositories, injections, inhalants, gels, microspheres, and aerosols. In some embodiments, pharmaceutical compositions disclosed herein are formulated into preparations in tablets or capsules.

The pharmaceutical compositions disclosed herein may be prepared by methodology well known in the pharmaceutical art. For example, a solid pharmaceutical composition intended for oral administration can be prepared by mixing a compound disclosed herein with at least one pharmaceutical carrier or excipient to form a solid preformulation composition, which then may be readily subdivided into equally effective unit dosage forms such as tablets, pills and capsules. Methods of preparing dosage forms are known, or will be apparent, to those skilled in this art; for example, see Remington: The Science and Practice of Pharmacy, 20th Edition (Philadelphia College of Pharmacy and Science, 2000). In some embodiments, the composition is in the form of a unit dosage form. In some embodiments, the unit dosage form is a tablet.

In some embodiments, the pharmaceutical compositions disclosed herein further comprises at least one additional therapeutic compound. In some embodiments, the at least one additional therapeutic compound is a drug used to treat cancer. In some embodiments, the at least one additional therapeutic compound is chosen from docetaxel, sacituzumab govitecan, and gemcitabine.

The pharmaceutical compositions disclosed herein may be formulated so as to allow the active ingredients contained therein to be bioavailable upon administration of the composition to a patient. Typical routes of administering such pharmaceutical compositions include, without limitation, oral, topical, transdermal, inhalation, parenteral, sublingual, buccal, rectal, vaginal, and intranasal. In some embodiments, the pharmaceutical compositions are prepared for oral administration.

In some embodiments, the pharmaceutical compositions disclosed herein are administered with at least one additional therapeutic compound. The administration of the at least one additional therapeutic compound may occur before, after or at the same time as a pharmaceutical composition disclosed herein is being administered. In some embodiments, the at least one additional therapeutic compound is a drug used to treat cancer. In some embodiments, the at least one additional therapeutic compound is chosen from docetaxel, sacituzumab govitecan, and gemcitabine.

IV. Methods and Uses

One aspect of the present disclosure relates to methods and uses of any of the compounds and pharmaceutical compositions disclosed herein.

In one aspect, the present disclosure relates to a method of inhibiting MCL-1 in a patient comprising administering to the patient any of the compounds or pharmaceutical compositions disclosed herein.

In some embodiments, the method of inhibiting MCL-1 in a patient comprises administering to the patient a crystalline form of Compound 1 and/or a crystalline form of a pharmaceutically acceptable salt of Compound 1. In some embodiments, the method of inhibiting MCL-1 in a patient comprises administering to the patient a pharmaceutical composition crystalline form of Compound 1 and/or the crystalline form of a pharmaceutically acceptable salt of Compound 1, and a pharmaceutically acceptable carrier or excipient.

In one aspect, the present disclosure relates to a method of treating cancer in a patient comprising administering to the patient any of the compounds or pharmaceutical compositions disclosed herein.

In some embodiments, the method of treating cancer in a patient comprises administering to the patient a crystalline form of Compound 1 and/or a crystalline form of a pharmaceutically acceptable salt of Compound 1. In some embodiments, the method of treating cancer in a patient comprises administering to the patient a pharmaceutical composition crystalline form of Compound 1 and/or the crystalline form of a pharmaceutically acceptable salt of Compound 1, and a pharmaceutically acceptable carrier or excipient.

In one aspect, the present disclosure relates to a use of any of the compounds or pharmaceutical compositions disclosed herein for treating cancer. In some embodiments, the compound is a crystalline form of Compound 1 and/or a crystalline form of a pharmaceutically acceptable salt of Compound 1. In some embodiments, the pharmaceutical composition crystalline form of Compound 1 and/or the crystalline form of a pharmaceutically acceptable salt of Compound 1, and a pharmaceutically acceptable carrier or excipient.

In one aspect, the present disclosure relates to a use of any of the compounds or pharmaceutical compositions disclosed in herein for the manufacture of a medicament for treating cancer. In some embodiments, the compound is a crystalline form of Compound 1 and/or a crystalline form of a pharmaceutically acceptable salt of Compound 1. In some embodiments, the pharmaceutical composition crystalline form of Compound 1 and/or the crystalline form of a pharmaceutically acceptable salt of Compound 1, and a pharmaceutically acceptable carrier or excipient.

In some embodiments, in any of the above methods or uses, the cancer is a hematologic malignancy. In some embodiments, the cancer is relapsed refractory multiple myeloma or relapsed refractory myeloma. In some embodiments, the cancer is a solid malignancy. In some embodiments, the cancer is triple-negative breast cancer, colorectal cancer, skin cancer, melanoma, ovarian cancer, kidney cancer, small cell lung cancer, non-small cell lung cancer, lymphoma, leukemia, or metastatic soft-tissue sarcoma.

In one aspect, the present disclosure relates any of the compounds or pharmaceutical compositions disclosed herein for use in a method of treating cancer. In some embodiments, the compound is a crystalline form of Compound 1 and/or a crystalline form of a pharmaceutically acceptable salt of Compound 1. In some embodiments, the pharmaceutical composition crystalline form of Compound 1 and/or the crystalline form of a pharmaceutically acceptable salt of Compound 1, and a pharmaceutically acceptable carrier or excipient.

In some embodiments, the cancer is a hematologic malignancy. In some embodiments, the cancer is relapsed refractory multiple myeloma or relapsed refractory myeloma. In some embodiments, the cancer is triple-negative breast cancer, colorectal cancer, skin cancer, melanoma, ovarian cancer, kidney cancer, small cell lung cancer, non-small cell lung cancer, lymphoma, leukemia, or metastatic soft-tissue sarcoma. In some embodiments, the cancer is a solid malignancy.

In some embodiments, in any of the above methods or uses, the method further comprises administering an additional therapeutic compound to the patient. In some embodiments, the additional therapeutic compound is selected from docetaxel, sacituzumab govitecan, and gemcitabine.

ENUMERATED EMBODIMENTS

Embodiment 1: A crystalline form of Compound 1:

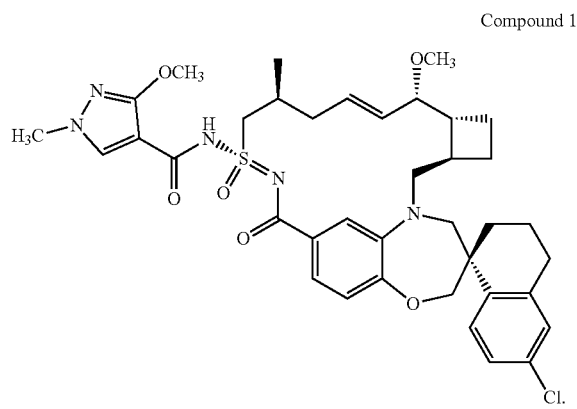 [SMILES: COc1nn(C)cc1C(=O)N[S@@]1(=O)=NC(=O)c2ccc3c(c2)N(C[C@@H]2CC[C@H]2[C@@H](OC)/C=C/C[C@H](C)C1)C[C@@]1(CCCc2cc(Cl)ccc21)CO3]

Compound 1

Embodiment 2: The crystalline form according to Embodiment 1, wherein the crystalline form of Compound 1 is Form I.

Embodiment 3: The crystalline form according to Embodiment 1 or Embodiment 2, wherein the crystalline form of Compound 1 is characterized by an x-ray powder diffraction pattern comprising peaks at about 4.9°±0.2°, 8.6°±0.2° and 14.3°±0.2° 2-θ.

Embodiment 4: The crystalline form according to Embodiment 3, wherein the x-ray powder diffraction pattern comprises one or more additional peaks selected from peaks at about 16.2°±0.2°, 18.3°±0.2° and 22.1°±0.2° 2-θ.

Embodiment 5: The crystalline form according to Embodiment 3 or Embodiment 4, wherein the x-ray powder diffraction pattern comprises one or more additional peaks selected from peaks at about 17.8°±0.2°, 19.3°±0.2° and 21.5°±0.2° 2-θ.

Embodiment 6: The crystalline form according to Embodiment 5, wherein the x-ray powder diffraction pattern comprises one or more additional peaks selected from peaks at about 13.5°±0.2°, 14.6°±0.2°, 16.0°±0.2°, 17.5°±0.2°, 18.8°±0.2°, 20.2°±0.2°, 20.7° 0.2°, 23.0°±0.2°, 24.6°±0.2°, 26.3°±0.2° and 26.8°±0.2° 2-θ.

Embodiment 7: The crystalline form according to any one of Embodiments 1-6, wherein the crystalline form of Compound 1 is characterized by an x-ray powder diffraction pattern that is substantially as set forth in FIG. 31.

Embodiment 8: The crystalline form according to any one of Embodiments 2-7, wherein Form I is characterized by having a differential scanning calorimetry thermogram comprising an endothermic peak with onset at about 180° C.

Embodiment 9: The crystalline form according to Embodiment 8, wherein the differential scanning calorimetry thermogram is substantially as set forth in FIG. 32.

Embodiment 10: The crystalline form according to any one of Embodiments 2-9, wherein Form I is characterized by having a thermogravimetric analysis thermogram showing a weight loss of about 1.0% over a temperature of from ambient temperature to about 170° C.

Embodiment 11: The crystalline form according to Embodiment 10, wherein the thermogravimetric analysis thermogram is substantially as set forth in FIG. 33.

Embodiment 12: The crystalline form according to any one of Embodiments 2-11, wherein Form I is characterized by absorbing about 1.4 wt % water at about 25° C. and between about 0% and 90% relative humidity.

Embodiment 13: The crystalline form according to any one of Embodiments 2-12, wherein Form I is characterized by having a dynamic vapor sorption mass uptake profile substantially as set forth in FIG. 34.

Embodiment 14: The crystalline form according to Embodiment 1, wherein the crystalline form of Compound 1 is Form II.

Embodiment 15: The crystalline form according to Embodiment 1 or Embodiment 14, wherein the crystalline form of Compound 1 is characterized by an x-ray powder diffraction pattern comprising peaks at about 6.1°±0.2°, 15.7°±0.2° and 16.1°±0.2° 2-θ.

Embodiment 16: The crystalline form according to Embodiment 15, wherein the x-ray powder diffraction pattern comprises one or more additional peaks selected from peaks at about 15.4°±0.2°, 16.9°±0.2° and 19.9°±0.2° 2-θ.

Embodiment 17: The crystalline form according to Embodiment 15 or Embodiment 16, wherein the x-ray powder diffraction pattern comprises one or more additional peaks selected from peaks at about 12.8°±0.2°, 13.9°±0.2° and 22.8°±0.2° 2-θ.

Embodiment 18: The crystalline form according to Embodiment 17, wherein the x-ray powder diffraction pattern comprises one or more additional peaks selected from peaks at about 10.5°±0.2°, 12.2°±0.2°, 13.3°±0.2°, 18.2°±0.2°, 19.0°±0.2°, 19.4°±0.2°, 20.3°±0.20, 21.10±0.20, 23.4°±0.2°, 25.2°±0.2°, 25.7°±0.2°, 26.7°±0.2° and 27.9°±0.20° 2-θ.

Embodiment 19: The crystalline form according to any one of Embodiments 1 or 14-18, wherein the crystalline form of Compound 1 is characterized by an x-ray powder diffraction pattern that is substantially as set forth in FIG. 36.

Embodiment 20: The crystalline form according to any one of Embodiments 14-19, wherein Form II is characterized by having a differential scanning calorimetry thermogram comprising an endothermic peak with onset at about 163° C.

Embodiment 21: The crystalline form according to Embodiment 20, wherein the differential scanning calorimetry thermogram is substantially as set forth in FIG. 37.

Embodiment 22: The crystalline form according to any one of Embodiments 14-21, wherein Form II is characterized by having a thermogravimetric analysis thermogram showing a weight loss of about 0.6% over a temperature of from ambient temperature to about 210° C.

Embodiment 23: The crystalline form according to Embodiment 22, wherein the thermogravimetric analysis thermogram is substantially as set forth in FIG. 38.

Embodiment 24: The crystalline form according to any one of Embodiments 14-23, wherein Form II is characterized by absorbing up to about 1.1 wt % water between about 0% and 90% relative humidity at about 25° C.

Embodiment 25: The crystalline form according to any one of Embodiments 14-24, wherein Form II is characterized by having a dynamic vapor sorption mass uptake profile substantially as set forth in FIG. 39.

Embodiment 26: The crystalline form according to Embodiment 1, wherein the crystalline form of Compound 1 is Form III.

Embodiment 27: The crystalline form according to Embodiment 1 or Embodiment 26, wherein the crystalline form of Compound 1 is characterized by an x-ray powder diffraction pattern comprising peaks at about 8.0°±0.2°, 15.0°±0.2° and 18.4°±0.2° 2-θ.

Embodiment 28: The crystalline form according to Embodiment 27, wherein the x-ray powder diffraction pattern comprises one or more additional peaks selected from peaks at about 16.5°±0.2°, 22.1°±0.2° and 22.9°±0.2° 2-θ.

Embodiment 29: The crystalline form according to Embodiment 27 or Embodiment 28, wherein the x-ray powder diffraction pattern comprises one or more additional peaks selected from peaks at about 12.5°±0.2°, 19.5°±0.2° and 23.6°±0.2° 2-θ.

Embodiment 30: The crystalline form according to Embodiment 29, wherein the x-ray powder diffraction pattern comprises one or more additional peaks selected from peaks at about 6.5°±0.2°, 12.3°±0.2°, 12.9°±0.2°, 13.6°±0.2°, 14.3°±0.2°, 16.0°±0.2°, 18.1°±0.20, 20.70±0.20, 24.10±0.20, 24.70±0.20, 26.80±0.20 and 28.30±0.20° 2-θ.

Embodiment 31: The crystalline form according to any one of Embodiments 1 or 26-30, wherein the crystalline form of Compound 1 is characterized by an x-ray powder diffraction pattern that is substantially as set forth in FIG. 40.

Embodiment 32: The crystalline form according to any one of Embodiments 26-31, wherein Form III is characterized by having a differential scanning calorimetry thermogram comprising at least one endothermic peak selected from peaks with onset at about 20° C., 133° C. and 153° C.

Embodiment 33: The crystalline form according to Embodiment 32, wherein the differential scanning calorimetry thermogram is substantially as set forth in FIG. 41.

Embodiment 34: The crystalline form according to any one of Embodiments 26-33, wherein Form III is characterized by having a thermogravimetric analysis thermogram showing a weight loss of about 2.9% over a temperature of from about ambient temperature to about 90° C.

Embodiment 35: The crystalline form according to any one of Embodiments 26-34, wherein Form III is characterized by having a thermogravimetric analysis thermogram showing a weight loss of about 1.1% over a temperature of from about 90° C. to about 175° C.

Embodiment 36: The crystalline form according to any one of Embodiments 26-35, wherein Form III is characterized by having a thermogravimetric analysis thermogram showing a weight loss of about 1.6% over a temperature of from about 175° C. to about 225° C.

Embodiment 37: The crystalline form according to any one of Embodiments 34-36, wherein the thermogravimetric analysis thermogram is substantially as set forth in FIG. 42.

Embodiment 38: The crystalline form according to any one of Embodiments 26-37, wherein Form III is characterized by absorbing up to about 5 wt % water between about 0% and 90% relative humidity at about 25° C.

Embodiment 39: The crystalline form according to any one of Embodiments 26-38, wherein Form III is characterized by having a dynamic vapor sorption mass uptake profile substantially as set forth in FIG. 43.

Embodiment 40: The crystalline form according to Embodiment 1, wherein the crystalline form of Compound 1 is Form IV.

Embodiment 41: The crystalline form according to Embodiment 1 or Embodiment 40, wherein the crystalline form of Compound 1 is characterized by an x-ray powder diffraction pattern comprising peaks at about 7.1°±0 2° 8.7°±0.2° and 10.6°±0.2° 2-θ.

Embodiment 42: The crystalline form according to Embodiment 41, wherein the x-ray powder diffraction pattern comprises one or more additional peaks selected from peaks at about 10.3°±0.2°, 11.2°±0.2° and 18.2°±0.2° 2-θ.

Embodiment 43: The crystalline form according to Embodiment 41 or Embodiment 42, wherein the x-ray powder diffraction pattern comprises one or more additional peaks selected from peaks at about 14.2°±0.2°, 20.5°±0.2° and 24.9°±0.2° 2-θ.

Embodiment 44: The crystalline form according to Embodiment 43, wherein the x-ray powder diffraction pattern comprises one or more additional peaks selected from peaks at about 3.3°±0.2°, 13.2°±0.2°, 15.4°±0.2°, 16.2°±0.2°, 17.9°±0.2°, 19.0°±0.2°, 21.3°±0.20, 21.90±0.20, 23.30±0.20, 26.10±0.20 and 28.30±0.2° 2-θ.

Embodiment 45: The crystalline form according to any one of Embodiments 1 or 40-41, wherein the crystalline form of Compound 1 is characterized by an x-ray powder diffraction pattern that is substantially as set forth in FIG. 44.

Embodiment 46: The crystalline form according to any one of Embodiments 40-45, wherein Form IV is characterized by having a differential scanning calorimetry thermogram comprising at least one endothermic peak selected from peaks with onset at about 119° C. and 166° C.

Embodiment 47: The crystalline form according to Embodiment 46, wherein the differential scanning calorimetry thermogram is substantially as set forth in FIG. 45.

Embodiment 48: The crystalline form according to any one of Embodiments 40-47, wherein Form IV is characterized by having a thermogravimetric analysis thermogram showing a weight loss of about 0.6% over a temperature of from ambient temperature to about 200° C.

Embodiment 49: The crystalline form according to Embodiment 48, wherein the thermogravimetric analysis thermogram is substantially as set forth in FIG. 46.

Embodiment 50: A crystalline form of a pharmaceutically acceptable salt of Compound 1:

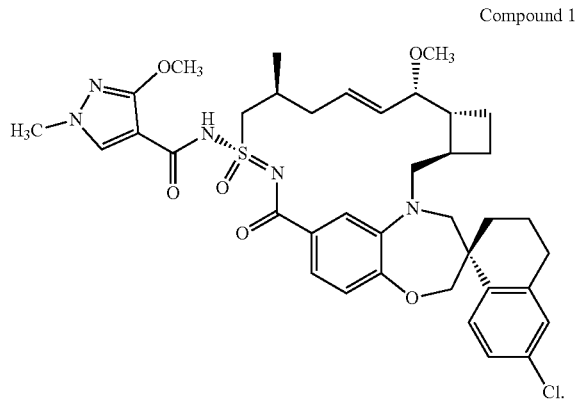 [SMILES: COc1nn(C)cc1C(=O)N[S@@]1(=O)=NC(=O)c2ccc3c(c2)N(C[C@@H]2CC[C@H]2[C@@H](OC)/C=C/C[C@H](C)C1)C[C@@]1(CCCc2cc(Cl)ccc21)CO3]

Compound 1

Embodiment 51: The crystalline form according to Embodiment 50, wherein the pharmaceutically acceptable salt of Compound 1 is a sodium salt.

Embodiment 52: The crystalline form according to Embodiment 51, wherein the sodium salt is Na Salt Form 1.

Embodiment 53: The crystalline form according to Embodiment 51 or Embodiment 52, wherein the sodium salt of Compound 1 is characterized by an x-ray powder diffraction pattern comprising peaks at about 7.6°±0.2°, 8.4°±0.2° and 12.8°±0.2° 2-θ.

Embodiment 54: The crystalline form according to Embodiment 53, wherein the x-ray powder diffraction pattern comprises one or more additional peaks selected from peaks at about 15.3°±0.2°, 18.4°±0.2° and 20.4°±0.2° 2-θ.

Embodiment 55: The crystalline form according to Embodiment 53 or Embodiment 54, wherein the x-ray powder diffraction pattern comprises one or more additional peaks selected from peaks at about 12.3°±0.2°, 13.4°±0.2° and 24.0°±0.2° 2-θ.

Embodiment 56: The crystalline form according to Embodiment 55, wherein the x-ray powder diffraction pattern comprises one or more additional peaks selected from peaks at about 6.7°±0.2°, 13.7°±0.2°, 14.0°±0.2°, 15.7°±0.2°, 17.1°±0.2°, 17.4°±0.2°, 17.9°±0.20, 19.20±0.20, 22.00±0.20, 22.20±0.20, 23.60±0.20, 24.30±0.20 and 24.80±0.2° 2-θ.

Embodiment 57: The crystalline form according to any one of Embodiments 50-56, wherein the pharmaceutically acceptable salt of Compound 1 is characterized by an x-ray powder diffraction pattern that is substantially as set forth in FIG. 1.

Embodiment 58: The crystalline form according to any one of Embodiments 52-57, wherein the Na Salt Form 1 is characterized by having a differential scanning calorimetry thermogram comprising at least one endothermic peak selected from peaks with onset at about 14° C., 83° C. and 232° C.

Embodiment 59: The crystalline form according to according to Embodiment 58, wherein the differential scanning calorimetry thermogram is substantially as set forth in FIG. 2.

Embodiment 60: The crystalline form according to any one of Embodiments 52-59, wherein the Na Salt Form 1 is characterized by having a thermogravimetric analysis thermogram showing a weight loss of about 4.2% over a temperature of from ambient temperature to about 200° C.

Embodiment 61: The crystalline form according to Embodiment 60, wherein the thermogravimetric analysis thermogram is substantially as set forth in FIG. 3.

Embodiment 62: The crystalline form according to any one of Embodiments 52-61, wherein the Na Salt Form 1 is characterized by absorbing about 7.5 wt % water between about 0% and 90% relative humidity at about 25° C.

Embodiment 63: The crystalline form according to any one of Embodiments 52-62, wherein the Na Salt Form 1 is characterized by having a dynamic vapor sorption mass uptake profile substantially as set forth in FIG. 4.

Embodiment 64: The crystalline form according to Embodiment 51, wherein the sodium salt of Compound 1 is Na Salt Form 2.

Embodiment 65: The crystalline form according to Embodiment 51 or Embodiment 64, wherein the sodium salt of Compound 1 is characterized by an x-ray powder diffraction pattern comprising peaks at about 7.2°±0.2°, 14.7°±0.2° and 19.3°±0.2° 2-θ.

Embodiment 66: The crystalline form according to Embodiment 65, wherein the x-ray powder diffraction pattern comprises one or more additional peaks selected from peaks at about 11.1°±0.2°, 17.1°±0.2° and 20.7°±0.2° 2-θ.

Embodiment 67: The crystalline form according to Embodiment 65 or Embodiment 66, wherein the x-ray powder diffraction pattern comprises one or more additional peaks selected from peaks at about 13.1°±0.2°, 14.5°±0.2° and 16.9°±0.2° 2-θ.

Embodiment 68: The crystalline form according to Embodiment 67, wherein the x-ray powder diffraction pattern comprises one or more additional peaks selected from peaks at about 6.7°±0.2°, 9.1±0.2, 9.7°±0.2°, 12.1°±0.2°, 15.2°±0.2°, 17.3°±0.2°, 17.5°±0.2°, 17.80±0.20, 18.20±0.20, 19.10±0.20, 21.60±0.20, 22.00±0.20, 22.80±0.20, 24.40±0.20 and 25.10±0.2° 2-θ.

Embodiment 69: The crystalline form according to any one of Embodiments 50-52 or 64-68, wherein the pharmaceutically acceptable salt of Compound 1 is characterized by an x-ray powder diffraction pattern that is substantially as set forth in FIG. 5.

Embodiment 70: The crystalline form according to any one of Embodiments 64-69, wherein the Na Salt Form 2 is characterized by having a differential scanning calorimetry thermogram comprising at least one endothermic peak selected from peaks with onset at about 21° C. and 224° C.

Embodiment 71: The crystalline form according to any one of Embodiments 64-70, wherein the Na Salt Form 2 is characterized by having a differential scanning calorimetry thermogram comprising an exothermic peak with onset at about 109° C.

Embodiment 72: The crystalline form according to according to Embodiment 70 or Embodiment 71, wherein the differential scanning calorimetry thermogram is substantially as set forth in FIG. 6.

Embodiment 73: The crystalline form according to any one of Embodiments 64-72, wherein the Na Salt Form 2 is characterized by having a thermogravimetric analysis thermogram showing a weight loss of about 4.8% over a temperature of from ambient temperature to about 200° C.

Embodiment 74: The crystalline form according to Embodiment 73, wherein the thermogravimetric analysis thermogram is substantially as set forth in FIG. 7.

Embodiment 75: The crystalline form according to Embodiment 51, wherein the sodium salt is Na Salt Form 3.

Embodiment 76: The crystalline form according to Embodiment 51 or Embodiment 75, wherein the sodium salt of Compound 1 is characterized by an x-ray powder diffraction pattern comprising peaks at about 4.1°±0.2°, 13.2°±0.2° and 18.8°±0.2° 2-θ.

Embodiment 77: The crystalline form according to Embodiment 76, wherein the x-ray powder diffraction pattern comprises one or more additional peaks selected from peaks at about 12.1°±0.2°, 20.0°±0.2° and 24.2°±0.2° 2-θ.

Embodiment 78: The crystalline form according to Embodiment 76 or Embodiment 77, wherein the x-ray powder diffraction pattern comprises one or more additional peaks selected from peaks at about 14.8°±0.2°, 20.9°±0.2° and 22.9°±0.2° 2-θ.

Embodiment 79: The crystalline form according to Embodiment 78, wherein the x-ray powder diffraction pattern comprises one additional peak at about 8.2°±0.2° 2-θ.

Embodiment 80: The crystalline form according to any one of Embodiments 50-51 or 75-79, wherein the pharmaceutically acceptable salt of Compound 1 is characterized by an x-ray powder diffraction pattern that is substantially as set forth in FIG. 8.

Embodiment 81: The crystalline form according to any one of Embodiments 75-80, wherein the Na Salt Form 3 is characterized by having a differential scanning calorimetry thermogram comprising at least one endothermic peak selected from peaks with onset at about 19° C. and 219° C.

Embodiment 82: The crystalline form according to according to Embodiment 81, wherein the differential scanning calorimetry thermogram is substantially as set forth in FIG. 9.

Embodiment 83: The crystalline form according to any one of Embodiments 75-82, wherein the Na Salt Form 3 is characterized by having a thermogravimetric analysis thermogram showing a weight loss of about 5.1% over a temperature of from ambient temperature to about 200° C.

Embodiment 84: The crystalline form according to Embodiment 83, wherein the thermogravimetric analysis thermogram is substantially as set forth in FIG. 10.

Embodiment 85: The crystalline form according to Embodiment 51, wherein the sodium salt is Na Salt Form 4.

Embodiment 86: The crystalline form according to Embodiment 51 or Embodiment 85, wherein the sodium salt of Compound 1 is characterized by an x-ray powder diffraction pattern comprising peaks at about 6.7°±0.2°, 13.3°±0.2° and 20.2°±0.2° 2-θ.

Embodiment 87: The crystalline form according to Embodiment 86, wherein the x-ray powder diffraction pattern comprises one or more additional peaks selected from peaks at about 16.0°±0.2°, 21.0°±0.2° and 23.4°±0.2° 2-θ.

Embodiment 88: The crystalline form according to Embodiment 87, wherein the x-ray powder diffraction pattern comprises one or more additional peaks selected from peaks at about 7.2°±0.2°, 21.5°±0.2° and 22.8°±0.2° 2-θ.

Embodiment 89: The crystalline form according to Embodiment 87 or Embodiment 88, wherein the x-ray powder diffraction pattern comprises one or more additional peaks selected from peaks at about 7.5°±0.2°, 8.3°±0.2°, 9.4°±0.2°, 11.9°±0.2°, 12.8°±0.20, 14.80±0.20, 15.50±0.20, 16.50±0.20, 16.80±0.20, 18.20±0.20, 18.90±0.20, 24.20±0.20, 25.90±0.20 and 26.80±0.2° 2-θ.

Embodiment 90: The crystalline form according to any one of Embodiments 50-51 or 85-89, wherein the pharmaceutically acceptable salt of Compound 1 is characterized by an x-ray powder diffraction pattern that is substantially as set forth in FIG. 11.

Embodiment 91: The crystalline form according to Embodiment 51, wherein the sodium salt is Na Salt Form 5.

Embodiment 92: The crystalline form according to Embodiment 51 or Embodiment 91, wherein the sodium salt of Compound 1 is characterized by an x-ray powder diffraction pattern comprising peaks at about 7.6°±0.2°, 13.9°±0.2° and 15.4°±0.2° 2-θ.

Embodiment 93: The crystalline form according to Embodiment 92, wherein the x-ray powder diffraction pattern comprises one or more additional peaks selected from peaks at about 6.0°±0.2°, 8.9°±0.2° and 12.1°±0.2° 2-θ.

Embodiment 94: The crystalline form according to Embodiment 92 or Embodiment 93, wherein the x-ray powder diffraction pattern comprises one or more additional peaks selected from peaks at about 17.0°±0.2°, 21.7°±0.2° and 23.0°±0.2° 2-θ.

Embodiment 95: The crystalline form according to Embodiment 94, wherein the x-ray powder diffraction pattern comprises one or more additional peaks selected from peaks at about 5.2°±0.2°, 12.7°±0.2°, 14.5°±0.2°, 17.3°±0.2°, 17.7°±0.2°, 18.6°±0.2°, 18.9°±0.20, 19.70±0.20, 20.20±0.20, 22.10±0.20, 22.40±0.20, 23.50±0.20, 24.30±0.20, 25.40±0.20, 28.00±0.20, 29.50±0.20 and 37.20±0.2° 2-θ.

Embodiment 96: The crystalline form according to any one of Embodiments 50-51 and 91-95, wherein the pharmaceutically acceptable salt of Compound 1 is characterized by an x-ray powder diffraction pattern that is substantially as set forth in FIG. 12.

Embodiment 97: The crystalline form according to any one of Embodiments 91-96, wherein the Na Salt Form 5 is characterized by having a differential scanning calorimetry thermogram comprising at least one endothermic peak selected from peaks with onset at about 29° C. and 143° C.

Embodiment 98: The crystalline form according to any one of Embodiments 91-97, wherein the Na Salt Form 5 is characterized by having a differential scanning calorimetry thermogram comprising an exothermic peak with onset at about 198° C.

Embodiment 99: The crystalline form according to according to Embodiment 97 or Embodiment 98, wherein the differential scanning calorimetry thermogram is substantially as set forth in FIG. 13.

Embodiment 100: The crystalline form according to any one of Embodiments 91-99, wherein the Na Salt Form 5 is characterized by having a thermogravimetric analysis thermogram showing a weight loss of about 4.2% over a temperature of from ambient temperature to about 200° C.

Embodiment 101: The crystalline form according to Embodiment 100, wherein the thermogravimetric analysis thermogram showing is substantially as set forth in FIG. 14.

Embodiment 102: The crystalline form according to Embodiment 50, wherein the pharmaceutically acceptable salt of Compound 1 is a potassium salt.

Embodiment 103: The crystalline form according to Embodiment 102, wherein the potassium salt is K Salt Form 1.

Embodiment 104: The crystalline form according to Embodiment 102 or Embodiment 103, wherein the potassium salt of the Compound 1 is characterized by an x-ray powder diffraction pattern comprising peaks at about 7.6°±0.2° 8.2°±0.2° and 12.7°±0.2° 2-θ.

Embodiment 105: The crystalline form according to Embodiment 104, wherein the x-ray powder diffraction pattern comprises one or more additional peaks selected from peaks at about 13.4°±0.2°, 18.2°±0.2° and 21.9°±0.2° 2-θ.

Embodiment 106: The crystalline form according to Embodiment 104 or Embodiment 105, wherein the x-ray powder diffraction pattern comprises one or more additional peaks selected from peaks at about 12.3°±0.2°, 15.3°±0.2° and 20.1°±0.2° 2-θ.

Embodiment 107: The crystalline form according to Embodiment 106, wherein the x-ray powder diffraction pattern comprises one or more additional peaks selected from peaks at about 6.7°±0.2°, 9.3°±0.2°, 11.1°±0.2°, 13.7°±0.2°, 14.0°±0.2°, 16.2°±0.2°, 17.1°±0.2°, 17.7°±0.2°, 19.2°±0.2°, 22.2°±0.2°, 23.5°±0.2°, 24.1°±0.2° and 24.7°±0.2° 2-θ.

Embodiment 108: The crystalline form according to any one of Embodiments 50 or 102-107, wherein the pharmaceutically acceptable salt of Compound 1 is characterized by an x-ray powder diffraction pattern that is substantially as set forth in FIG. 15.

Embodiment 109: The crystalline form according to any one of Embodiments 103-108, wherein the K Salt Form 1 is characterized by having a differential scanning calorimetry thermogram comprising at least one endothermic peak selected from peaks with onset at about 14° C., 182° C. and 233° C.

Embodiment 110: The crystalline form according to according to Embodiment 109, wherein the differential scanning calorimetry thermogram is substantially as set forth in FIG. 17.

Embodiment 111: The crystalline form according to any one of Embodiments 103-110, wherein the K Salt Form 1 is characterized by having a thermogravimetric analysis thermogram showing a weight loss of about 4.2% over a temperature of from ambient temperature to about 200° C.

Embodiment 112: The crystalline form according to Embodiment 111, wherein the thermogravimetric analysis thermogram is substantially as set forth in FIG. 18.

Embodiment 113: The crystalline form according to any one of Embodiments 103-112, wherein the K Salt Form 1 is characterized by absorbing about 11 wt % water between about 0% and 90% relative humidity at about 25° C.

Embodiment 114: The crystalline form according to any one of Embodiments 103-113, wherein the K Salt Form 1 is characterized by having a dynamic vapor sorption mass uptake profile substantially as set forth in FIG. 19.

Embodiment 115: The crystalline form according to Embodiment 50, wherein the pharmaceutically acceptable salt of Compound 1 is a diethylamine salt.

Embodiment 116: The crystalline form according to Embodiment 115, wherein the diethylamine salt of is Diethylamine Salt Form 1.

Embodiment 117: The crystalline form according to Embodiment 115 or Embodiment 116, wherein the diethylamine salt of Compound 1 is characterized by an x-ray powder diffraction pattern comprising peaks at about 9.0°±0.2°, 9.5°±0.2° and 12.7°±0.2° 2-θ.

Embodiment 118: The crystalline form according to Embodiment 117, wherein the x-ray powder diffraction pattern comprises one or more additional peaks selected from peaks at about 6.2°±0.2°, 12.5°±0.2° and 13.1°±0.2° 2-θ.

Embodiment 119: The crystalline form according to Embodiment 117 or Embodiment 118, wherein the x-ray powder diffraction pattern comprises one or more additional peaks selected from peaks at about 4.3°±0.2°, 14.1°±0.2° and 17.0°±0.2° 2-θ.

Embodiment 120: The crystalline form according to Embodiment 119, wherein the x-ray powder diffraction pattern comprises one or more additional peaks selected from peaks at about 5.20±0.20, 8.50±0.20, 10.50±0.20, 16.10±0.20, 19.50±0.20, 21.10±0.20 and 26.40±0.20 2-θ.

Embodiment 121: The crystalline form according to any one of Embodiments 50 or 115-120, wherein the pharmaceutically acceptable salt of Compound 1 is characterized by an x-ray powder diffraction pattern that is substantially as set forth in FIG. 23.

Embodiment 122: The crystalline form according to any one of Embodiments 116-121, wherein the Diethylamine Salt Form 1 is characterized by having a differential scanning calorimetry thermogram comprising at least one endothermic peak selected from peaks with onset at about 17° C. and 145° C.

Embodiment 123: The crystalline form according to according to Embodiment 122, wherein the differential scanning calorimetry thermogram is substantially as set forth in FIG. 24.

Embodiment 124: The crystalline form according to any one of Embodiments 116-123, wherein the Diethylamine Salt Form 1 is characterized by having a thermogravimetric analysis thermogram showing a weight loss of about 8.4% over a temperature of from ambient temperature to about 170° C.

Embodiment 125: The crystalline form according to Embodiment 124, wherein the thermogravimetric analysis thermogram is substantially as set forth in FIG. 25.

Embodiment 126: The crystalline form according to any one of Embodiments 116-125, wherein the Diethylamine Salt Form 1 is characterized by absorbing about 5.5 wt % water between about 0% and 90% relative humidity at about 25° C.

Embodiment 127: The crystalline form according to any one of Embodiments 116-126, wherein the Diethylamine Salt Form 1 is characterized by having a dynamic vapor sorption mass uptake profile substantially as set forth in FIG. 26.

Embodiment 128: The crystalline form according to Embodiment 50, wherein the pharmaceutically acceptable salt of Compound 1 is a choline salt.

Embodiment 129: The crystalline form according to Embodiment 128, wherein the choline salt is Choline Salt Form 1.

Embodiment 130: The crystalline form according to Embodiment 128 or Embodiment 129, wherein the choline salt of Compound 1 is characterized by an x-ray powder diffraction pattern comprising peaks at about 10.4°±0.2°, 20.9°±0.2° and 22.9°±0.2° 2-θ.

Embodiment 131: The crystalline form according to Embodiment 130, wherein the x-ray powder diffraction pattern comprises one or more additional peaks selected from peaks at about 14.0°±0.2°, 15.7°±0.2° and 24.0°±0.2° 2-θ.

Embodiment 132: The crystalline form according to Embodiment 130 or Embodiment 131, wherein the x-ray powder diffraction pattern comprises one or more additional peaks selected from peaks at about 14.4°±0.2°, 16.8°±0.2° and 25.1°±0.2° 2-θ.

Embodiment 133: The crystalline form according to Embodiment 132, wherein the x-ray powder diffraction pattern comprises one or more additional peaks selected from peaks at about 4.8°±0.2°, 11.0°±0.2°, 11.4°±0.2°, 13.2°±0.2°, 15.6°±0.2°, 16.1°±0.2°, 17.2°±0.2°, 18.2°±0.2°, 18.9°±0.2°, 19.4°±0.2°, 20.2°±0.2°, 27.0°±0.2° and 28.0°±0.2° 2-θ.

Embodiment 134: The crystalline form according to any one of Embodiments 50 or 128-133, wherein the pharmaceutically acceptable salt of Compound 1 is characterized by an x-ray powder diffraction pattern that is substantially as set forth in FIG. 27.

Embodiment 135: The crystalline form according to any one of Embodiments 129-134, wherein the Choline Salt Form 1 is characterized by having a differential scanning calorimetry thermogram comprising at least one endothermic peak selected from peaks with onset at about 23° C., 99° C. and 156° C.

Embodiment 136: The crystalline form according to according to Embodiment 135, wherein the differential scanning calorimetry thermogram is substantially as set forth in FIG. 28.

Embodiment 137: The crystalline form according to any one of Embodiments 129-136, wherein the Choline Salt Form 1 is characterized by having a thermogravimetric analysis thermogram showing a weight loss of about 8.8% over a temperature of from ambient temperature to about 200° C.

Embodiment 138: The crystalline form according to Embodiment 128, wherein the thermogravimetric analysis thermogram is substantially as set forth in FIG. 29.

Embodiment 139: A pharmaceutical composition comprising the crystalline form of Compound 1 according to any of Embodiments 1-49 or the crystalline form of a pharmaceutically acceptable salt of Compound 1 according to any one of claims 50-138 and a pharmaceutically acceptable carrier or excipient.

Embodiment 140: The pharmaceutical composition according to Embodiment 139, wherein the composition is in the form of a unit dosage form.

Embodiment 141: The pharmaceutical composition according to Embodiment 140, wherein the unit dosage form is a tablet.

Embodiment 142: A method for inhibiting MCL-1 in a patient comprising administering to the patient the crystalline form of Compound 1 according to any of Embodiments 1-49 or the crystalline form of a pharmaceutically acceptable salt of Compound 1 according to any one of Embodiments 50-138 or the pharmaceutical composition according to any one of Embodiments 139-141.

Embodiment 143: A method for treating cancer in a patient comprising administering to the patient the crystalline form of Compound 1 according to any of Embodiments 1-49 or the crystalline form of a pharmaceutically acceptable salt of Compound 1 according to any one of Embodiments 50-138 or the pharmaceutical composition according to any one of Embodiments 139-141.

Embodiment 144: Use of a crystalline form of Compound 1 according to any of Embodiments 1-49 or the crystalline form of a pharmaceutically acceptable salt of Compound 1 according to any one of Embodiments 50-138 or the pharmaceutical composition according to any one of Embodiments 139-141 for treating cancer.

Embodiment 145: Use of a crystalline form of Compound 1 according to any of Embodiments 1-49 or the crystalline form of a pharmaceutically acceptable salt of Compound 1 according to any one of Embodiments 50-138 or the pharmaceutical composition according to any one of Embodiments 139-141 for the manufacture of a medicament for treating cancer.

Embodiment 146: The method or use according to any one of Embodiments 143-145, wherein the cancer is a hematologic malignancy.

Embodiment 147: The method or use according to any one of Embodiments 143-145, wherein the cancer is relapsed refractory multiple myeloma or relapsed refractory myeloma.

Embodiment 148: The method or use according to any one of Embodiments 143-145, wherein the cancer is a solid malignancy.

Embodiment 149: The method or use according to any one of Embodiments 143-145, wherein the cancer is triple-negative breast cancer, colorectal cancer, skin cancer, melanoma, ovarian cancer, kidney cancer, small cell lung cancer, non-small cell lung cancer, lymphoma, leukemia, or metastatic soft-tissue sarcoma.

Embodiment 150: The method or use according to any one of Embodiments 142-149, wherein the method further comprises administering an additional therapeutic compound to the patient.

Embodiment 151: The method according to Embodiment 150, wherein the additional therapeutic compounds is selected from docetaxel, sacituzumab govitecan, and gemcitabine.

Embodiment 152: A crystalline form of Compound 1 according to any of Embodiments 1-49 or the crystalline form of a pharmaceutically acceptable salt of Compound 1 according to any one of Embodiments 50-138 or the pharmaceutical composition according to any one of Embodiments 139-141 for use in a method of treating cancer.

Embodiment 153: The crystalline form of Embodiment 152, wherein the cancer is a hematologic malignancy.

Embodiment 154: The crystalline form of Embodiment 152, wherein the cancer is relapsed refractory multiple myeloma or relapsed refractory myeloma.

Embodiment 155: The crystalline form of Embodiment 152, wherein the cancer is triple-negative breast cancer, colorectal cancer, skin cancer, melanoma, ovarian cancer, kidney cancer, small cell lung cancer, non-small cell lung cancer, lymphoma, leukemia, or metastatic soft-tissue sarcoma.

Embodiment 156: The crystalline form of Embodiment 152, wherein the cancer is a solid malignancy.

Embodiment 157: The crystalline form of any one of Embodiments 152-156, wherein the method further comprises administering an additional therapeutic compound to the patient.

Embodiment 158: The crystalline form of Embodiment 157, wherein the additional therapeutic compounds is selected from docetaxel, sacituzumab govitecan, and gemcitabine.

Embodiment 159: The crystalline form of Compound 1 according to any one of Embodiments 2-13, prepared by a process comprising: (1) contacting Compound 1 or a salt thereof with a solvent chosen from acetone, ethyl acetate, an alcohol, methyl ethyl ketone, methyl isobutyl ketone, tetrahydrofuran, dichloromethane, and di-butyl ether and mixtures of such solvents; and (2) isolating the solid product.

Embodiment 160: The crystalline form according to Embodiment 159, wherein the solvent comprises acetone.

Embodiment 161: The crystalline form according to Embodiment 159 or 160, wherein the process further comprises heating the mixture of Compound 1 or a salt thereof and the solvent.

Embodiment 162: The crystalline form according to any one of Embodiments 159-161, wherein the process further comprises drying the solid product.

Embodiment 163: The crystalline form according to any one of Embodiments 159-162, wherein the process further comprises washing and/or crystallizing the solid product with a second solvent chosen from acetone, ethyl acetate, an alcohol or a mixture of such solvents and optionally drying.

Embodiment 164: The crystalline form of Compound 1 according to any one of Embodiments 2-13, prepared by a process comprising: (1) contacting Compound 1 or a salt thereof with a buffer to produce a mixture; (2) adding a solvent chosen from acetonitrile and an acetonitrile/water mix to the mixture to create a slurry; (3) mixing the slurry; and (4) isolating the solid product.

Embodiment 165: The crystalline form according to Embodiment 164, wherein the pH of the buffer is about 2.

Embodiment 166: The crystalline form of Compound 1 according to any one of Embodiments 2-13, prepared by a process comprising: (1) contacting Form II according to claims 14-25, Form III according to claims 26-39, or Form IV according to claims 40-49, or a salt thereof, with an alcohol; and (2) isolating the solid product.

Embodiment 167: The crystalline form of Compound 1 according to any one of Embodiments 159-163 or 166, wherein the alcohol is chosen from ethanol and isopropyl alcohol.

Embodiment 168: The crystalline form of Compound 1 according to any one of Embodiments 159-163 or 166-167, wherein the alcohol is ethanol.

EXAMPLES

Equipment: The following equipment was used to study the salts and polymorphs in the examples below.

X-ray powder diffraction (XRPD) analysis was conducted on a diffractometer (PANalytical XPERT-PRO, PANalytical B. V., Almelo, Netherlands) using copper radiation (Cu Kα, λ=1.541874). Samples were spread evenly on a zero-background sample plate. The generator was operated at a voltage of 45 kV and amperage of 40 mA. Slits were Soller 0.02 rad, antiscatter 1.0°, and divergence. Scans were performed from 2 to 40° 2–θ with a 0.0167 step size. Data analysis was performed using X'Pert Data Viewer V1.2d (PANalytical B.V., Almelo, Netherlands).

Differential Scanning Calorimetry (DSC) was run on a Q2000 (TA Instruments, New Castle, DE) by loading 1-5 mg of material into a capped (with or without a pin hole) Tzero standard aluminum pan and heating the sample at 10° C./min from −20 to 250° C. or above. The sample and reference pans were under a 50 mL/min nitrogen purge. Data analysis was completed using Universal Analysis 2000 Version 4.5A (TA Instruments, New Castle, DE).

Thermogravimetric analysis (TGA) was used to evaluate sample weight loss as a function of temperature on either a Q5000 or Q500 (TA Instruments, New Castle, DE), by loading 1-10 mg of material onto a weigh pan and heating the sample to 350° C. at a rate of 10° C./min. The sample and reference pans were under a 60 mL/min and 40 mL/min nitrogen purge, respectively. Data analysis was completed using Universal Analysis 2000 Version 4.5A (TA Instruments, New Castle, DE).

Thermogravimetric analysis with Mass Spectrometry (TA Discovery Series TGA and MS) was used to determine what was associated with the sample weight loss as a function of temperature (TA Instruments, New Castle). A sample (~2-5 mg) was placed in a platinum pan and heated up to 350° C. at a heating rate of 10-20° C./min. The sample and reference pans were under a 25 mL/min and 10 mL/min nitrogen purge, respectively. Data analysis was completed using TA Instruments Trios Software v. 4.0 (TA Instruments, New Castle, DE).

Hygroscopicity was studied using dynamic vapor sorption (DVS, TA Q5000 SA, TA Instruments, New Castle, DE or DVS, DVS Intrinsic, Surface Measurement Systems, London, UK). A sample (2-20 mg) was placed in an aluminum DVS pan and loaded on the sample side of the twin pan balance. The water sorption and desorption were studied as a function of relative humidity (RH) at 25° C. In 10% RH increments, the relative humidity was increased from 40% RH to 90% RH and then decreased back to 0%, followed by repeating the full cycle from 0% RH up to 90% RH and back to 0% RH. Each relative humidity increment had an equilibration time of 180 minutes, unless weight change % was less than 0.002% in 30 minutes. Data analysis was performed using Universal Analysis 2000 Version 4.5A (TA Instruments, New Castle, DE) for TA DVS runs and Microsoft Excel for SMS DVS runs.

Proton Nuclear Magnetic Resonance ($^1$H NMR) spectra were collected on a Varian 400-MR 400 MHz instrument with 7620AS sample changer. The default proton parameters are as follows: spectral width: 14 to −2 ppm (6397.4 Hz); relaxation delay: 1 sec; pulse: 45 degrees; acquisition time: 2.049 sec; number of scans or repetitions: 8; temperature: 25 C. Samples were prepared in dimethyl sulfoxide-d6, unless otherwise stated. Off-line analysis was carried out using MNova software.

Amounts: All amounts provided in the examples below should be understood to be "about" the exact number listed, whether or not the word "about" is explicitly recited. For example, "600 mg" as well as "about 600 mg" should be understood to be mean "about 600 mg".

Example 1. Salt Study of Compound 1

A salt study was performed on Compound 1 as described below.

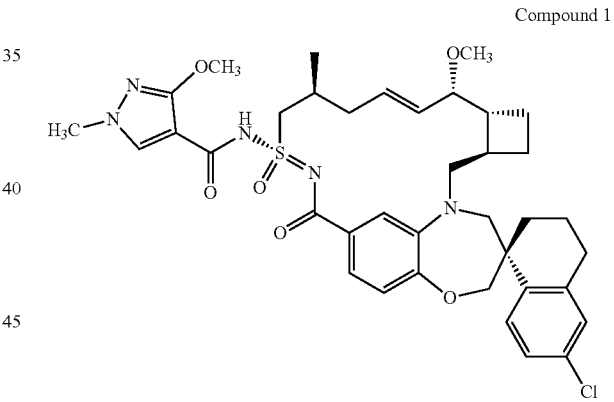

Compound 1

More specifically, a salt study was conducted on Compound 1 using the following basic co-formers: NaOH, KOH, choline hydroxide, t-butylamine, TRIS, meglumine, L-lysine, benzathine, and diethylamine. Only four crystalline salts of Compound 1 were obtained: sodium salt, potassium salt, diethylamine salt, and choline salt. A co-crystal study with 9 acids (oxalic, fumaric, citric, adipic, glutaric, succinic, malic, mandelic, and glycolic acids) did not afford any crystalline material.

A. Sodium Salt—Overview

A sodium salt of Compound 1 was initially obtained during sodium bicarbonate wash of a Compound 1 reaction mixture. Studies on the Na salt using about 25 organic solvents afforded four desolvated forms (Form 1, Form 2, Form 3, and Form 4) as well as multiple potential solvates with the following solvents: MeCN, EtOH, IPA, acetone, THF, DCM, DMF, DMAc/water, and BuCN. All solvated forms appeared to be labile and desolvated upon drying.

Sodium salt Form 1 was also obtained from polymorph Form I of Compound 1 (discussed below) using NaOH.

B. Sodium Salt of Compound 1—Form 1 ("Na Salt Form 1")

Form 1 of the sodium salt of Compound 1 is a desolvated/dehydrated form initially obtained during sodium bicarbonate wash of the Compound 1 reaction mixture. More specifically, the crude reaction mixture of Compound 1 in DCM described in Example 154 of PCT publication WO 2019/222112 was concentrated in vacuo. The remaining material was partitioned between ethyl acetate (about 300 mL) and saturated aqueous ammonium chloride (about 40 mL). The organic phase was washed twice with saturated aqueous ammonium chloride (about 40 mL each), then once with saturated aqueous sodium bicarbonate (about 40 mL), then once with brine (about 40 mL). The organic phase was dried over sodium sulfate, filtered, and concentrated in vacuo to a crude brown solid.

The crude solid was azeotroped once with dichloromethane (about 30 mL), then suspended in acetonitrile (about 270 mL) and N,N-dimethylformamide (about 5 mL). The resulting mixture was warmed to about 80° C. for about 1 h, then filtered to collect the undissolved solid, washing with acetonitrile. The resulting cake was dried under air, then further dried in a vacuum oven at about 50° C. for about 4 days to afford 6.72 g of Na Salt Form 1. The XRPD pattern is shown in FIG. 1 and is characterized by sharp reflections, indicating crystallinity. Table 1a below lists the characteristic peaks. Table 1b shows extended peak list. It was observed that Na salt Form 1 tends to retain some residual solvents and water after drying.

TABLE 1a

Characteristic peaks of Na Salt Form 1

| Pos. [°2 Th.] | Rel. Int. [%] |
|---|---|
| 7.6 | 100 |
| 8.4 | 88 |
| 12.8 | 62 |
| 15.3 | 48 |
| 18.4 | 53 |
| 20.4 | 53 |
| 12.3 | 36 |
| 13.4 | 41 |
| 24.0 | 44 |

TABLE 1b

Extended peak list of Na Salt Form 1

| Pos. [°2 Th.] | Rel. Int. [%] |
|---|---|
| 6.7 | 27 |
| 7.6 | 100 |
| 8.4 | 88 |
| 12.3 | 36 |
| 12.8 | 62 |
| 13.4 | 41 |
| 13.7 | 35 |
| 14.0 | 34 |
| 15.3 | 48 |
| 15.7 | 24 |
| 17.1 | 23 |
| 17.4 | 27 |
| 17.9 | 22 |
| 18.4 | 53 |
| 19.2 | 28 |
| 20.4 | 53 |
| 22.0 | 34 |
| 22.2 | 22 |
| 23.6 | 31 |

TABLE 1b-continued

Extended peak list of Na Salt Form 1

| Pos. [°2 Th.] | Rel. Int. [%] |
|---|---|
| 24.0 | 44 |
| 24.3 | 26 |
| 24.8 | 27 |

Figure 2:
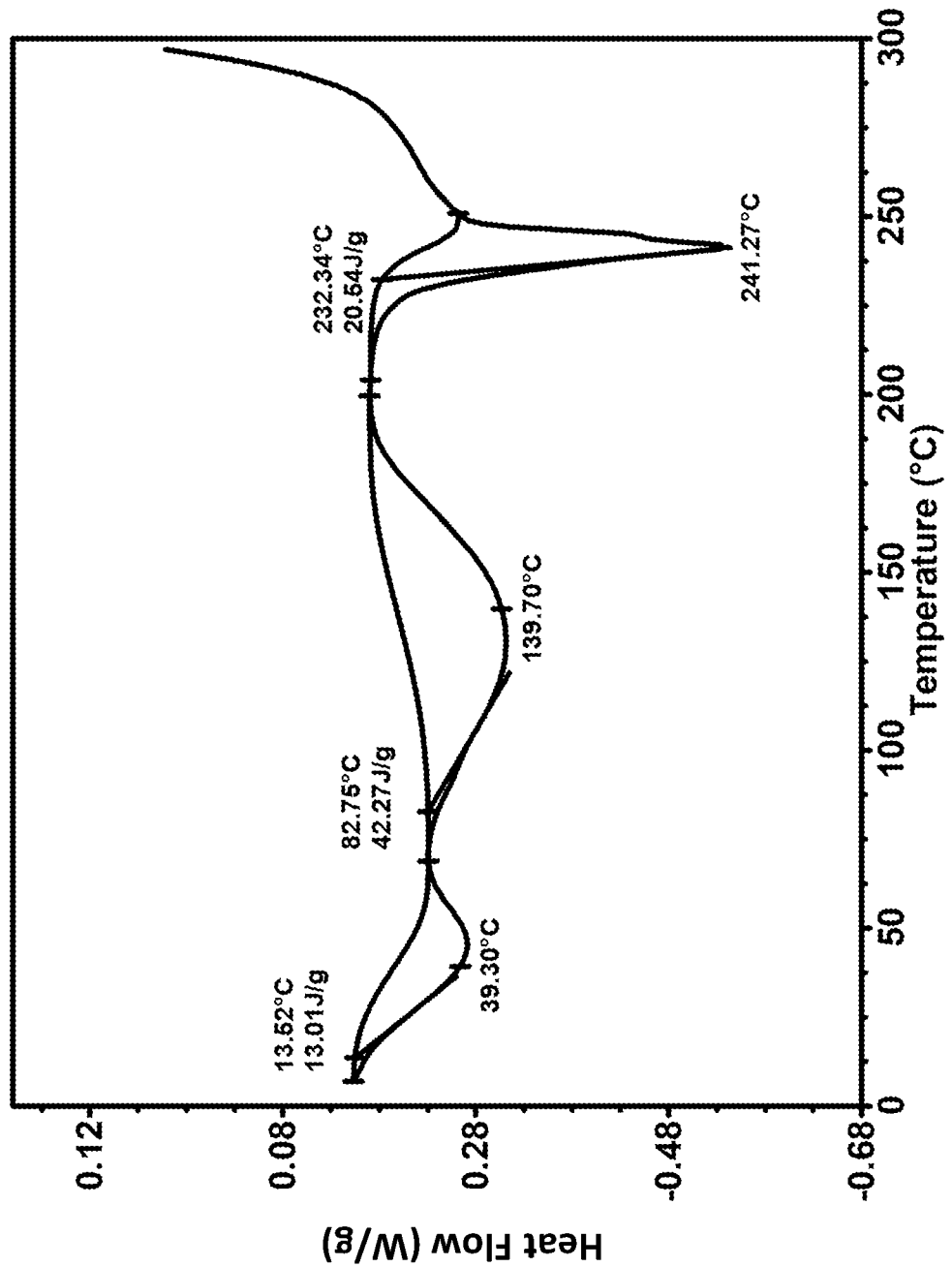
FIG. 2 provides a DSC thermogram for Na Salt Form 1.
Figure 3:
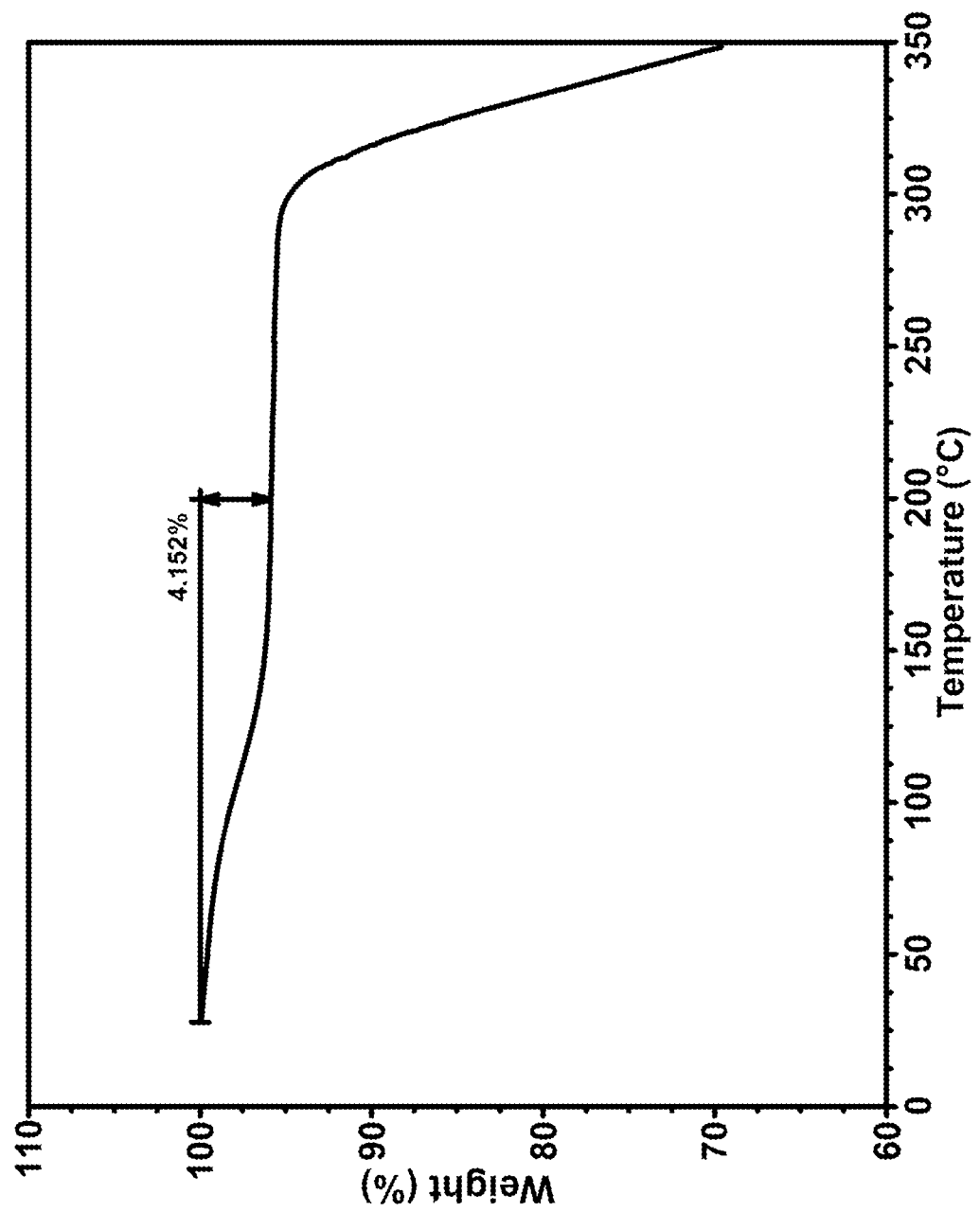
FIG. 3 provides a TGA thermogram for Na Salt Form 1.
Figure 4:
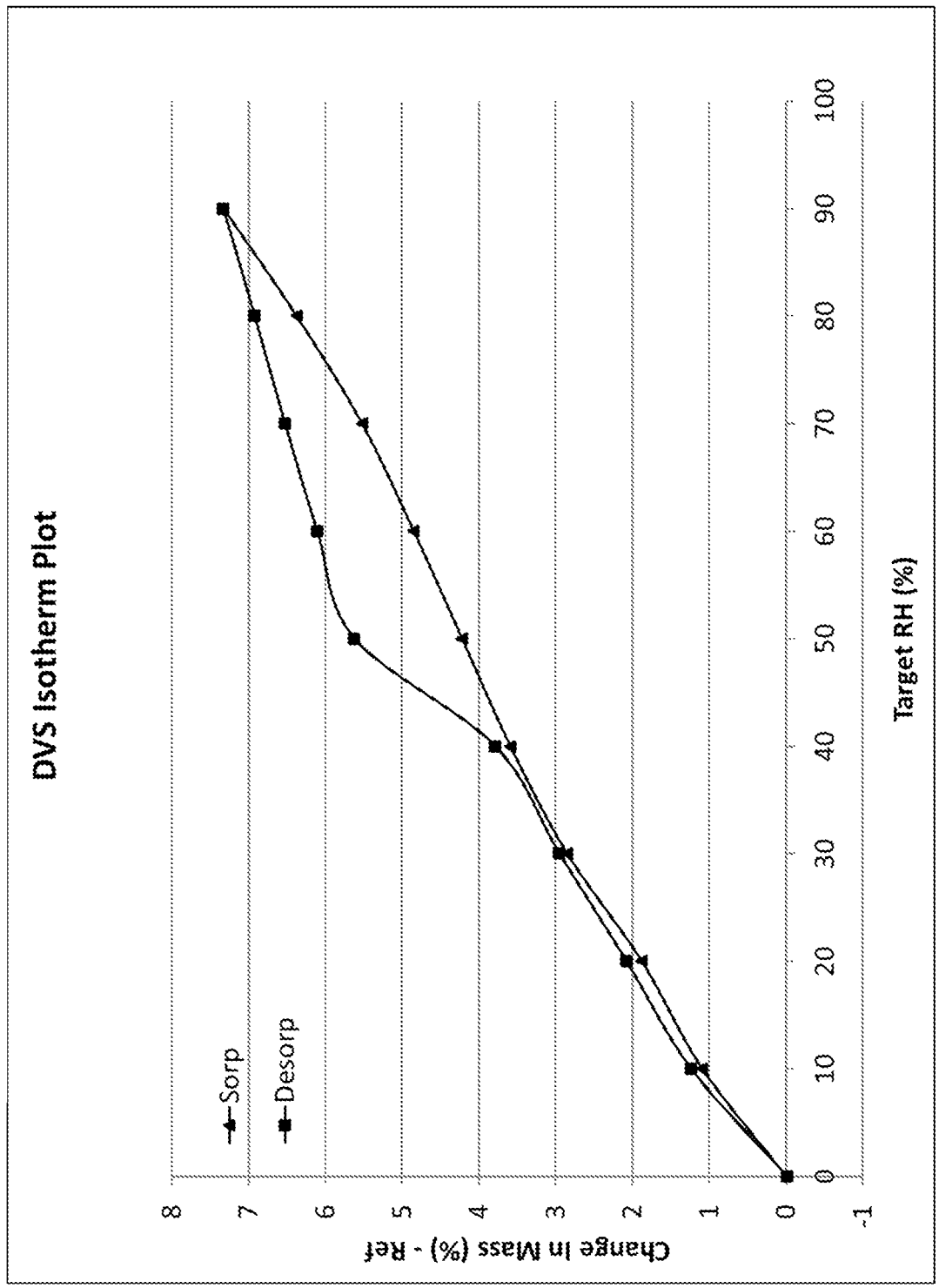
FIG. 4 provides a DVS analysis for Na Salt Form 1.

The DSC thermogram of Na salt Form 1 is shown in FIG. 2. The DSC data shows two broad endothermic events with onset temperatures at about 14° C. and at about 83° C. attributed to the loss of water and residual solvent, followed by third endothermic event with an onset temperature at about 232° C. attributed to the melt of the salt. The TGA thermogram of Na salt Form 1 is shown in FIG. 3. The TGA weight loss of about 4.2 wt % observed from ambient temperature to about 200° C. corresponds to the loss of water (about 2.2 wt % by KF) and residual MeCN (about 0.5 eq. by NMR). DVS analysis of Na salt Form 1 is shown in FIG. 4 and indicates that Na salt Form 1 is moderately hygroscopic and absorbs about 7.5 wt % moisture between 0% and 90% RH and at about 25° C. XRPD analysis of the sample post DVS showed no form change.

C. Sodium Salt of Compound 1—Form 2 ("Na Salt Form 2")

Figure 5:
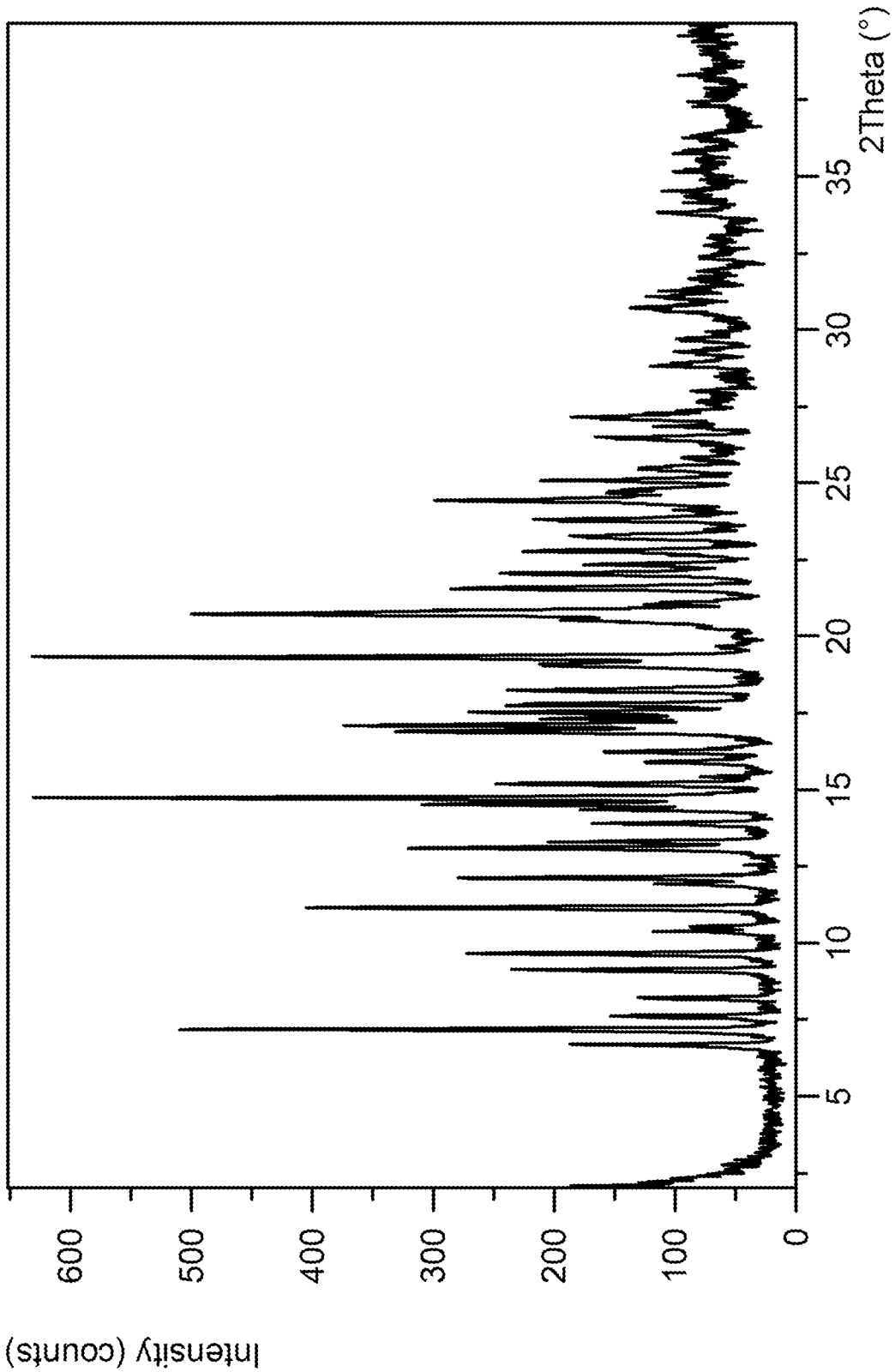
FIG. 5 provides an XRPD pattern for Na Salt Form 2.

Na salt Form 2 was obtained by slurrying Na salt Form 1 with dichloromethane and then drying the DCM solvate at about 50° C. The XRPD pattern of Na salt Form 2 is shown in FIG. 5, and is characterized by sharp reflections, indicating crystallinity. Table 2a shows characteristic peaks of Na salt Form 2. Table 2b shows extended peak list of Na salt Form 2.

TABLE 2a

Characteristic peaks of Na Salt Form 2

| Pos. [°2 Th.] | Rel. Int. [%] |
|---|---|
| 7.2 | 76 |
| 14.7 | 100 |
| 19.3 | 92 |
| 11.1 | 63 |
| 17.1 | 56 |
| 20.7 | 73 |
| 13.1 | 47 |
| 14.5 | 44 |
| 16.9 | 50 |

TABLE 2b

Extended peak list of Na Salt Form 2

| Pos. [°2 Th.] | Rel. Int. [%] |
|---|---|
| 6.7 | 28 |
| 7.2 | 76 |
| 9.1 | 32 |
| 9.7 | 41 |
| 11.1 | 63 |
| 12.1 | 41 |
| 13.1 | 47 |
| 14.5 | 44 |
| 14.7 | 100 |
| 15.2 | 34 |
| 16.9 | 50 |
| 17.1 | 56 |
| 17.3 | 28 |
| 17.5 | 39 |
| 17.8 | 31 |
| 18.2 | 30 |

TABLE 2b-continued

Extended peak list of Na Salt Form 2

| Pos. [°2 Th.] | Rel. Int. [%] |
|---|---|
| 19.1 | 29 |
| 19.3 | 92 |
| 20.7 | 73 |
| 21.6 | 38 |
| 22.0 | 31 |
| 22.8 | 26 |
| 24.4 | 37 |
| 25.1 | 25 |

Figure 6:
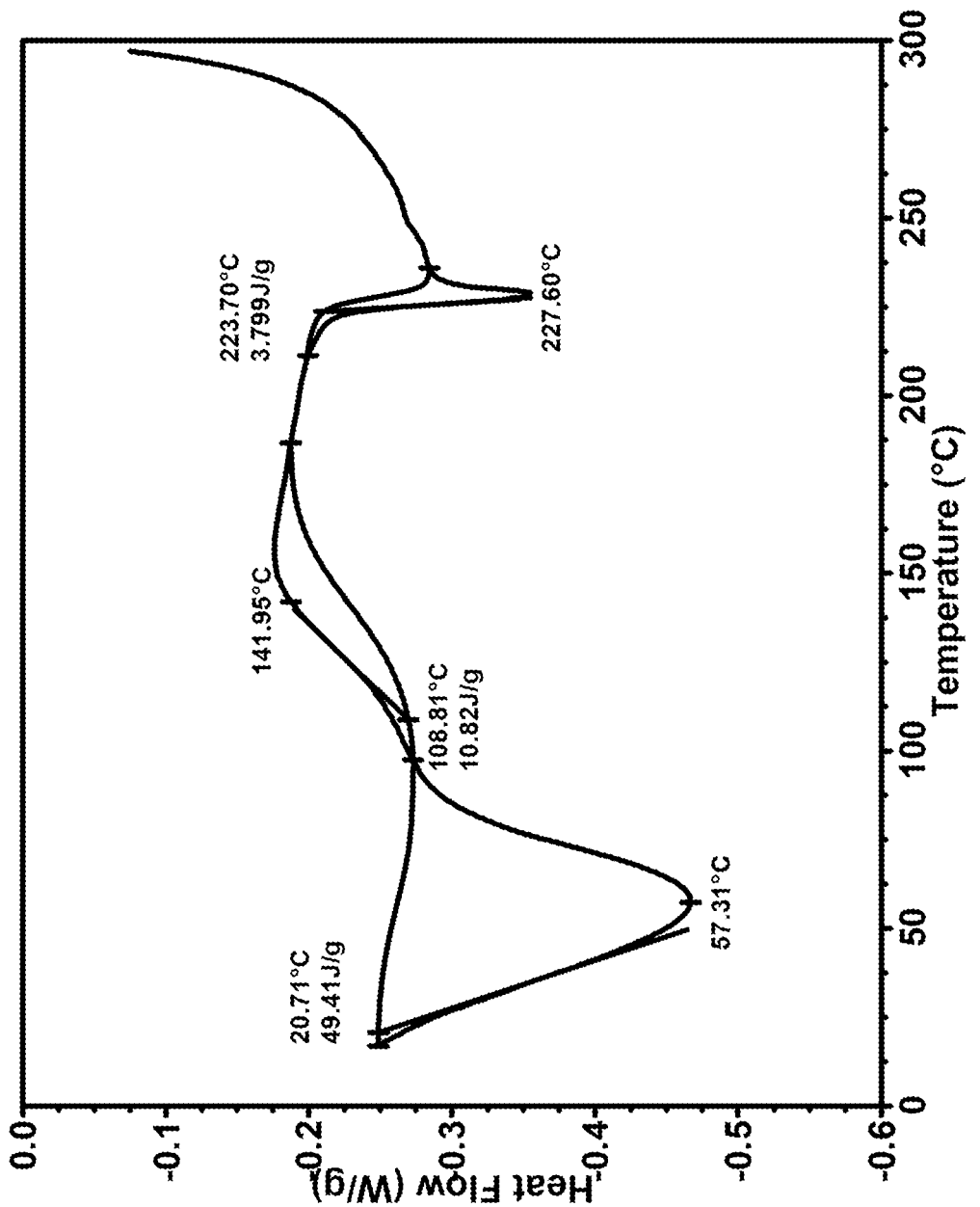
FIG. 6 provides a DSC thermogram for Na Salt Form 2.
Figure 7:
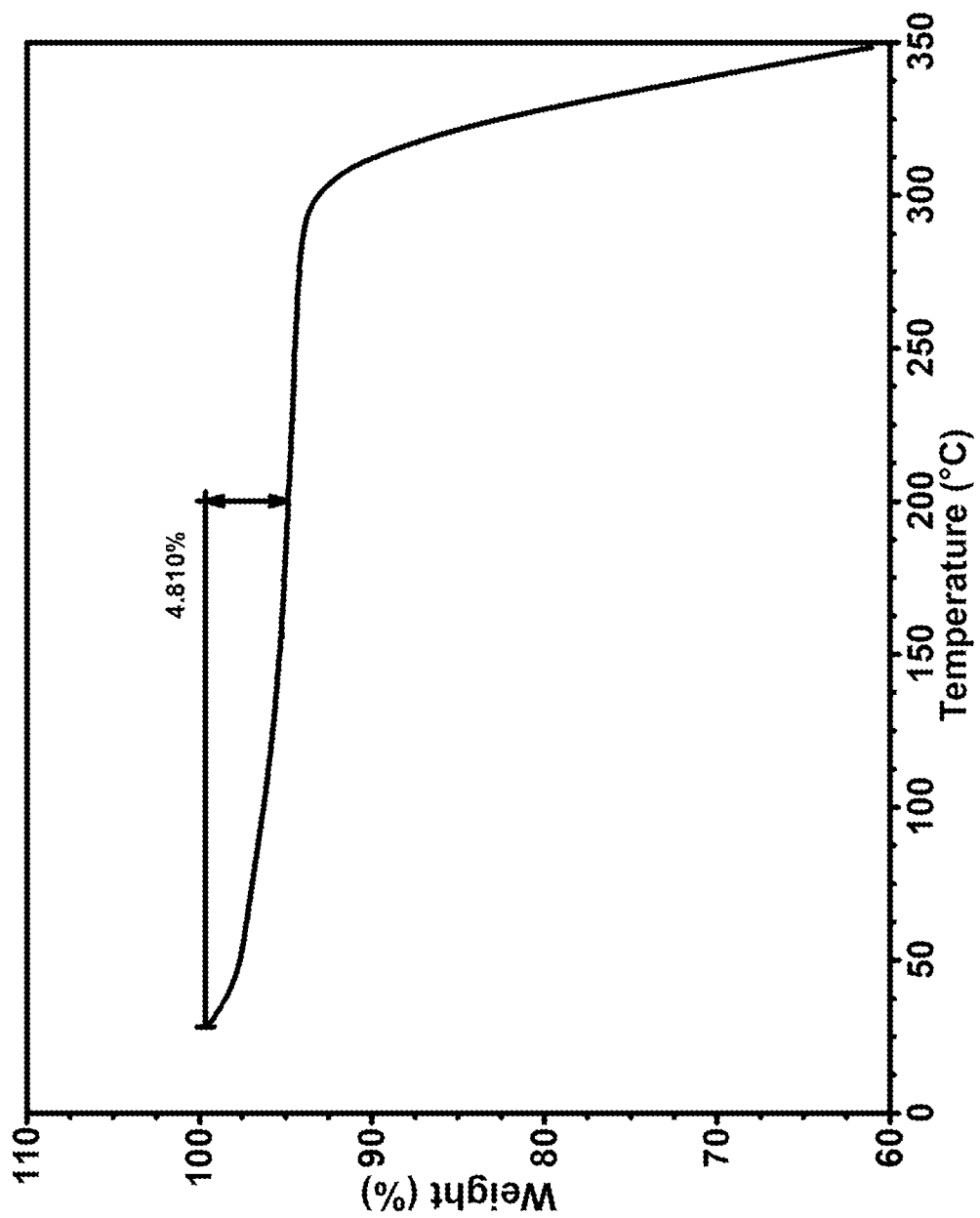
FIG. 7 provides a TGA thermogram for Na Salt Form 2.

The DSC thermogram of Na salt Form 2 is shown in FIG. 6. The DSC data shows broad endothermic event with onset temperature at about 21° C., followed by broad exothermic event with onset temperature at about 109° C., and then endothermic event with an onset temperature at about 224° C. attributed to the melt of the salt. The TGA thermogram of Na salt Form 2 is shown in FIG. 7. The TGA continuous weight loss of about 4.8 wt % observed from ambient temperature up to about 200° C. most likely corresponds to the loss of surface water.

D. Sodium Salt of Compound 1—Form 3 ("Na Salt Form 3")

Figure 8:
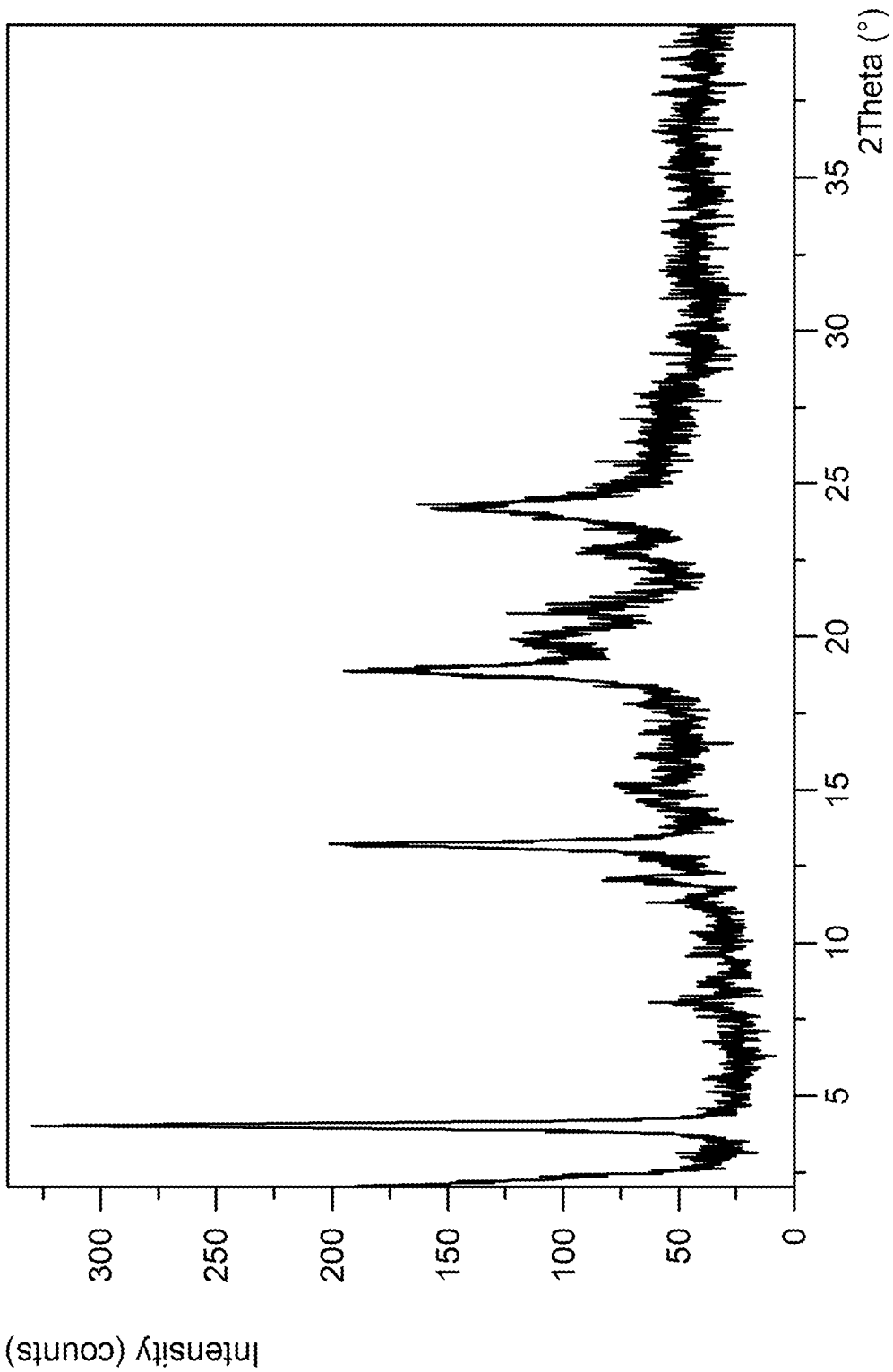
FIG. 8 provides an XRPD pattern for Na Salt Form 3.

Na salt Form 3 was obtained by slurrying Na salt Form 1 with isopropanol and then drying the IPA solvate at about 50° C. The XRPD pattern of Na salt Form 3 is shown in FIG. 8 and is characterized by a mixture of sharp and broad reflections, indicating lower crystallinity. Table 3a shows characteristic peaks of Na salt Form 3. Table 3b shows extended peak list of Na salt Form 3.

TABLE 3a

Characteristic peaks of Na Salt Form 3

| Pos. [°2 Th.] | Rel. Int. [%] |
|---|---|
| 4.1 | 100 |
| 13.2 | 63 |
| 18.8 | 44 |
| 12.1 | 14 |
| 20.0 | 21 |
| 24.2 | 31 |
| 14.8 | 7 |
| 20.9 | 14 |
| 22.9 | 11 |

TABLE 3b

Extended peak list of Na Salt Form 3

| Pos. [°2 Th.] | Rel. Int. [%] |
|---|---|
| 4.1 | 100 |
| 8.2 | 4 |
| 12.1 | 14 |
| 13.2 | 63 |
| 14.8 | 7 |
| 18.8 | 44 |
| 20.0 | 21 |
| 20.9 | 14 |
| 22.9 | 11 |
| 24.2 | 31 |

Figure 9:
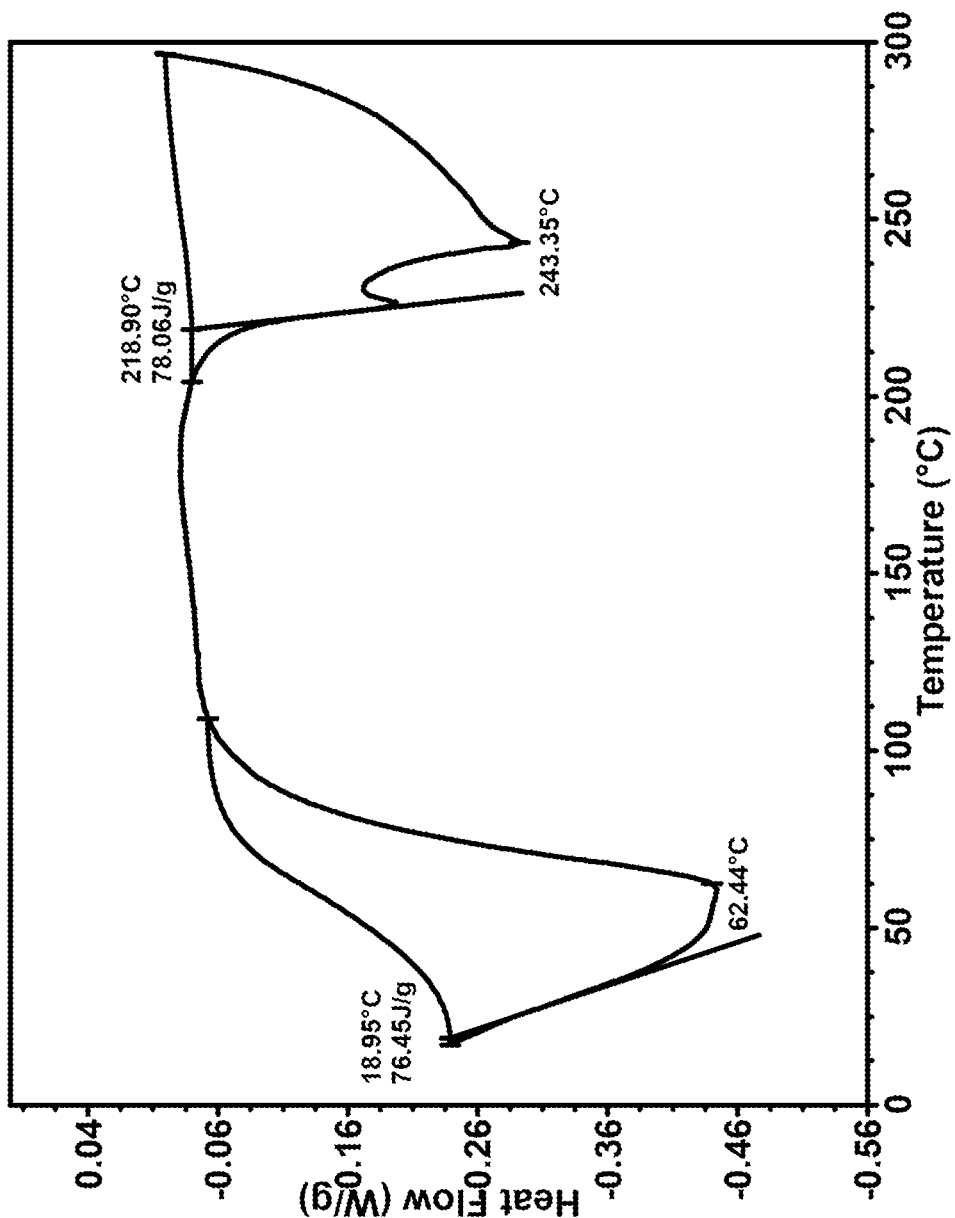
FIG. 9 provides a DSC thermogram for Na Salt Form 3.
Figure 10:
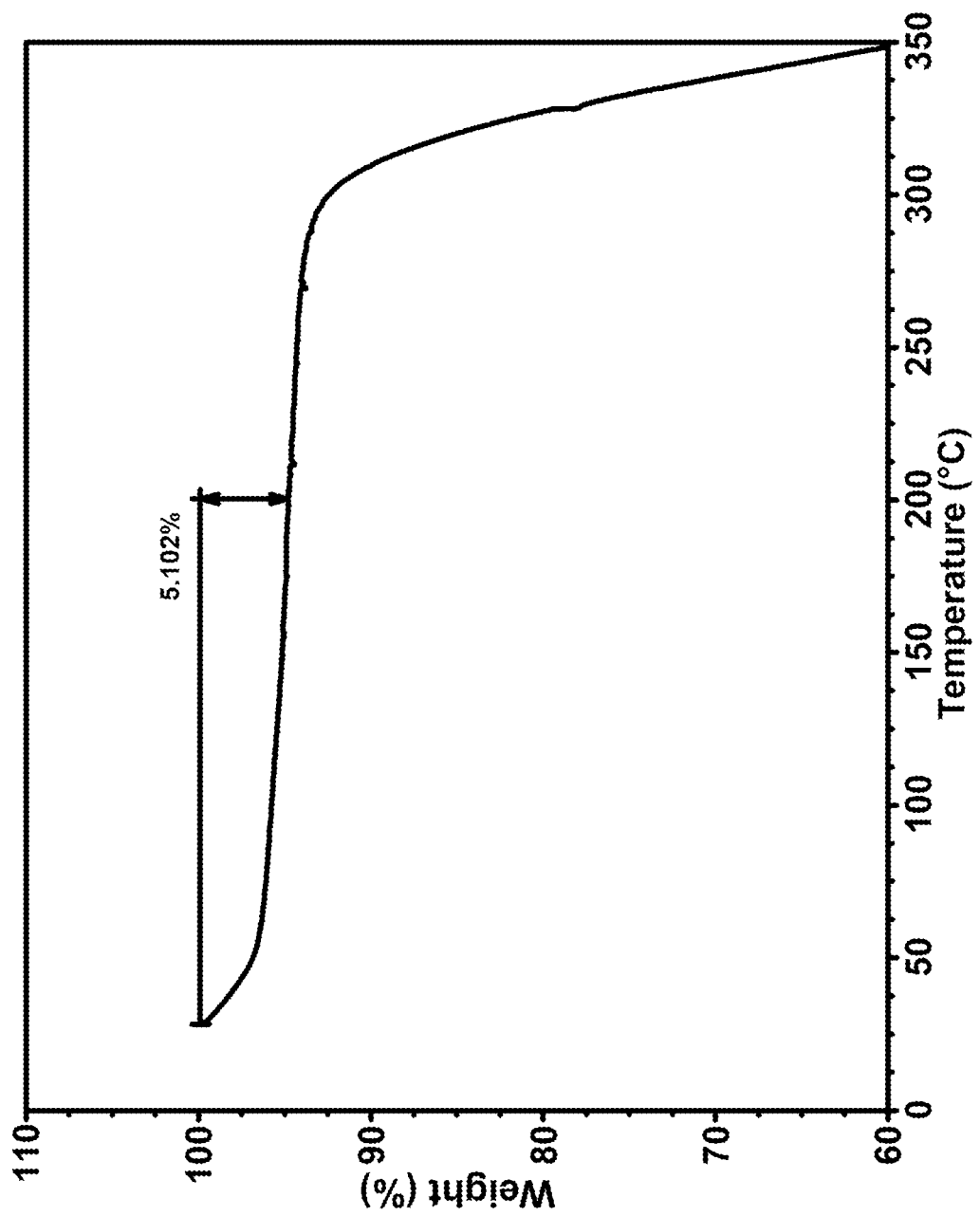
FIG. 10 provides a TGA thermogram for Na Salt Form 3.

The DSC thermogram of Na salt Form 3 is shown in FIG. 9. The DSC data shows broad endothermic event with onset temperature at about 19° C., followed by second broad endothermic event with an onset temperature at about 219° C. attributed to the melt of the salt and decomposition. The TGA thermogram of Na salt Form 3 is shown in FIG. 10. The TGA continuous weight loss of about 5.1 wt % observed from ambient temperature up to about 200° C. most likely corresponds to the loss of residual solvent or water.

E. Sodium Salt of Compound 1—Form 4 ("Na Salt Form 4")

Figure 11:
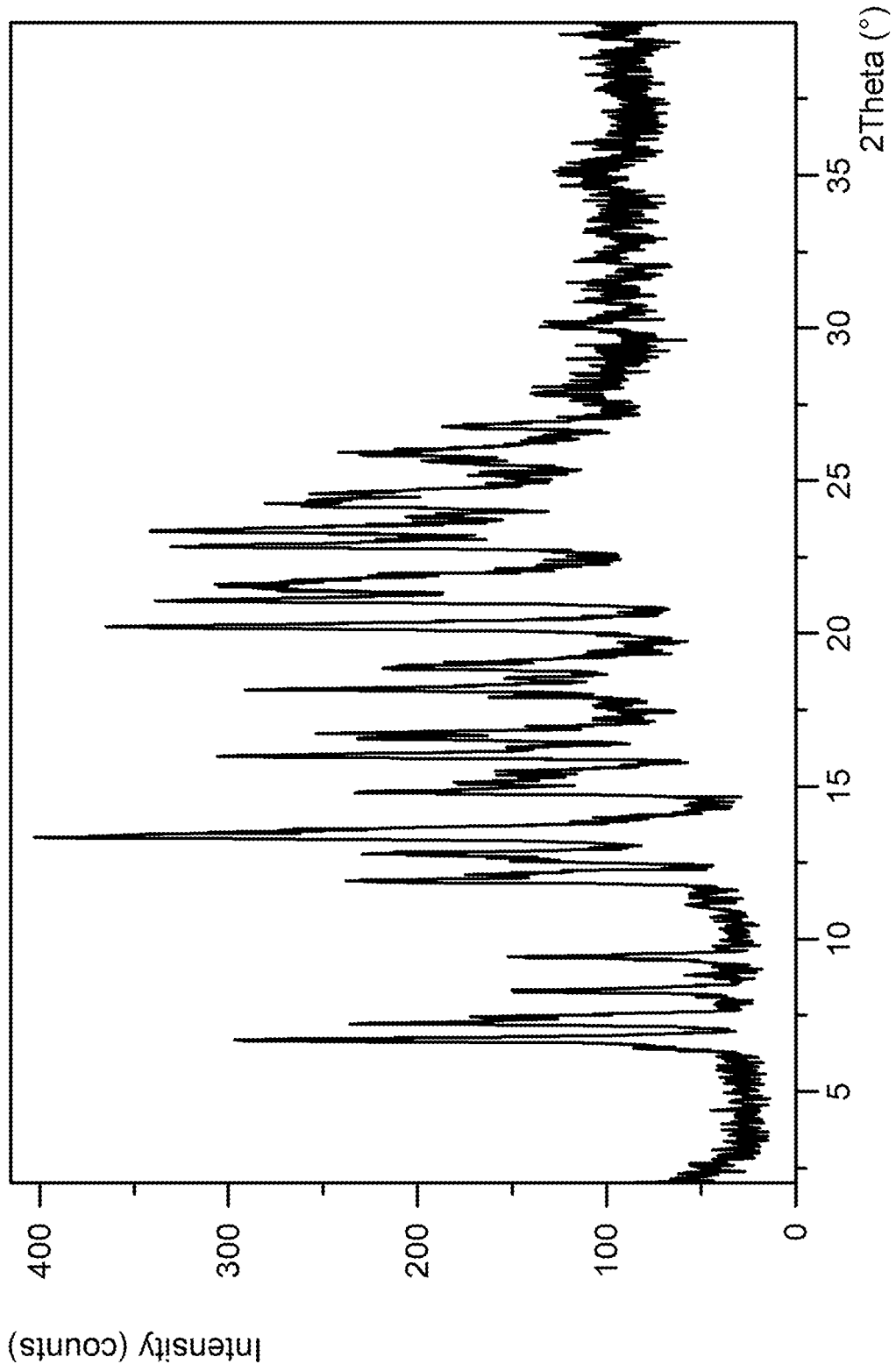
FIG. 11 provides an XRPD pattern for Na Salt Form 4.

Na Salt Form 4 was obtained by slurrying Na salt Form 1 with dimethylacetamide, followed by drying under vacuum at about 50° C. The XRPD pattern of Na Salt Form 4 is shown in FIG. 11 and is characterized by a mixture of sharp and broad reflections, indicating lower crystallinity. Table 4a shows characteristic peaks of Na Salt Form 4. Table 4b shows extended peak list of Na Salt Form 4.

TABLE 4a

Characteristic peaks of Na Salt Form 4

| Pos. [°2 Th.] | Rel. Int. [%] |
|---|---|
| 6.7 | 80 |
| 13.3 | 100 |
| 20.2 | 81 |
| 16.0 | 66 |
| 21.0 | 71 |
| 23.4 | 67 |
| 7.2 | 61 |
| 21.5 | 58 |
| 22.8 | 63 |

TABLE 4b

Extended peak list of Na Salt Form 4

| Pos. [°2 Th.] | Rel. Int. [%] |
|---|---|
| 6.7 | 80 |
| 7.2 | 61 |
| 7.5 | 37 |
| 8.3 | 33 |
| 9.4 | 35 |
| 11.9 | 50 |
| 12.8 | 49 |
| 13.3 | 100 |
| 14.8 | 49 |
| 15.5 | 26 |
| 16.0 | 66 |
| 16.5 | 45 |
| 16.8 | 46 |
| 18.2 | 58 |
| 18.9 | 41 |
| 20.2 | 81 |
| 21.0 | 71 |
| 21.5 | 58 |
| 22.8 | 63 |
| 23.4 | 67 |
| 24.2 | 42 |
| 25.9 | 32 |
| 26.8 | 23 |

F. Sodium Salt of Compound 1—Form 5 ("Na Salt Form 5")

Na Salt Form 5 was obtained after drying under vacuum at about 50° C. of the solvated form isolated from THF/water. More specifically, a 20 mL vial was charged with about 500 mg Form I of Compound 1 (synthesis described below) and about 4 mL THF and about 0.1 mL water, followed by the addition of about 1.1 eq. of NaOH. A mixture was stirred at about 50° C. for about 30 min, and then at ambient temperature for about two days. Isolated solids were analyzed by XRPD, followed by drying under vacuum at about 50° C. for about 16 h. XRPD pattern of the solids after drying was different compared to the pattern of wet solids, suggesting conversion of the solvated form to desolvated Na Salt Form 5 after drying.

Figure 12:
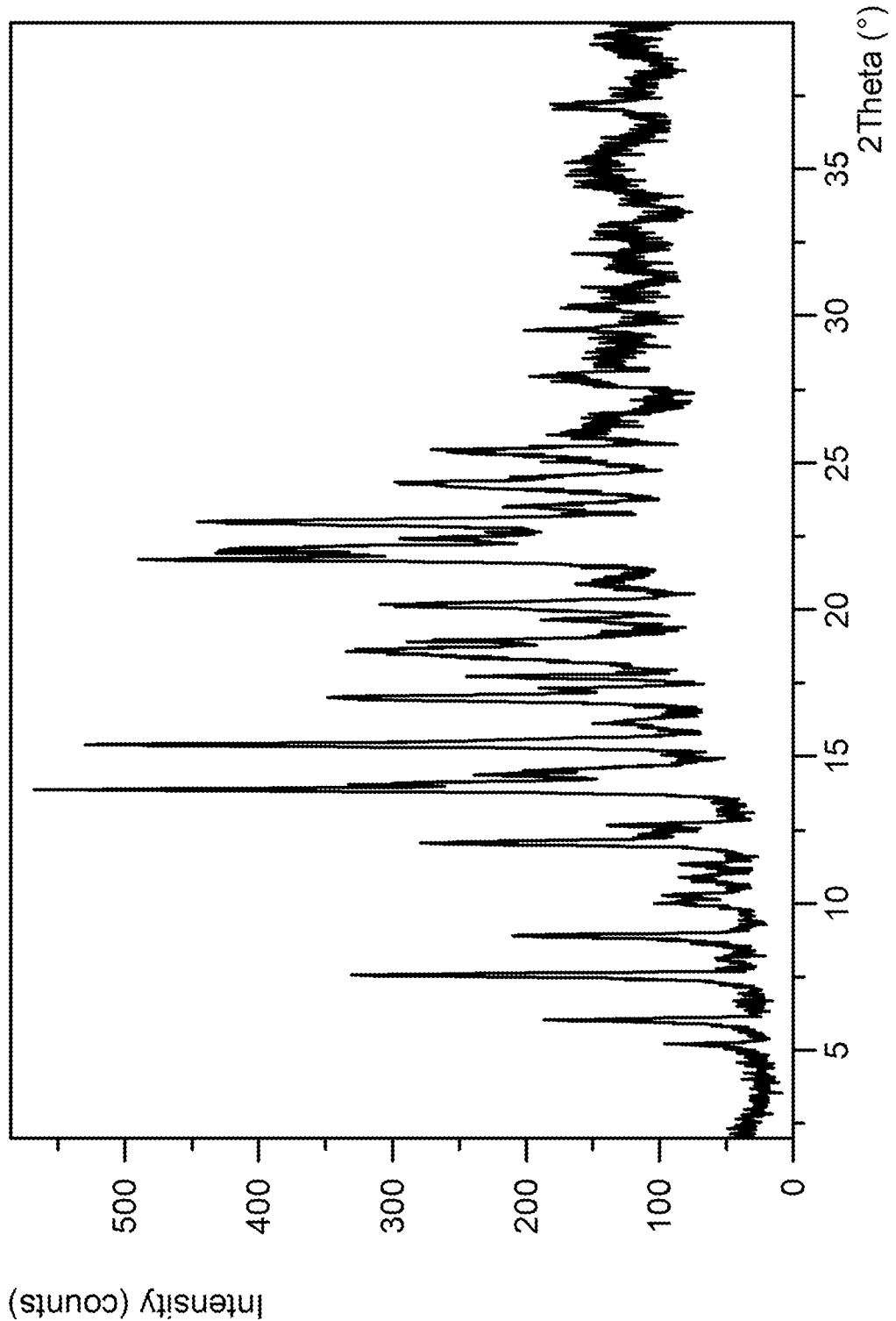
FIG. 12 provides an XRPD pattern for Na Salt Form 5.

The XRPD pattern of Na Salt Form 5 is shown in FIG. 12 and is characterized by a mixture of sharp and broad reflections, indicating lower crystallinity. Table 5a shows characteristic peaks of Na Salt Form 5. Table 5b shows extended peak list of Na Salt Form 5.

TABLE 5a

Characteristic peaks of Na Salt Form 5

| Pos. [°2 Th.] | Rel. Int. [%] |
|---|---|
| 7.6 | 57 |
| 13.9 | 100 |
| 15.4 | 83 |
| 6.0 | 31 |
| 8.9 | 34 |
| 12.1 | 45 |
| 17.0 | 50 |
| 21.7 | 72 |
| 23.0 | 59 |

TABLE 5b

Extended peak list of Na Salt Form 5

| Pos. [°2 Th.] | Rel. Int. [%] |
|---|---|
| 5.2 | 11 |
| 6.0 | 31 |
| 7.6 | 57 |
| 8.9 | 34 |
| 12.1 | 45 |
| 12.7 | 14 |
| 13.9 | 100 |
| 14.5 | 24 |
| 15.4 | 83 |
| 17.0 | 50 |
| 17.3 | 15 |
| 17.7 | 23 |
| 18.6 | 41 |
| 18.9 | 32 |
| 19.7 | 15 |
| 20.2 | 36 |
| 21.7 | 72 |
| 22.1 | 56 |
| 22.4 | 32 |
| 23.0 | 59 |
| 23.5 | 16 |
| 24.3 | 34 |
| 25.4 | 27 |
| 28.0 | 15 |
| 29.5 | 13 |
| 37.2 | 13 |

Figure 13:
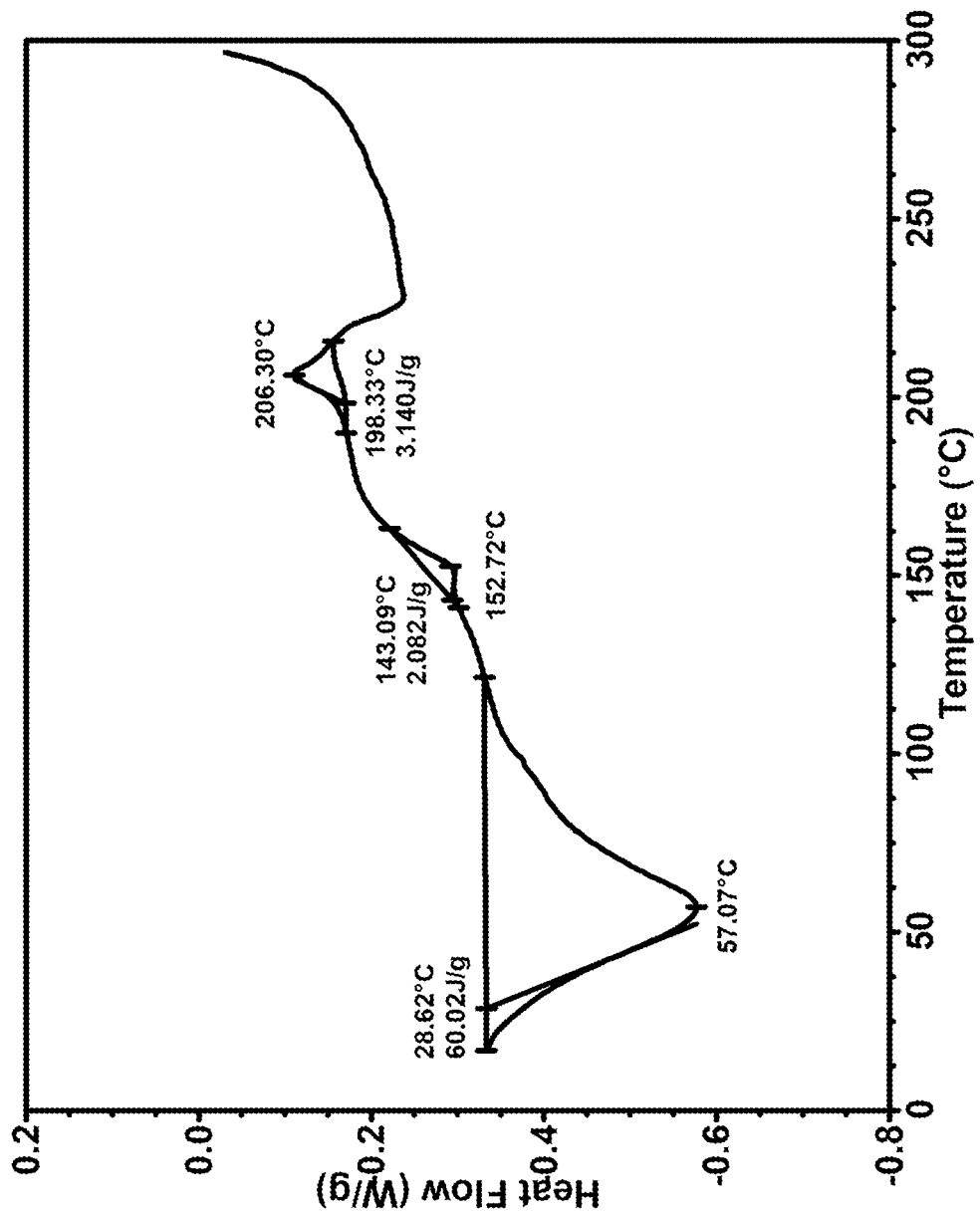
FIG. 13 provides a DSC thermogram for Na Salt Form 5.
Figure 14:
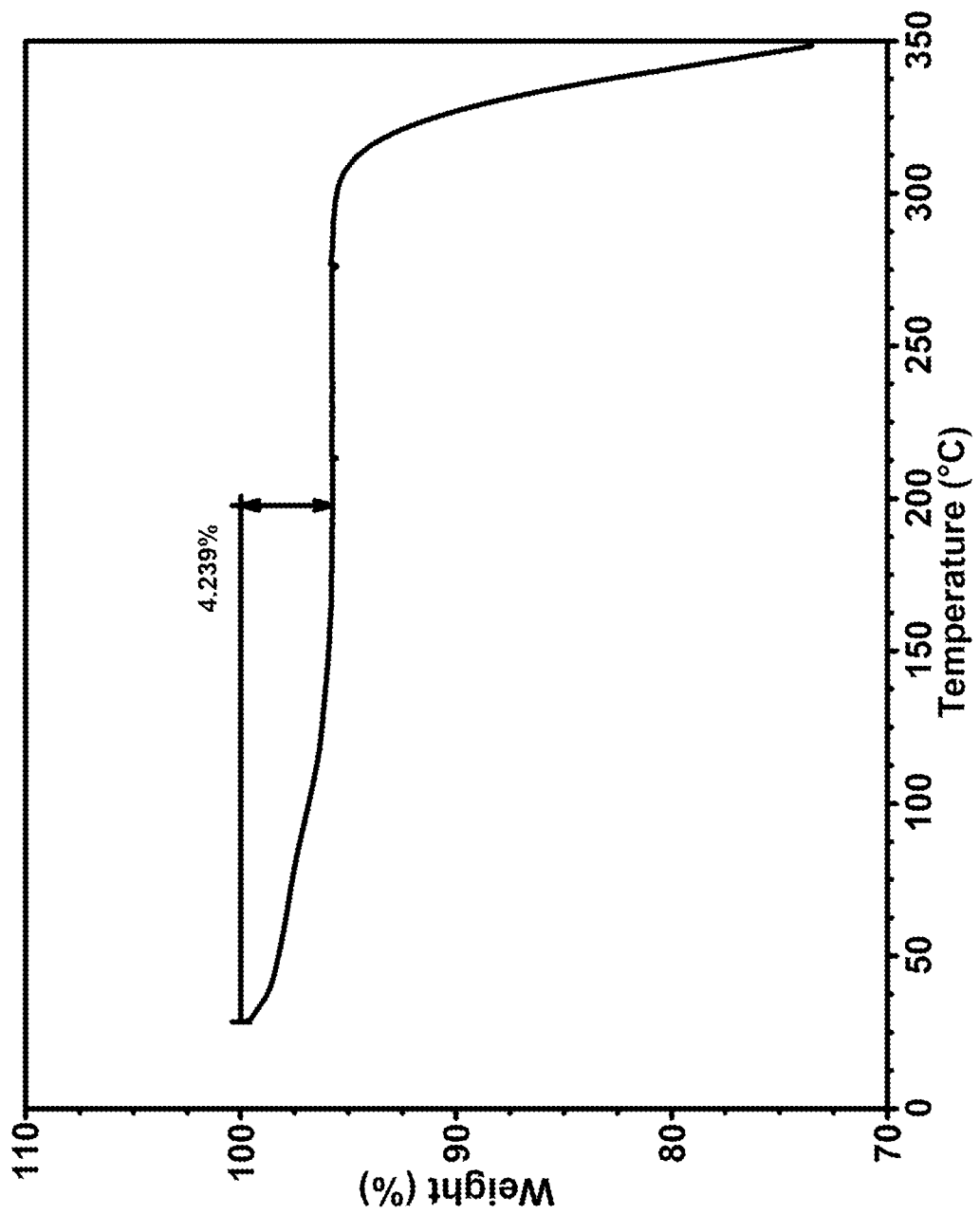
FIG. 14 provides a TGA thermogram for Na Salt Form 5.

The DSC thermogram of Na salt Form 5 is shown in FIG. 13. The DSC data shows broad endothermic event with onset temperature at about 29° C., followed by small second broad endothermic event with an onset temperature at about 143° C., and then exotherm with onset at about 198° C. The TGA thermogram of Na salt Form 5 is shown in FIG. 14. The TGA continuous weight loss of about 4.2 wt % observed from ambient temperature up to about 200° C. most likely corresponds to the loss of residual solvent or water.

G. Potassium Salt of Compound 1—Form 1 ("K Salt Form 1") & IPA Solvate ("K Salt IPA Solvate")

A potassium salt of Compound 1 was obtained during salt conversion of the Na Salt of Compound 1. More specifically, a 4 mL vial was charged with Na Salt Form 1 (about 100 mg) and about 1 mL of IPA, followed by the addition of about 2.1 eq. of KOH as about 50% aqueous solution, sonication, and stirring at about 50° C. for about 30 min and then at ambient temperature for about 3 days. The obtained solids were isolated by filtration and dried under vacuum at about 50° C. for about 16 h. Two crystalline forms of K salt were observed: (1) K Salt Form 1; and (2) an IPA solvate, which converted to desolvated Form 1 upon drying.

Figure 15:
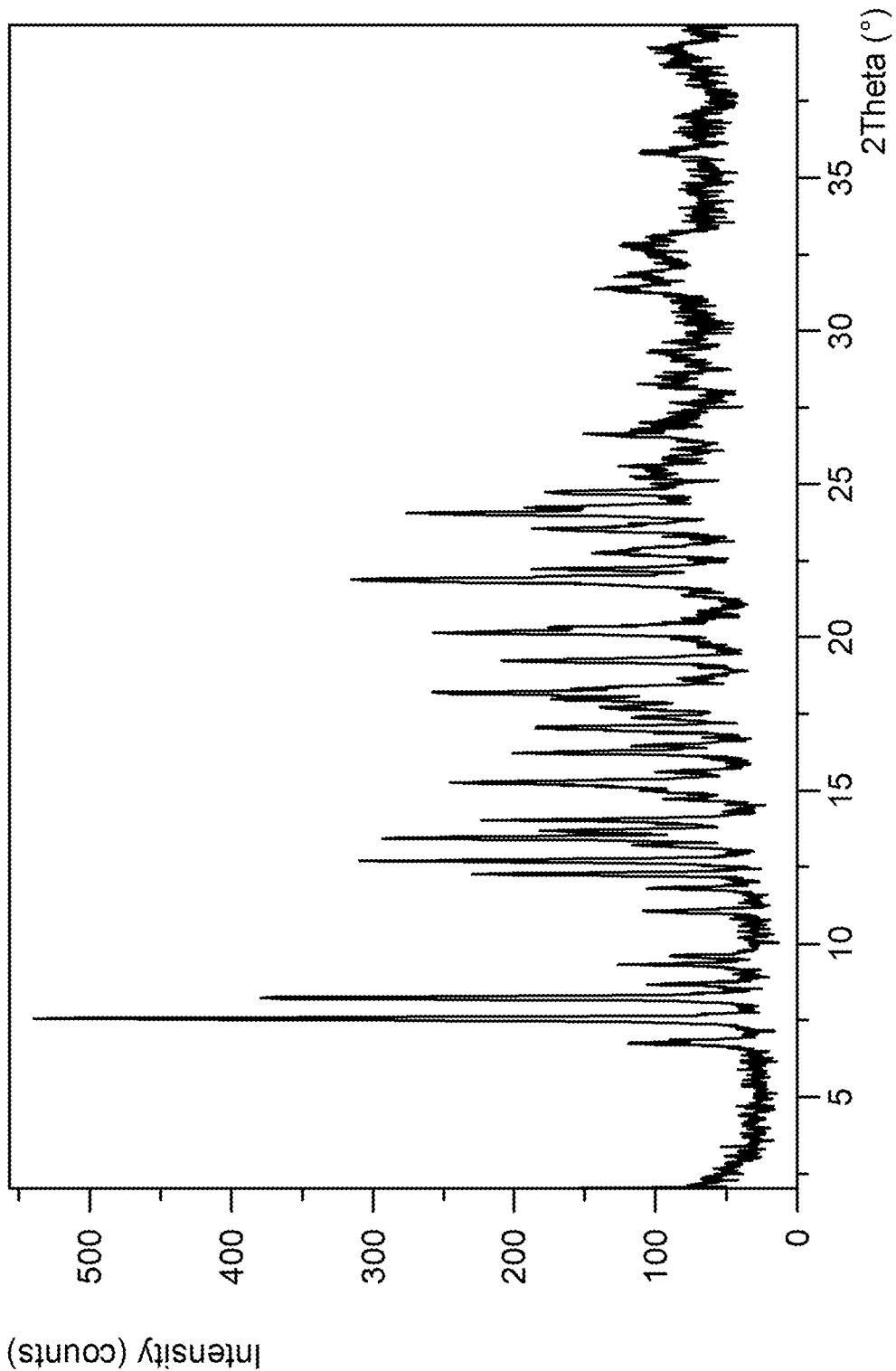
FIG. 15 provides an XRPD pattern for K Salt Form 1.
Figure 16:
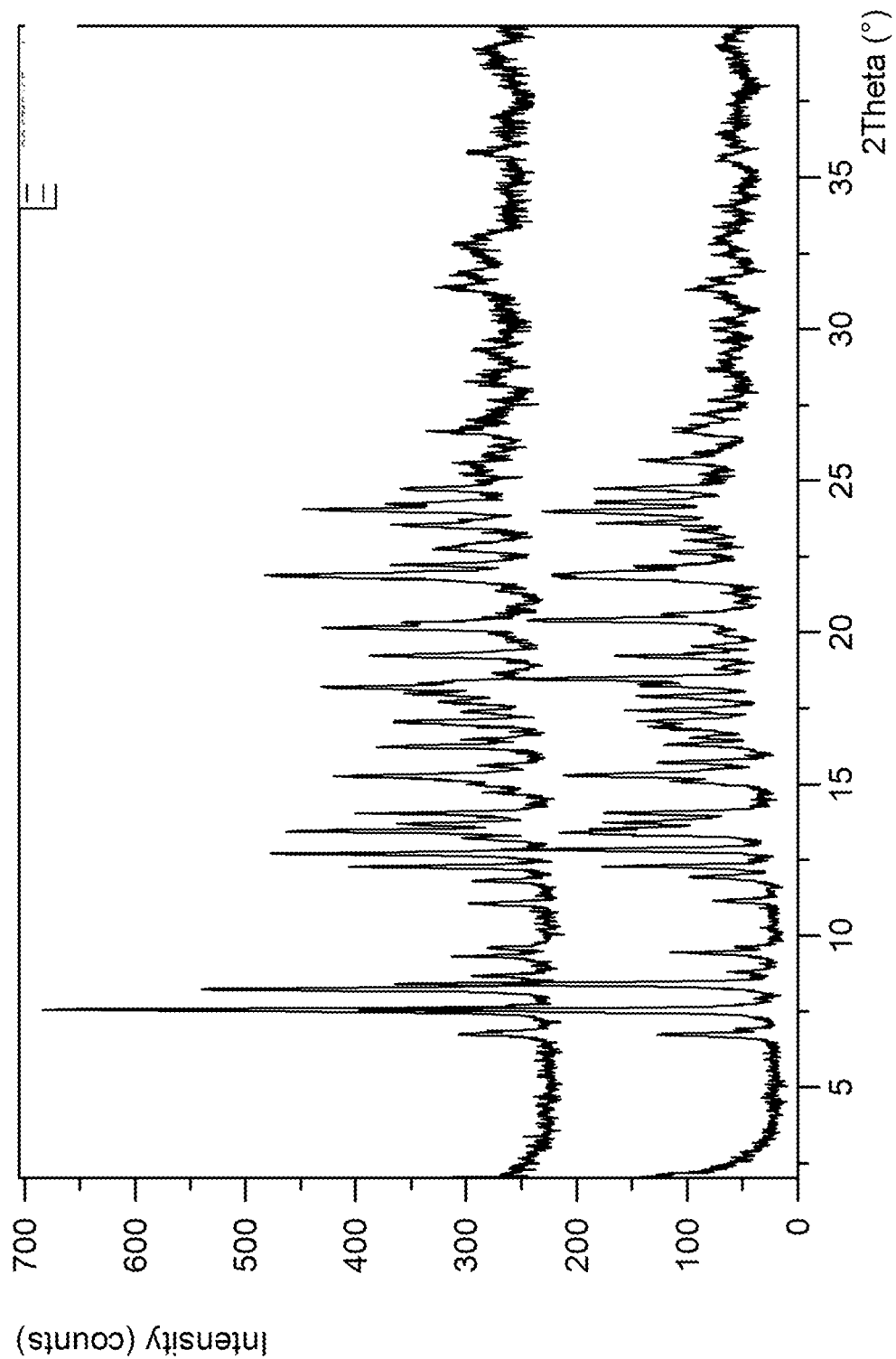
FIG. 16 provides a comparison of the XRPD pattern for Na Salt Form 1 as compared to the XRPD pattern for K Salt Form 1.

The XRPD pattern of K Salt Form 1 is shown in FIG. 15 and is characterized by sharp reflections, indicating crystallinity. Table 6a shows characteristic peaks of K Salt Form 1. Table 6b shows extended peak list of K Salt Form 1. The XRPD pattern of K Salt Form 1 is very similar to Na Salt Form 1 as shown in FIG. 16 (top and bottom, respectively).

TABLE 6a

Characteristic peaks of K Salt Form 1

| Pos. [°2 Th.] | Rel. Int. [%] |
|---|---|
| 7.6 | 100 |
| 8.2 | 70 |
| 12.7 | 54 |
| 13.4 | 49 |
| 18.2 | 41 |
| 21.9 | 48 |
| 12.3 | 39 |
| 15.3 | 40 |
| 20.1 | 40 |

TABLE 6b

Extended peak list of K Salt Form 1

| Pos. [°2 Th.] | Rel. Int. [%] |
|---|---|
| 6.7 | 18 |
| 7.6 | 100 |
| 8.2 | 70 |
| 9.3 | 18 |
| 11.1 | 16 |
| 12.3 | 39 |
| 12.7 | 54 |
| 13.4 | 49 |
| 13.7 | 27 |
| 14.0 | 37 |
| 15.3 | 40 |
| 16.2 | 31 |
| 17.1 | 27 |
| 17.7 | 18 |
| 18.2 | 41 |
| 19.2 | 31 |
| 20.1 | 40 |
| 21.9 | 48 |
| 22.2 | 24 |
| 23.5 | 21 |
| 24.1 | 38 |
| 24.7 | 19 |

Figure 17:
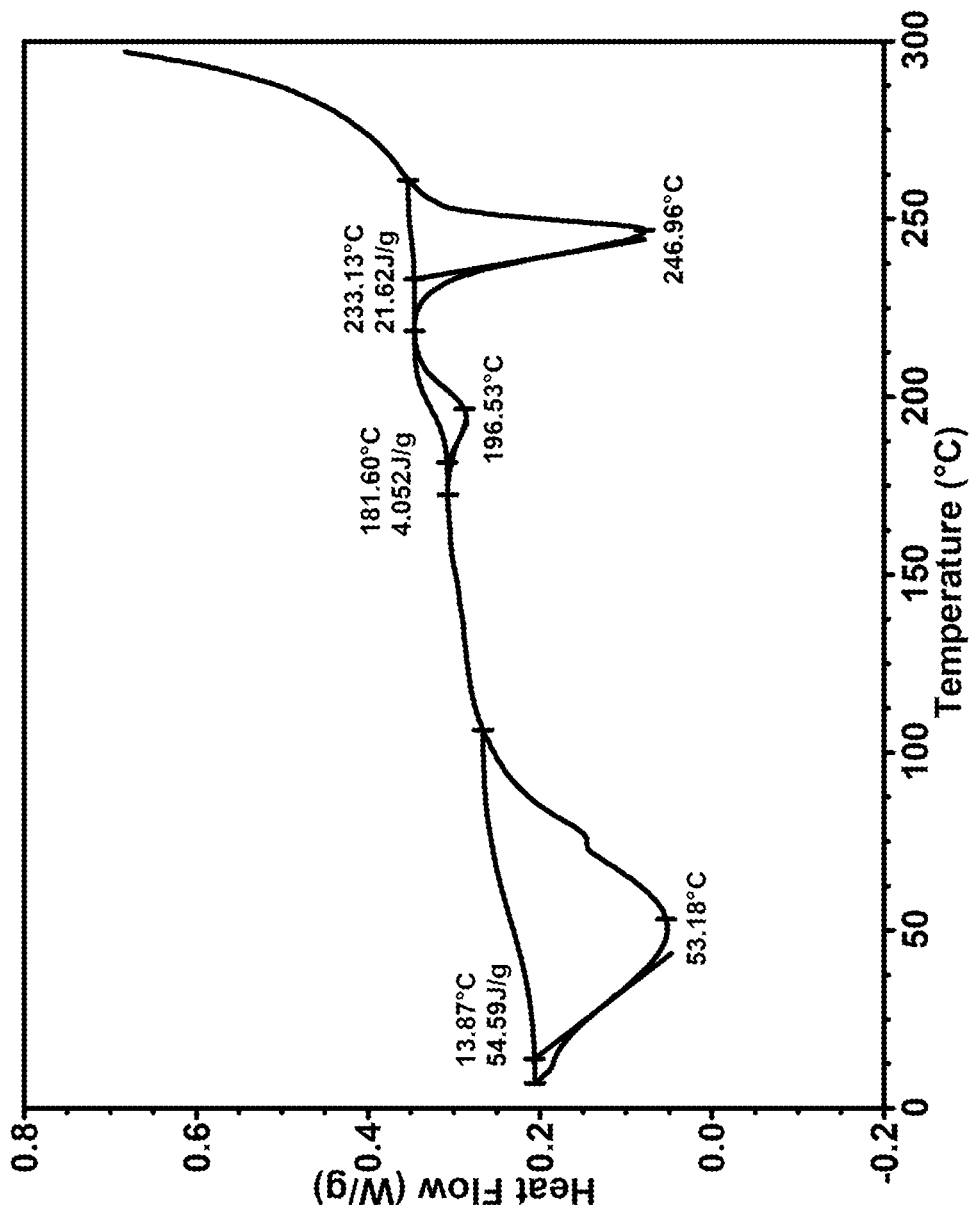
FIG. 17 provides a DSC thermogram for K Salt Form 1.
Figure 18:
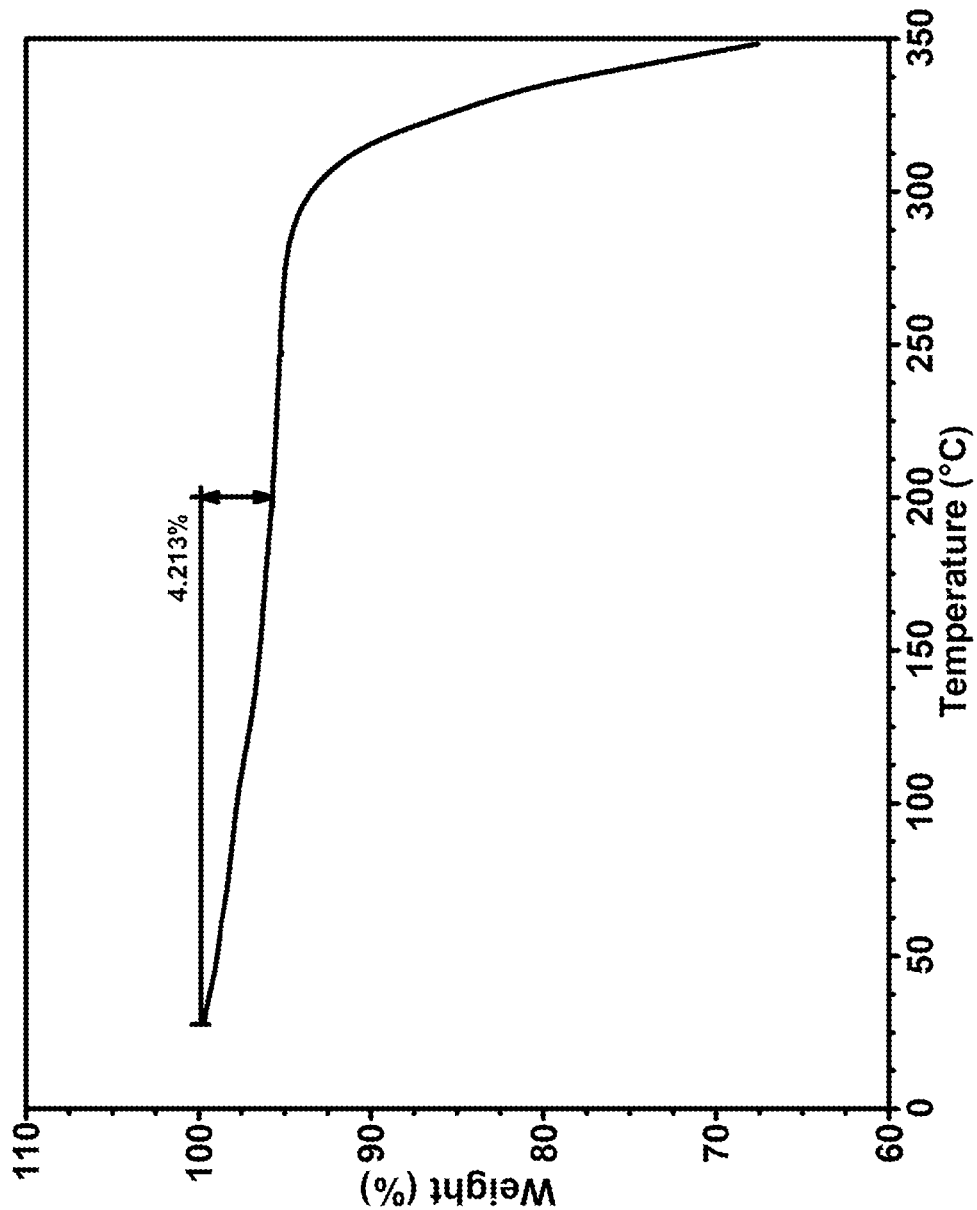
FIG. 18 provides a TGA thermogram for K Salt Form 1.
Figure 19:
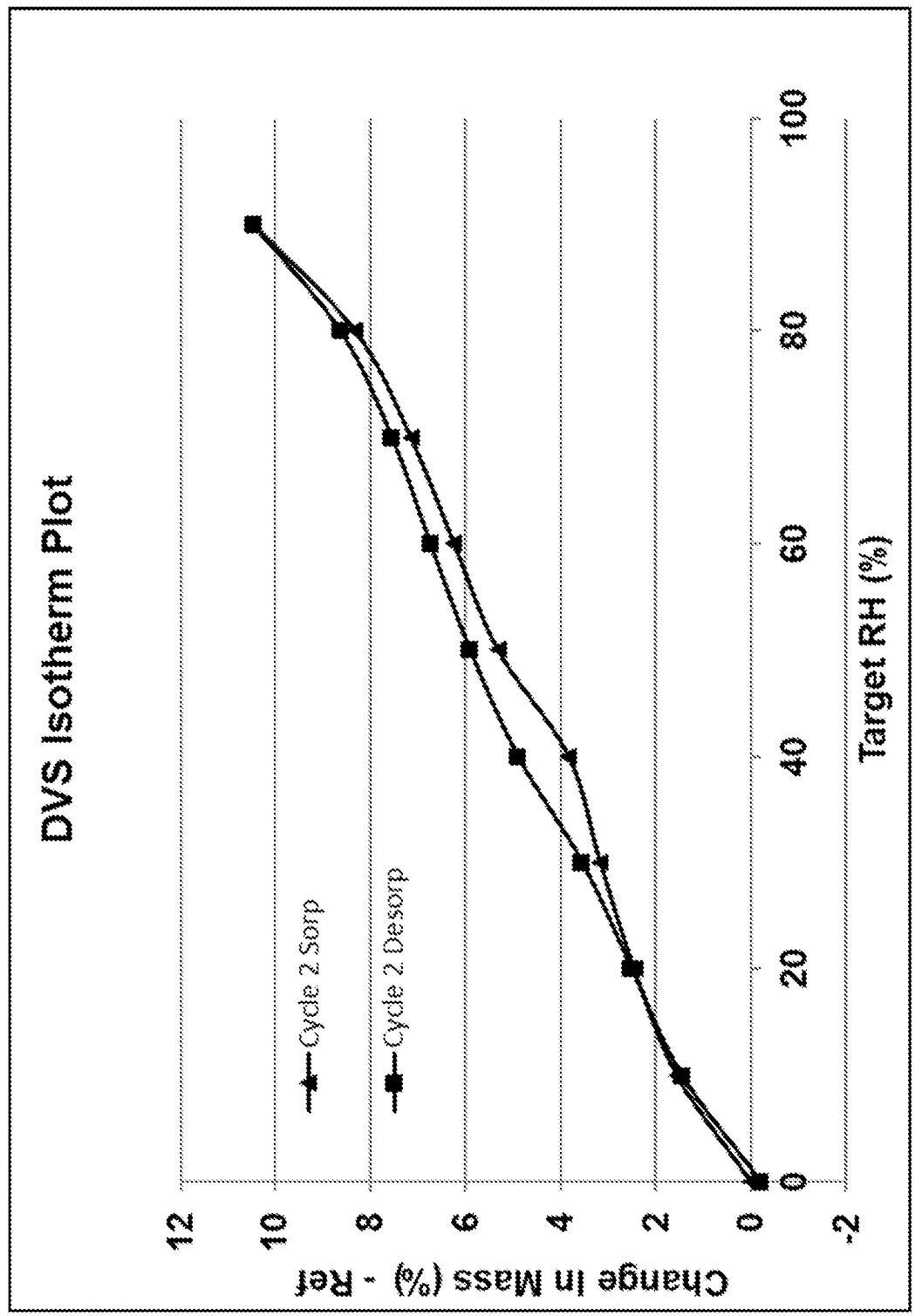
FIG. 19 provides a DVS analysis for K Salt Form 1.

The DSC thermogram of K Salt Form 1 is shown in FIG. 17. The DSC data shows three broad endothermic events with onset temperatures at about 14° C., at about 182° C., and at about 233° C. attributed to the loss of residual solvent or water, potential form conversion, and melt, respectively. The TGA thermogram of K Salt Form 1 is shown in FIG. 18. The TGA thermogram shows continuous weight loss of about 4.2 wt % observed from ambient temperature up to about 200° C., which most likely corresponds to the loss of residual solvent or water. DVS analysis is shown in FIG. 19 and indicates that K Salt Form 1 is moderately hygroscopic with about 11 wt % moisture uptake between 0% and 90% RH and about 25° C. K Salt Form 1 rapidly absorbs moisture up to about 4-6 wt % at ambient conditions. XRPD analysis of the sample post DVS showed no form change.

Figure 20:
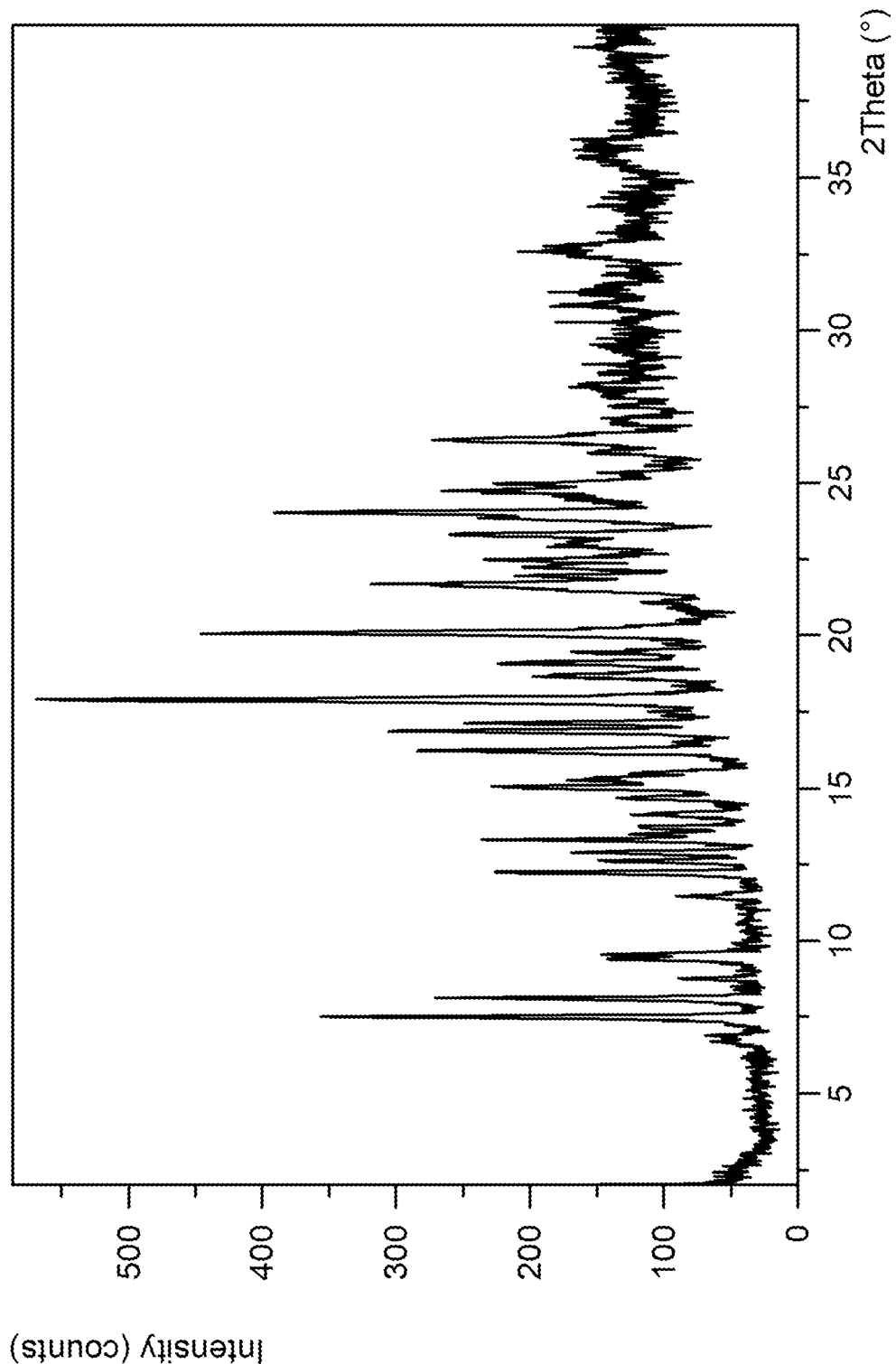
FIG. 20 provides an XRPD pattern for K Salt IPA Solvate.

The XRPD pattern of K salt IPA solvate is shown in FIG. 20 and is characterized by sharp reflections, indicating crystallinity.

H. Potassium Salt of Compound 1—THF Solvate ("K Salt THF Solvate")

The K Salt THF solvate was obtained during potassium salt formation in THF. More specifically, a 20 mL vial was charged with about 500 mg of polymorph Form I of Compound 1 (preparation described below) and about 2 mL of THF, followed by the addition of about 1.1 eq. of KOH as about 50% aqueous solution. This mixture was stirred at about 50° C. for about 15 min and then at ambient temperature for about 16 hr. The obtained solids were isolated by filtration and dried under vacuum at about 50° C. for about 24 h to afford the K Salt THF solvate. The XRPD pattern is shown in FIG. 21 and is characterized by sharp reflections, indicating crystallinity.

I. Diethylamine Salt of Compound 1—Toluene Solvate ("DEA Salt Toluene Solvate")

Figure 22:
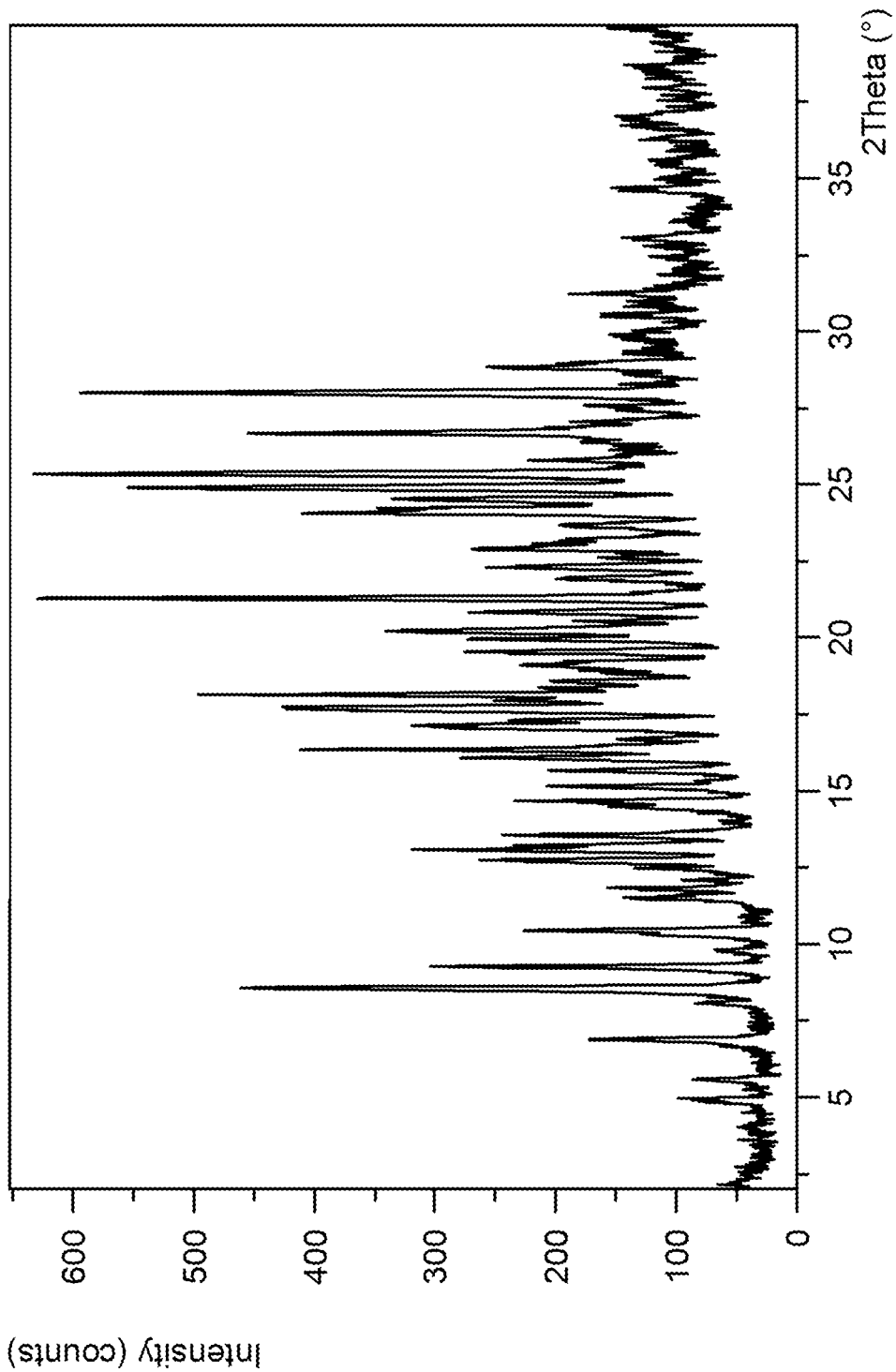
FIG. 22 provides an XRPD pattern for DEA Salt Toluene Solvate.

The DEA Salt Toluene solvate was prepared by charging about 1.1 mol. eq. of diethylamine to a slurry of Form I of Compound 1 in 1 mL EtOH at about 50° C., followed by cooling to ambient temperature. Crystalline solids were not formed. The mixture was concentrated down to dryness. The remaining oil was re-dissolved in toluene, followed by the slow addition of heptane as anti-solvent. After overnight stirring at ambient temperature crystalline solids were formed. Based on XRPD analysis, the wet solids were most likely toluene solvate, which converted to desolvated disordered form (Form I) upon drying. The XRPD pattern of the DEA Salt Toluene solvate is shown in FIG. 22, and is characterized by sharp reflections, indicating crystallinity.

J. Diethylamine Salt of Compound 1—Form 1 ("DEA Salt Form 1")

Figure 23:
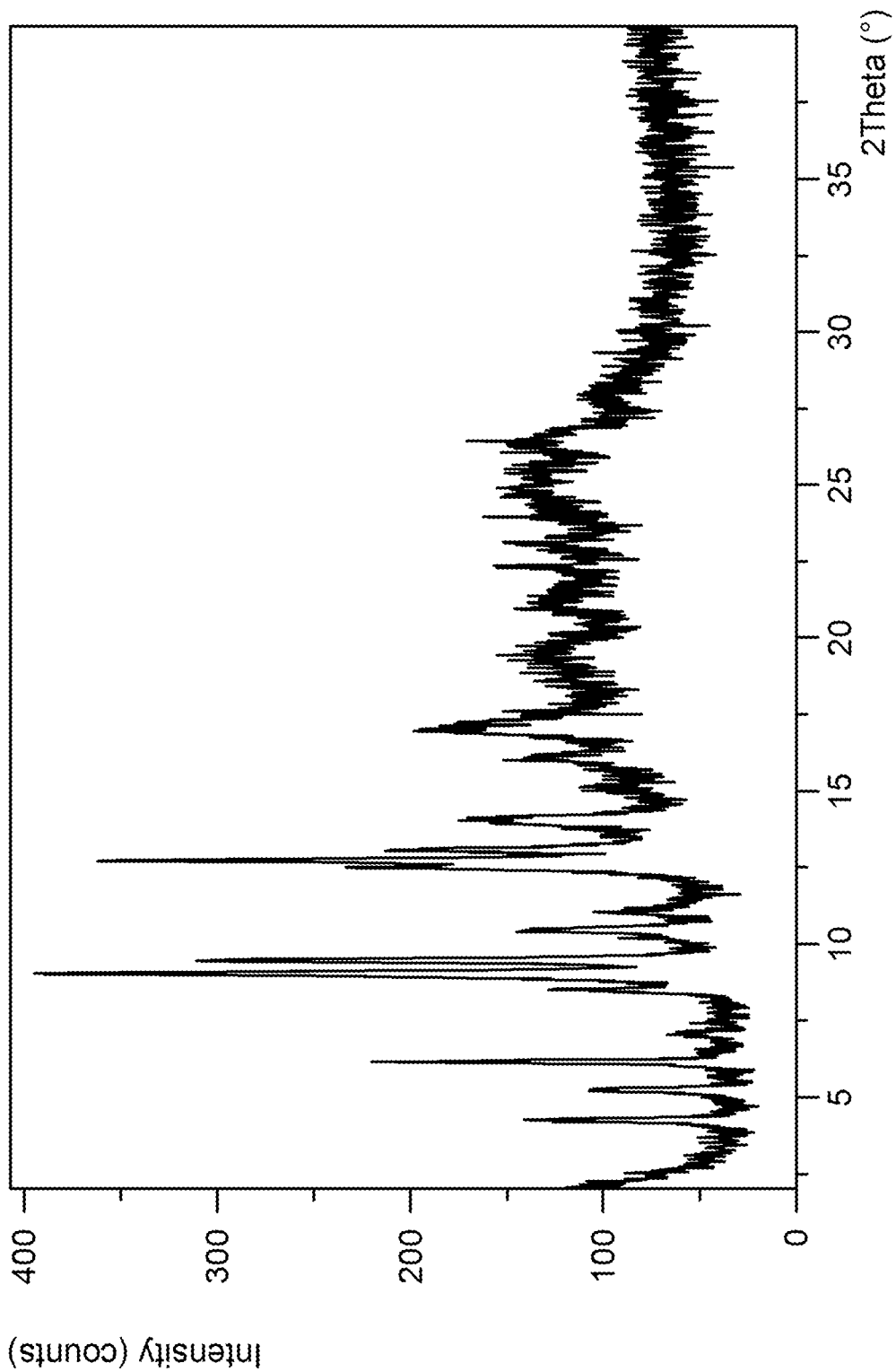
FIG. 23 provides an XRPD pattern for DEA Salt Form 1.

As noted above, the DEA Salt Form 1 is a desolvated form obtained after drying of the DEA Salt Toluene solvate. The XRPD pattern of DEA Salt Form 1 is shown in FIG. 23 and is characterized by a mixture of sharp and broad reflections, indicating lower crystallinity. Table 7a shows characteristic peaks of DEA Salt Form 1. Table 7b shows extended peak list of DEA Salt Form 1.

TABLE 7a

Characteristic peaks of DEA Salt Form 1

| Pos. [°2 Th.] | Rel. Int. [%] |
|---|---|
| 9.0 | 99 |
| 9.5 | 81 |
| 12.7 | 100 |
| 6.2 | 61 |
| 12.5 | 52 |
| 13.1 | 46 |
| 4.3 | 31 |
| 14.1 | 30 |
| 17.0 | 29 |

TABLE 7b

Extended peak list of DEA Salt Form 1

| Pos. [°2 Th.] | Rel. Int. [%] |
|---|---|
| 4.3 | 31 |
| 5.2 | 24 |
| 6.2 | 61 |
| 8.5 | 24 |
| 9.0 | 99 |
| 9.5 | 81 |
| 10.5 | 29 |
| 12.5 | 52 |
| 12.7 | 100 |

TABLE 7b-continued

Extended peak list of DEA Salt Form 1

| Pos. [°2 Th.] | Rel. Int. [%] |
|---|---|
| 13.1 | 46 |
| 14.1 | 30 |
| 16.1 | 14 |
| 17.0 | 29 |
| 19.5 | 9 |
| 21.1 | 10 |
| 26.4 | 14 |

Figure 24:
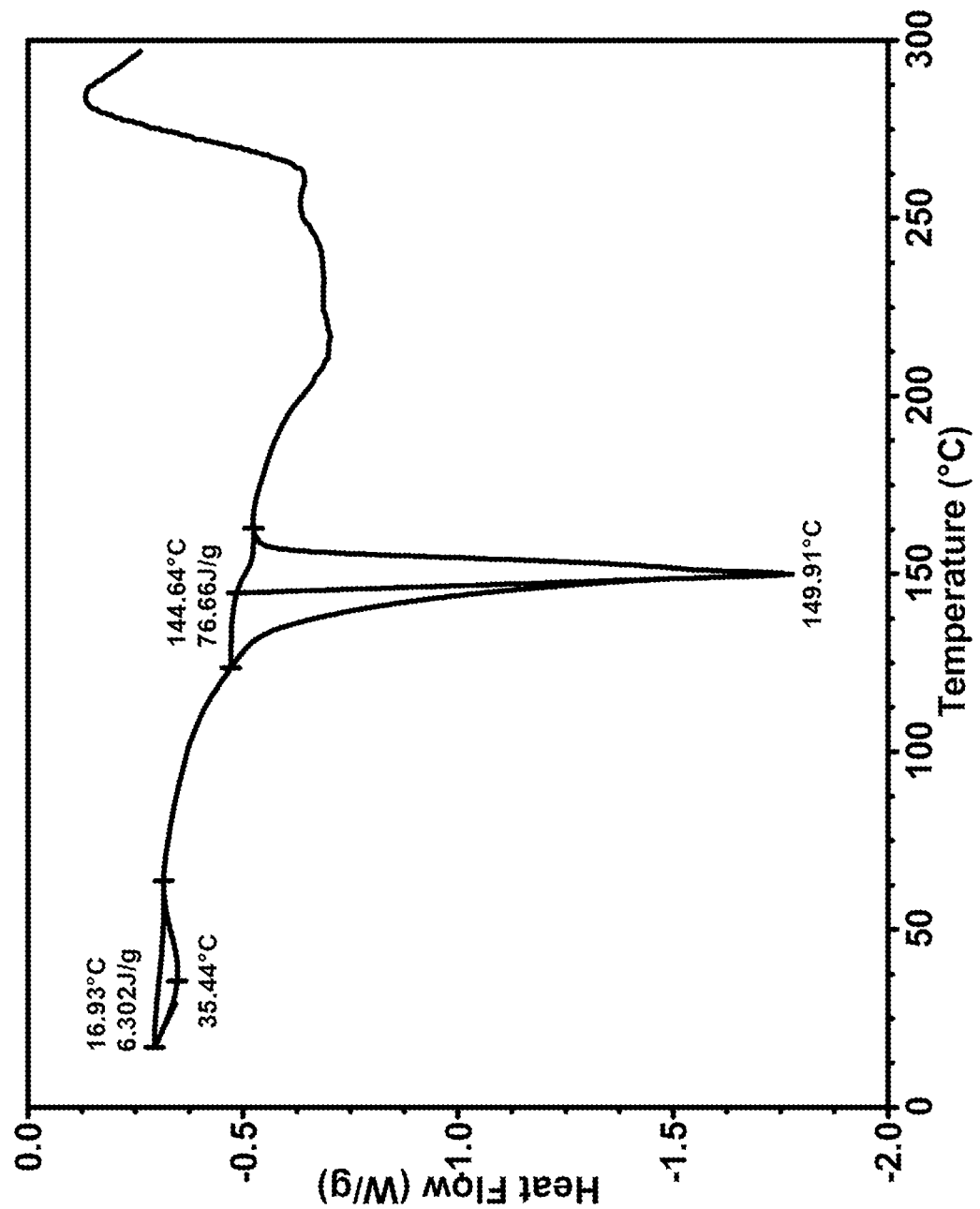
FIG. 24 provides a DSC thermogram for DEA Salt Form 1.
Figure 25:
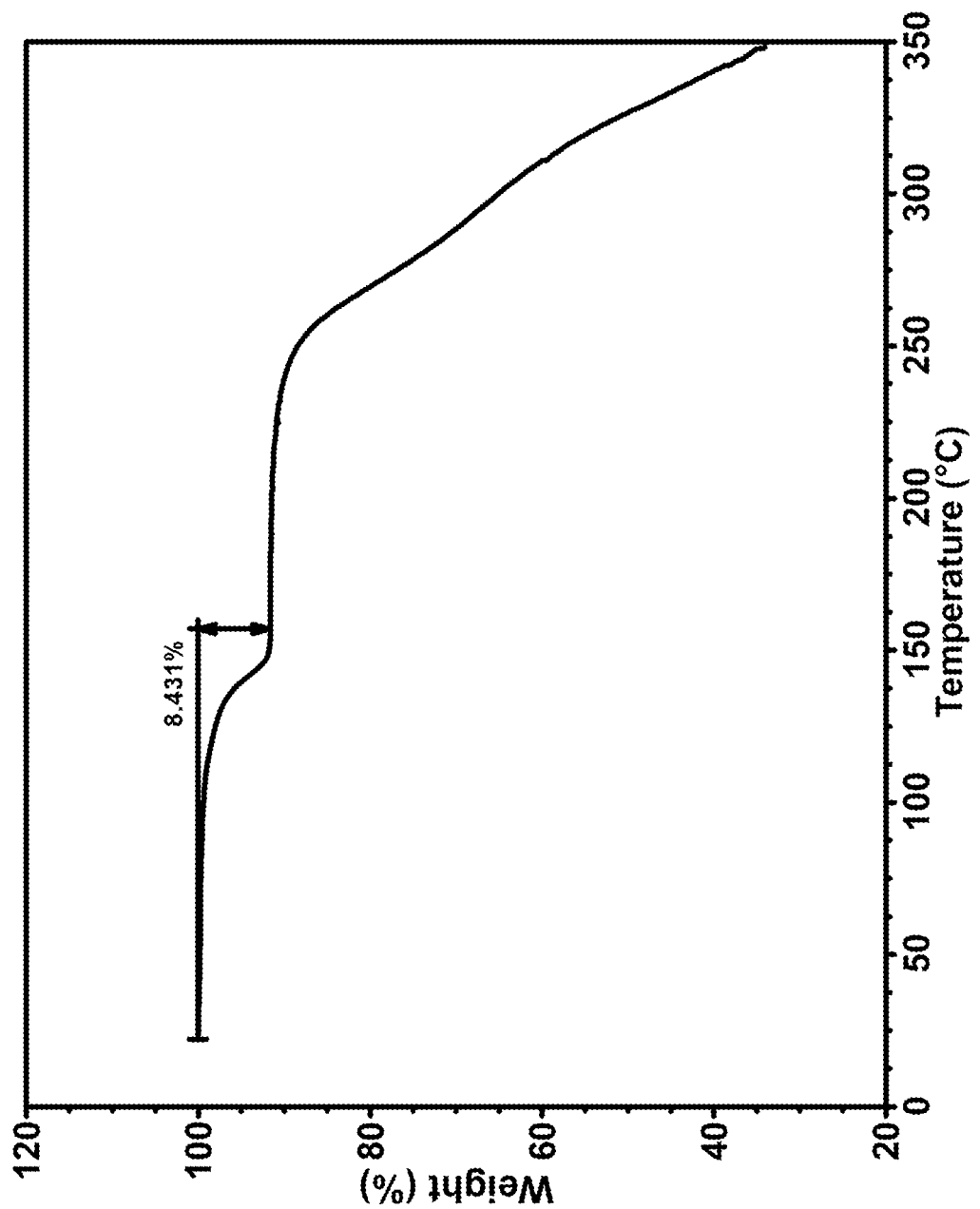
FIG. 25 provides a TGA thermogram for DEA Salt Form 1.
Figure 26:
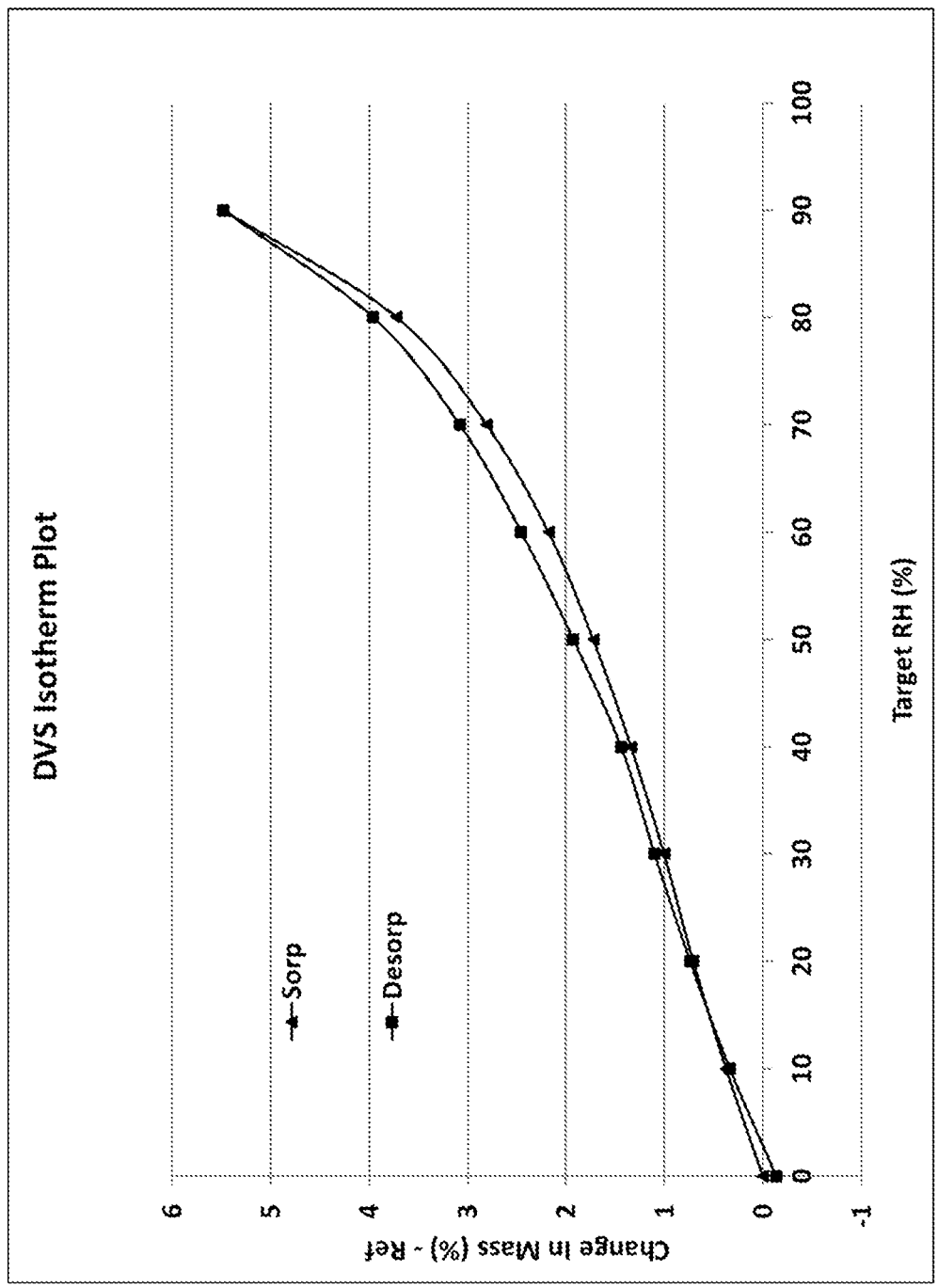
FIG. 26 provides a DVS analysis for DEA Salt Form 1.

The DSC thermogram of DEA Salt Form 1 is shown in FIG. 24. The DSC data shows small broad endotherm with onset temperature at about 17° C., followed by endotherm with onset temperature at about 145° C. The TGA thermogram of DEA Salt Form 1 is shown in FIG. 25. The TGA weight loss of about 8.4 wt % observed from ambient temperature up to about 170° C. corresponds to dissociation of the salt. DVS analysis of DEA Salt Form 1 is shown in FIG. 26 and indicates that it is moderately hygroscopic, absorbing at about 5.5 wt % of water between 0% and 90% RH at about 25° C. However, XRPD analysis of the post DVS sample showed no form change.

K. Choline Salt of Compound 1—Form 1 ("Choline Salt Form 1")

Figure 27:
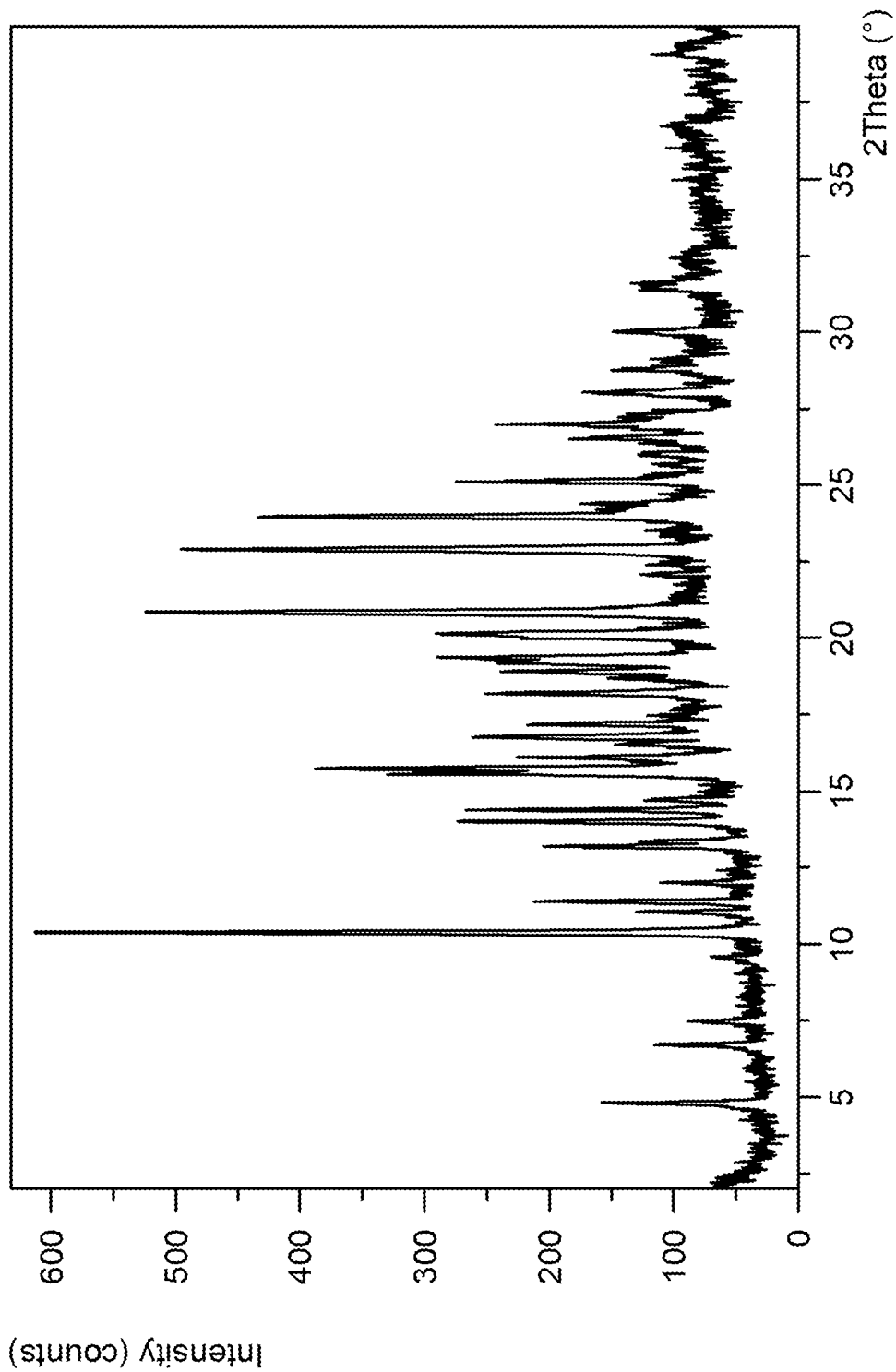
FIG. 27 provides an XRPD pattern for Choline Salt Form 1.

Choline Salt Form 1 was obtained from the slurry in EtOAc/heptane solvent mixture. More specifically, 4 mL vial was charged with Form I of Compound 1 (about 45 mg) and about 0.5 mL of EtOH followed by the addition of about 1.1 eq. of choline hydroxide (as about 45% solution in MeOH) to afford a solution. Solution was concentrated to dryness. EtOH/heptane (about 1.25 mL of 3:2 mixture) was added to the remaining oil, followed by stirring at about 50° C. for about 1 h and then at ambient temperature. The obtained solids were isolated by filtration and dried under vacuum at about 50° C. for about 24 h. No form change was observed before and after drying. The XRPD pattern of Choline Salt Form 1 is shown in FIG. 27 and is characterized by sharp reflections, indicating crystallinity. Table 8a shows characteristic peaks of Choline Salt Form 1. Table 8b shows extended peak list of Choline Salt Form 1.

TABLE 8a

Characteristic peaks of Choline Salt Form 1

| Pos. [°2 Th.] | Rel. Int. [%] |
|---|---|
| 10.4 | 100 |
| 20.9 | 77 |
| 22.9 | 68 |
| 14.0 | 39 |
| 15.7 | 57 |
| 24.0 | 59 |
| 14.4 | 34 |
| 16.8 | 31 |
| 25.1 | 27 |

TABLE 8b

Extended peak list of Choline Salt Form 1

| Pos. [°2 Th.] | Rel. Int. [%] |
|---|---|
| 4.8 | 22 |
| 10.4 | 100 |
| 11.0 | 15 |
| 11.4 | 27 |

TABLE 8b-continued

Extended peak list of Choline Salt Form 1

| Pos. [°2 Th.] | Rel. Int. [%] |
|---|---|
| 13.2 | 23 |
| 14.0 | 39 |
| 14.4 | 34 |
| 15.6 | 45 |
| 15.7 | 57 |
| 16.1 | 25 |
| 16.8 | 31 |
| 17.2 | 22 |
| 18.2 | 27 |
| 18.9 | 25 |
| 19.4 | 27 |
| 20.2 | 27 |
| 20.9 | 77 |
| 22.9 | 68 |
| 24.0 | 59 |
| 25.1 | 27 |
| 27.0 | 25 |
| 28.0 | 16 |

Figure 28:
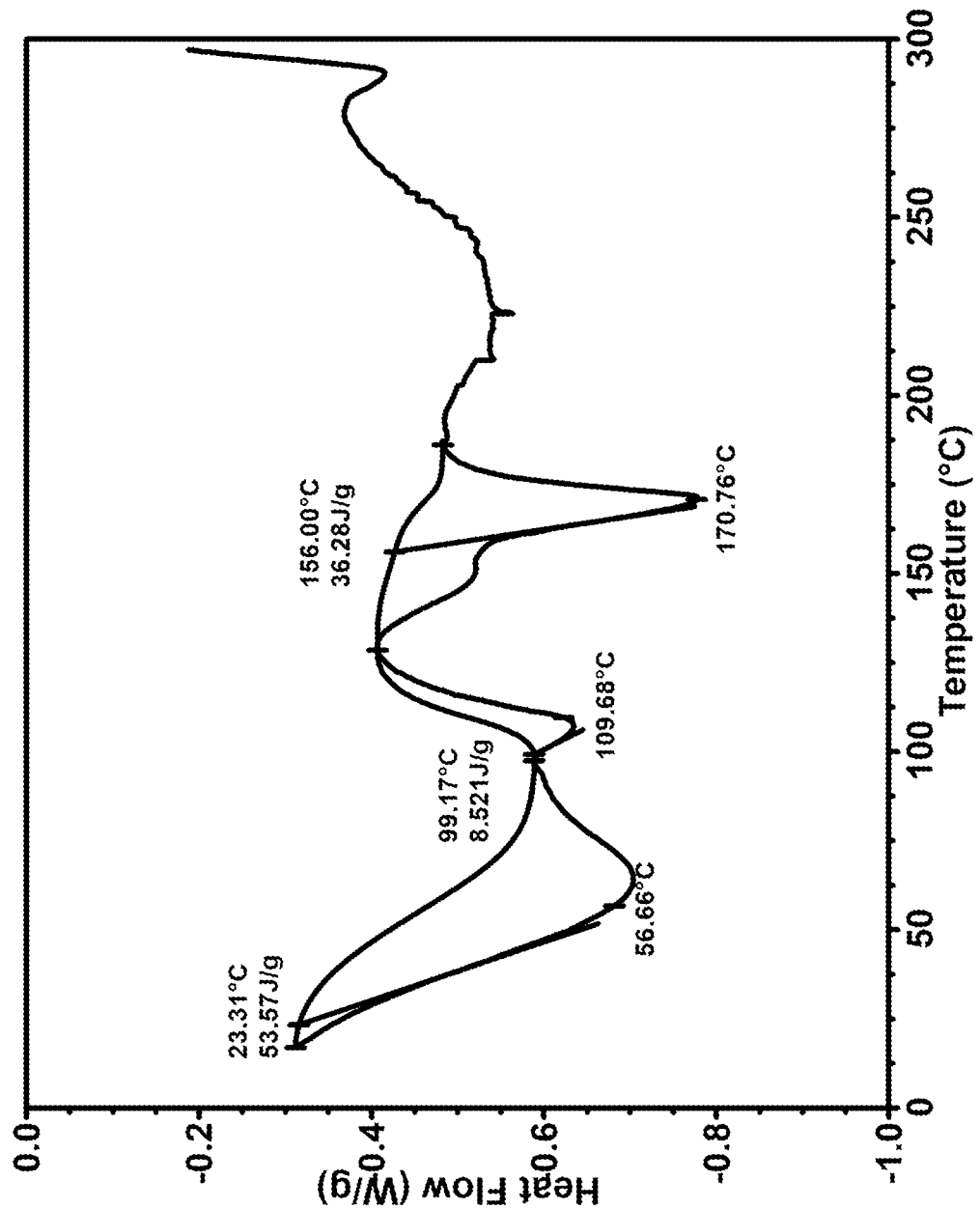
FIG. 28 provides a DSC thermogram for Choline Salt Form 1.
Figure 29:
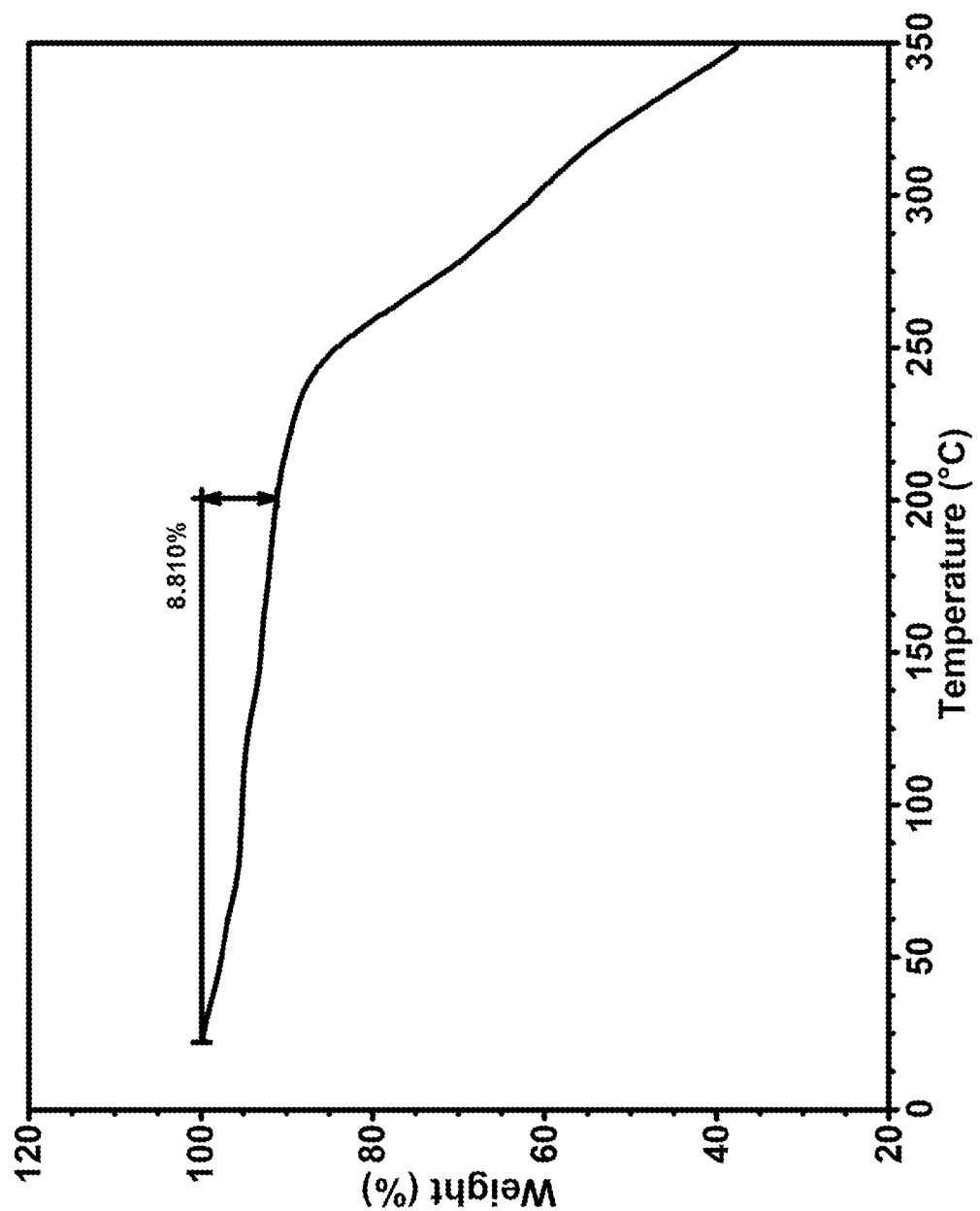
FIG. 29 provides a TGA thermogram for Choline Salt Form 1.

The DSC thermogram of Choline Salt Form 1 is shown in FIG. 28. The DSC data shows three broad endothermic events with onset temperatures at about 23° C., at about 99° C., and at about 156° C. attributed to the loss of residual solvents or water, and melt, respectively. The TGA thermogram of Choline Salt Form 1 is shown in FIG. 29. The TGA thermogram shows step-wise weight loss of about 8.8 wt % total observed from ambient temperature up to about 200° C., which most likely corresponds to the loss of residual solvents or water.

Example 2. Polymorph Study of Compound 1

A polymorph study was performed on Compound 1 as described below.

Compound 1

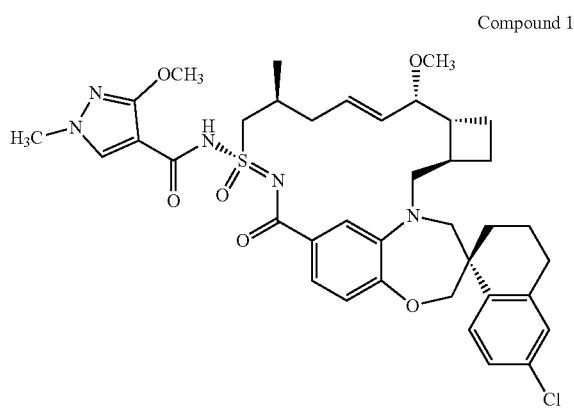 [SMILES: COc1nn(C)cc1C(=O)N[S@@]1(=O)=NC(=O)c2ccc3c(c2)N(C[C@@H]2CC[C@H]2[C@@H](OC)/C=C/C[C@H](C)C1)C[C@@]1(CCCc2cc(Cl)ccc21)CO3]

More specifically, a study was conducted on Compound 1 in amorphous form. A hydrate study was also conducted in MeCN/water at ambient conditions and at 50° C., but did not afford any hydrated forms. Certain polymorphs were also obtained starting from one or more of the salts discovered above.

Based on these studies, 4 unsolvated/desolvated forms were discovered, 8 solvates were identified having unique XRPD patterns, and 8 isostructural solvated forms were discovered having XRPD patterns mostly consistent with Form I with some peak shifts and sometimes with small extra peaks. Single crystal X-ray analysis showed almost identical cell parameters of the crystals isolated from MeCN, acetone, and EtOH.

A. Amorphous Form of Compound 1

Figure 30:
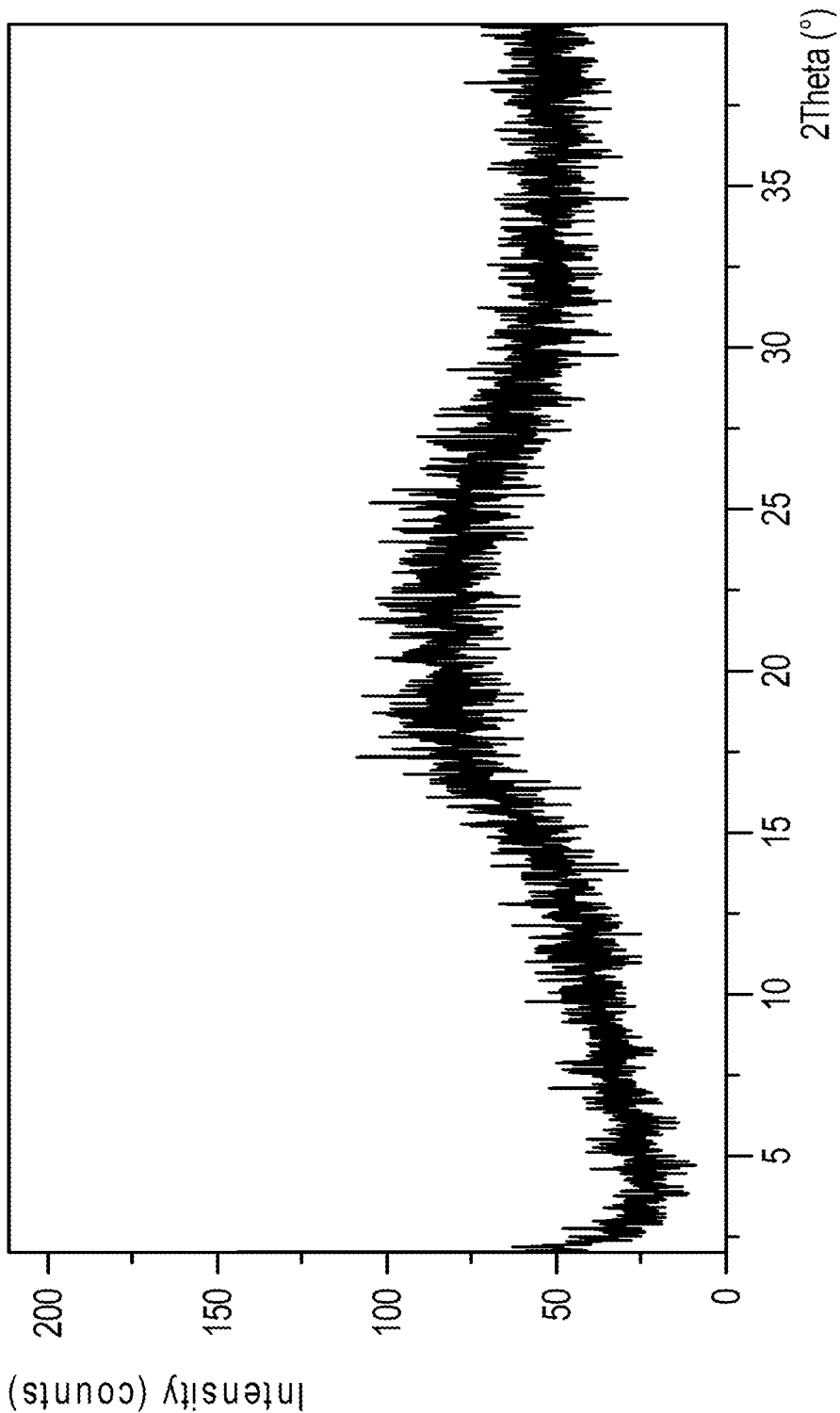
FIG. 30 provides an XRPD pattern for amorphous Compound 1.

The amorphous form of Compound 1 can be prepared according to WO 2019/222112. It was also prepared by converting the Na salt Form 1 of Compound 1 to the amorphous free acid in a DCM/water system at about pH 5.5 adjusted with HCl. The organic layer was evaporated to dryness using a rotary evaporator. The XRPD pattern of amorphous Compound 1 is shown in FIG. 30 and is characterized by an amorphous halo.

B. Compound 1—Polymorph Form I ("Form I")

Method 1: Crude Compound 1, which can be prepared according to WO 2019/222112, (600 mg) was suspended in acetone (20 mL) and heated to about 60° C. in thermowell. After a solution was observed, the contents were filtered through a 0.45 m syringe filter into a clean flask and heated to about 60° C. Once at this temperature, the heating was turned off. The contents were allowed to cool to ambient temperature with agitation. After reaching ambient temperature, the contents were aged for about 24 h. Solids were collected by vacuum filtration and washed 2× acetone (1.2 mL). The solids were dried under reduced pressure at about 70° C. for about 24 h to afford Form I.

Method 2: Crude Compound 1, which can be prepared according to WO 2019/222112, (about 3 g) was dissolved in EtOAc (about 24 mL) at about 60° C., followed by the slow addition (over about 2 h) of EtOH (about 36 mL) and then cooling to about 20° C. over about 4 h. The obtained slurry was stirred at about 20° C. over about 20 h. Solids were isolated by vacuum filtration, washed with 2:3 EtOAc/EtOH (about 6 mL), and dried under vacuum at about 60° C. with nitrogen sweep for about 24 h to afford Form I (about 2.6 g).

Method 3: Crystallization of crude Compound 1 in acetone provided purge of the Z-isomer of Compound 1, followed by crystallization from EtOAc/EtOH (2:3) to afford purified Form I.

Method 4: Form I was also obtained from the slurry experiments the Na Salt of Compound 1. For example, the Na Salt Form 1 of Compound 1 (about 10 mg) and about 2 mL of pH 2 sodium phosphate buffer (50 mM sodium phosphate monobasic solution adjusted to pH 2 with phosphoric acid) were added to a scintillation vial, followed by slow addition of about 2 mL of acetonitrile. A slurry was formed and stirred overnight with a magnetic stir bar. Solids were isolated by centrifuge filtration and dried at ambient temperature to afford Form I. Form I was also prepared from the slurries of the Na Salt of Compound 1 in MeCN/water at pH 2 using different acids for the pH adjustment such as HCl, phosphoric acid, MSA, and p-TSA.

Method 5: Form I was also obtained from EtOH, IPA, acetone, MEK, MIBK, THF, DCM, and di-butyl ether by slurrying amorphous Compound 1 (about 20-30 mg) in about 0.5 mL of the chosen solvent at ambient temperature for up to about 2 weeks. Isolated wet solids were isostructural solvated forms, which after vacuum drying at about 50-100° C. converted to Form I. It was noted that Form I tends to retain non-stoichiometric amount of residual solvents or water due to void volumes in the crystal lattice.

Slurry Methods: Competitive slurries of Form I with the other polymorph forms discussed and prepared below (i.e., Form II, Form III and Form IV) in EtOH showed full conversion to Form I in all cases, suggesting higher stability of Form I compared to all other unsolvated/desolvated forms at these conditions.

Figure 31:
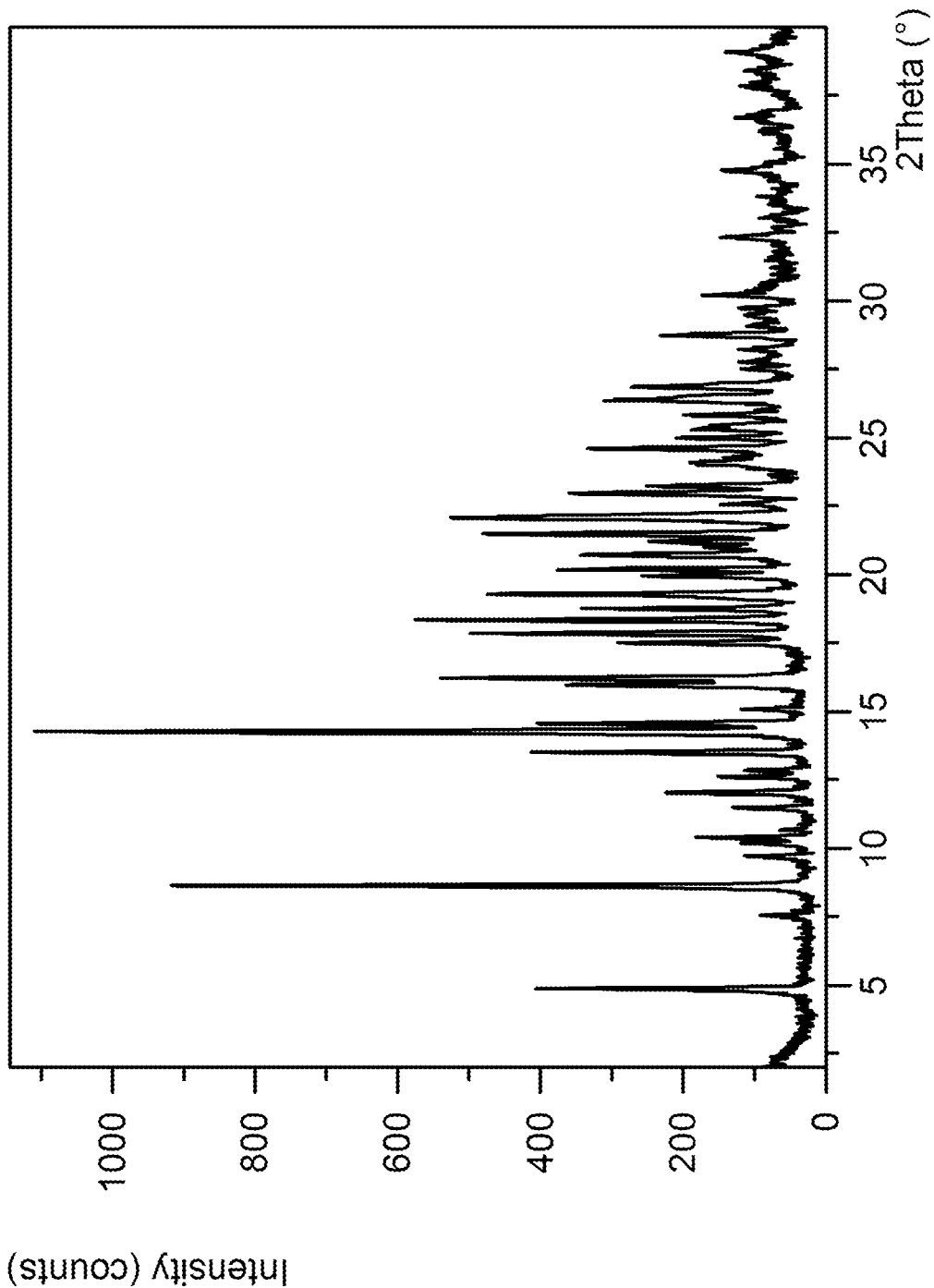
FIG. 31 provides an XRPD pattern for Compound 1—Polymorph Form I.

Characterization: The XRPD pattern of Form I is shown in FIG. 31, and is characterized by sharp reflections, indicating crystallinity. Table 9a shows characteristic peaks of Form I. Table 9b shows extended peak list of Form I.

TABLE 9a

List of characteristic peaks of Form I

| Pos. [°2 Th.] | Rel. Int. [%] |
|---|---|
| 4.9 | 36 |
| 8.6 | 86 |
| 14.3 | 100 |
| 18.3 | 48 |
| 16.2 | 47 |
| 22.1 | 43 |
| 17.8 | 42 |
| 19.3 | 40 |
| 21.5 | 39 |

TABLE 9b

Extended peak list of Form I

| Pos. [°2 Th.] | Rel. Int. [%] |
|---|---|
| 4.9 | 36 |
| 8.6 | 86 |
| 13.5 | 36 |
| 14.3 | 100 |
| 14.6 | 35 |
| 16.0 | 31 |
| 16.2 | 47 |
| 17.5 | 23 |
| 17.8 | 42 |
| 18.3 | 48 |
| 18.8 | 25 |
| 19.3 | 40 |
| 20.2 | 28 |
| 20.7 | 24 |
| 21.5 | 39 |
| 22.1 | 43 |
| 23.0 | 28 |
| 24.6 | 26 |
| 26.3 | 20 |
| 26.8 | 19 |

Figure 32:
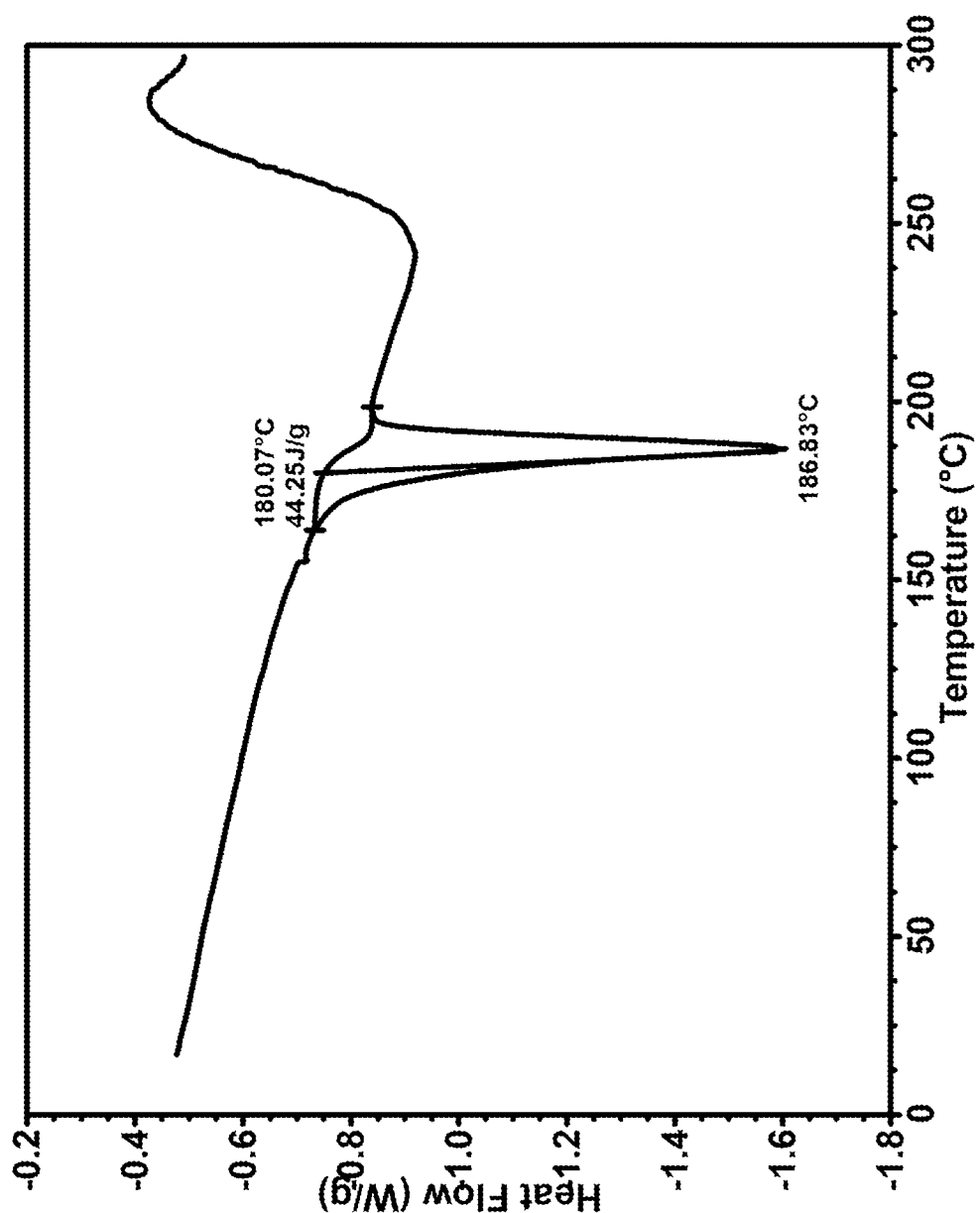
FIG. 32 provides a DSC thermogram for Compound 1—Polymorph Form I.
Figure 33:
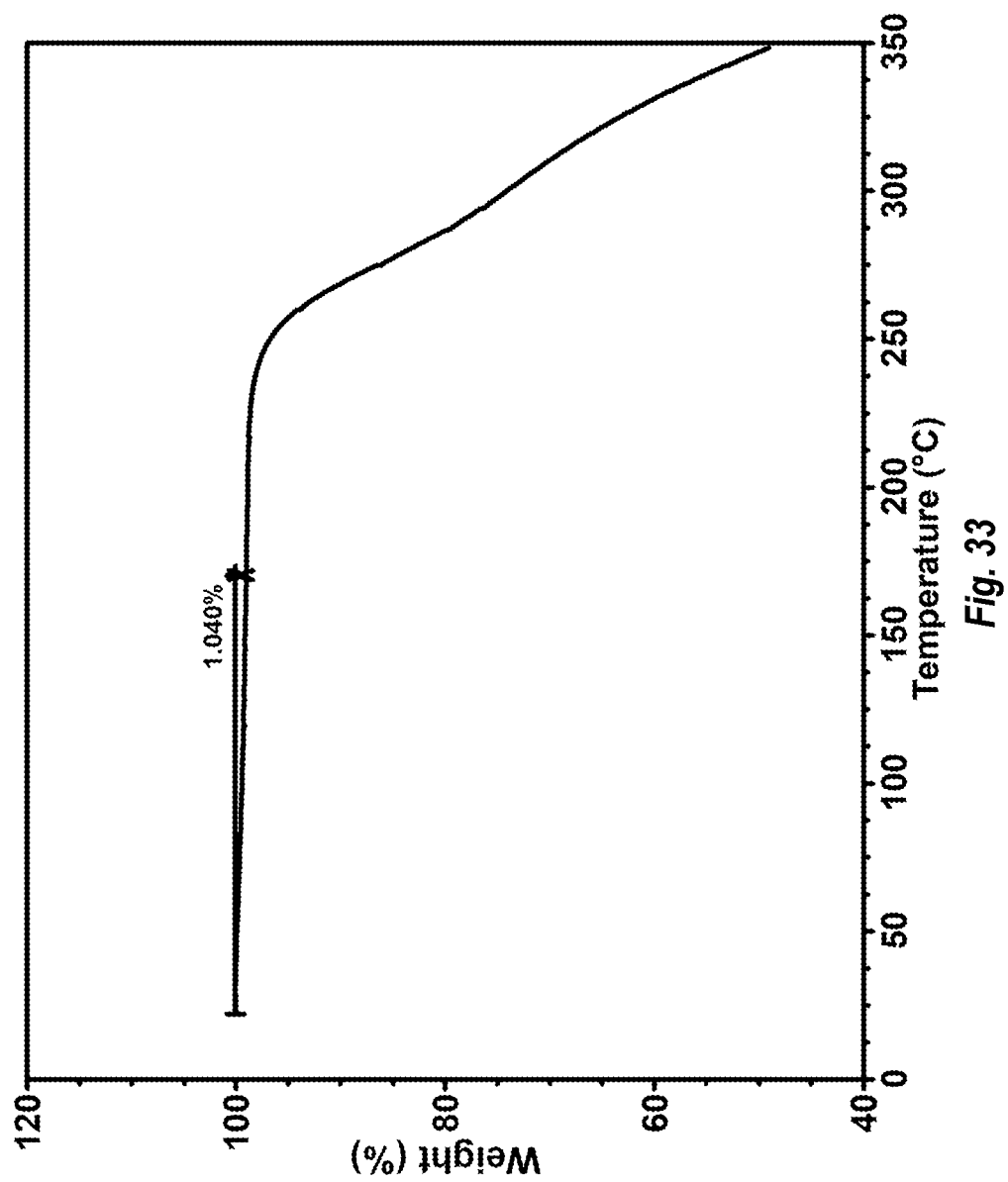
FIG. 33 provides a TGA thermogram for Compound 1—Polymorph Form I.

The DSC thermogram of Form I is shown in FIG. 32. The DSC data shows an endothermic event with an onset temperature at about 180° C. The TGA thermogram of Form I is shown in FIG. 33. The continuous weight loss of about 1.0% was observed from ambient temperature to about 170° C. most likely corresponds to the residual solvent.

DVS analysis (FIG. 34) shows that Form I is slightly hygroscopic, absorbing about 1.4 wt % water at about 25° C. and between 0% and 90% RH. XRPD analysis of the sample post DVS showed no form change.

Figure 35:
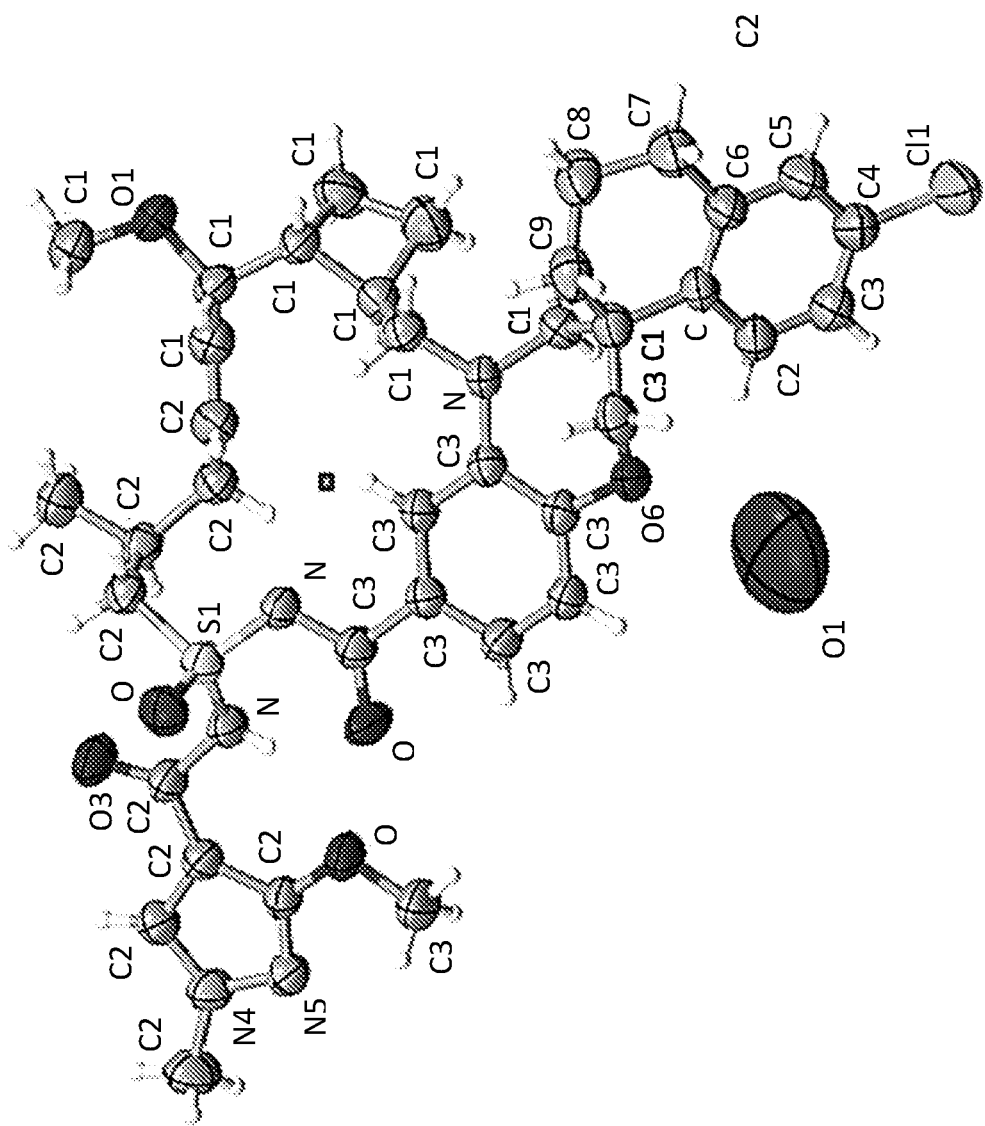
FIG. 35 provides single crystal X-ray structure of Compound 1—Polymorph Form I. C=carbon atom, Cl=chloride atom, O=oxygen atom, N=nitrogen atom.

The single crystal structure of Form I was solved and confirms the presence of one molecule of Compound 1 and half molecule of water. However, the water molecule is disordered on and around the 2-fold axis. No intermolecular hydrogen bonds are observed. The N2 hydrogen forms intramolecular hydrogen bonds to O4 and O5, and the water does not appear to form hydrogen bonds. The orthorhombic cell dimensions at room temperature are shown in Table 9c, and the diagram of the single crystal structure is shown in FIG. 35. Calculated XRPD pattern is consistent with experimental XRPD pattern of Form I.

TABLE 9c

Form I Single Crystal Structure Unit Cell Dimensions at Room Temperature

| Unit Cell Dimension | Value |
|---|---|
| a [Å] | 36.6499(10) |
| b [Å] | 12.4742(3) |
| c [Å] | 8.5346(2) |
| α [°] | 90 |
| β [°] | 90 |
| γ [°] | 90 |
| V [Å$^3$] | 3901.83(18) |

C. Compound 1—Polymorph Form II ("Form II")

Method 1: Form II is a desolvated form. It was prepared by adding a solution of about 1.1 equivalent of HCl in about 0.5 mL water into the slurry of the Na Salt Form 1 of Compound 1 (about 100 mg) in about 0.5 mL MeCN. The slurry was stirred at ambient conditions for about 16 h. The obtained solids were isolated by filtration and dried under vacuum at about 50° C. for about 24 h to afford Form II.

Method 2: Form II was also obtained after drying of the MeCN solvate of Compound 1 (prepared below) under vacuum at about 50° C.

Figure 36:
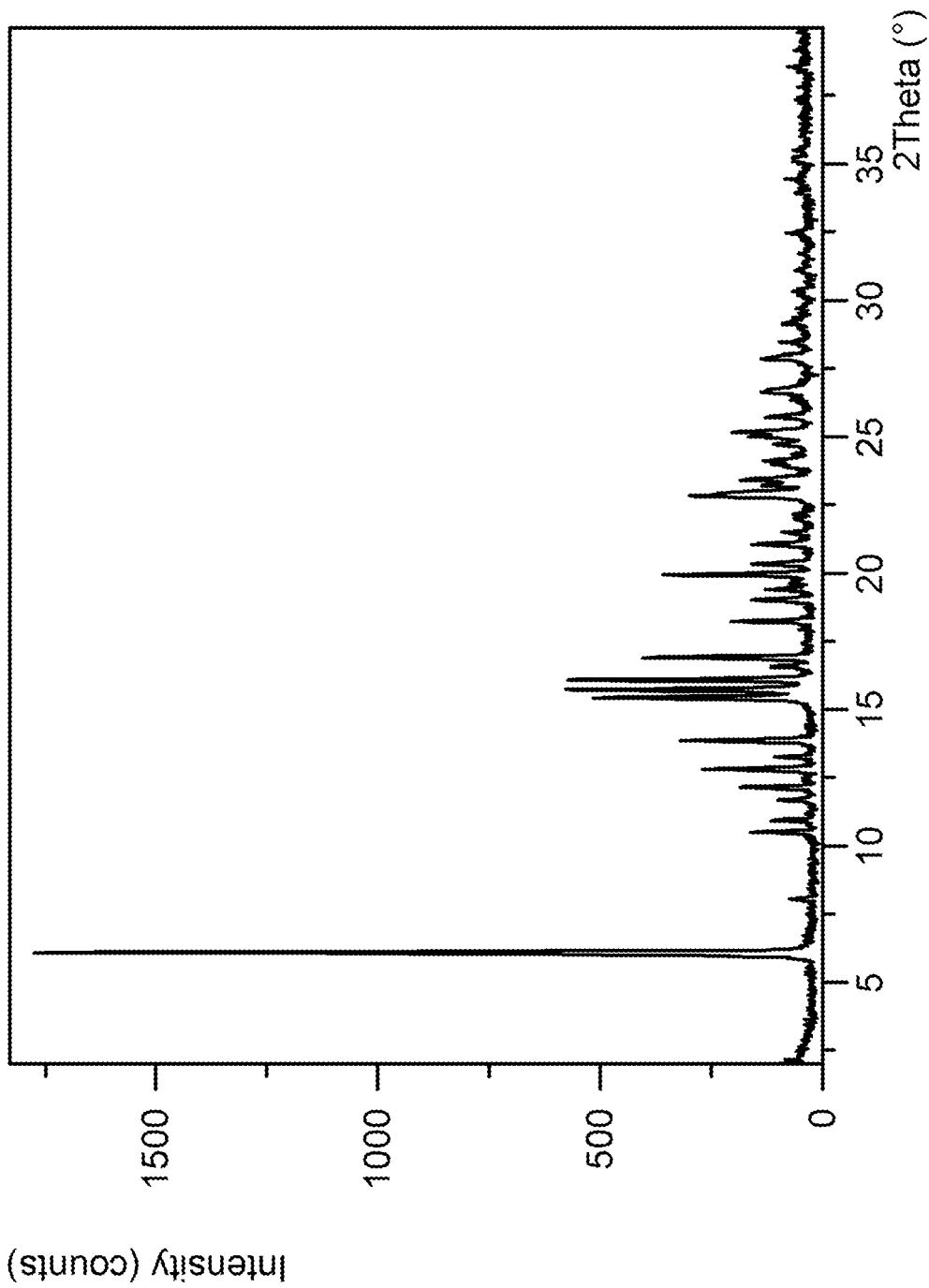
FIG. 36 provides an XRPD pattern for Compound 1—Polymorph Form II.

Characterization: The XRPD pattern of Form II is shown in FIG. 36, and is characterized by sharp reflections, indicating crystallinity. Table 10a shows characteristic peaks of Form II. Table 10b shows extended peak list of Form II.

TABLE 10a

List of characteristic peaks of Form II

| Pos. [°2 Th.] | Rel. Int. [%] |
|---|---|
| 6.1 | 100 |
| 15.7 | 31 |
| 16.1 | 31 |
| 15.4 | 27 |
| 16.9 | 21 |
| 19.9 | 18 |
| 12.8 | 13 |
| 13.9 | 16 |
| 22.8 | 15 |

TABLE 10b

Extended peak list of Form II

| Pos. [°2 Th.] | Rel. Int. [%] |
|---|---|
| 6.1 | 100 |
| 10.5 | 8 |
| 12.2 | 8 |
| 12.8 | 13 |
| 13.3 | 5 |
| 13.9 | 16 |
| 15.4 | 27 |
| 15.7 | 31 |
| 16.1 | 31 |
| 16.9 | 21 |
| 18.2 | 9 |
| 19.0 | 7 |
| 19.4 | 5 |
| 19.9 | 18 |
| 20.3 | 7 |
| 21.1 | 7 |
| 22.8 | 15 |
| 23.4 | 8 |
| 25.2 | 9 |
| 25.7 | 5 |
| 26.7 | 5 |
| 27.9 | 5 |

Figure 37:
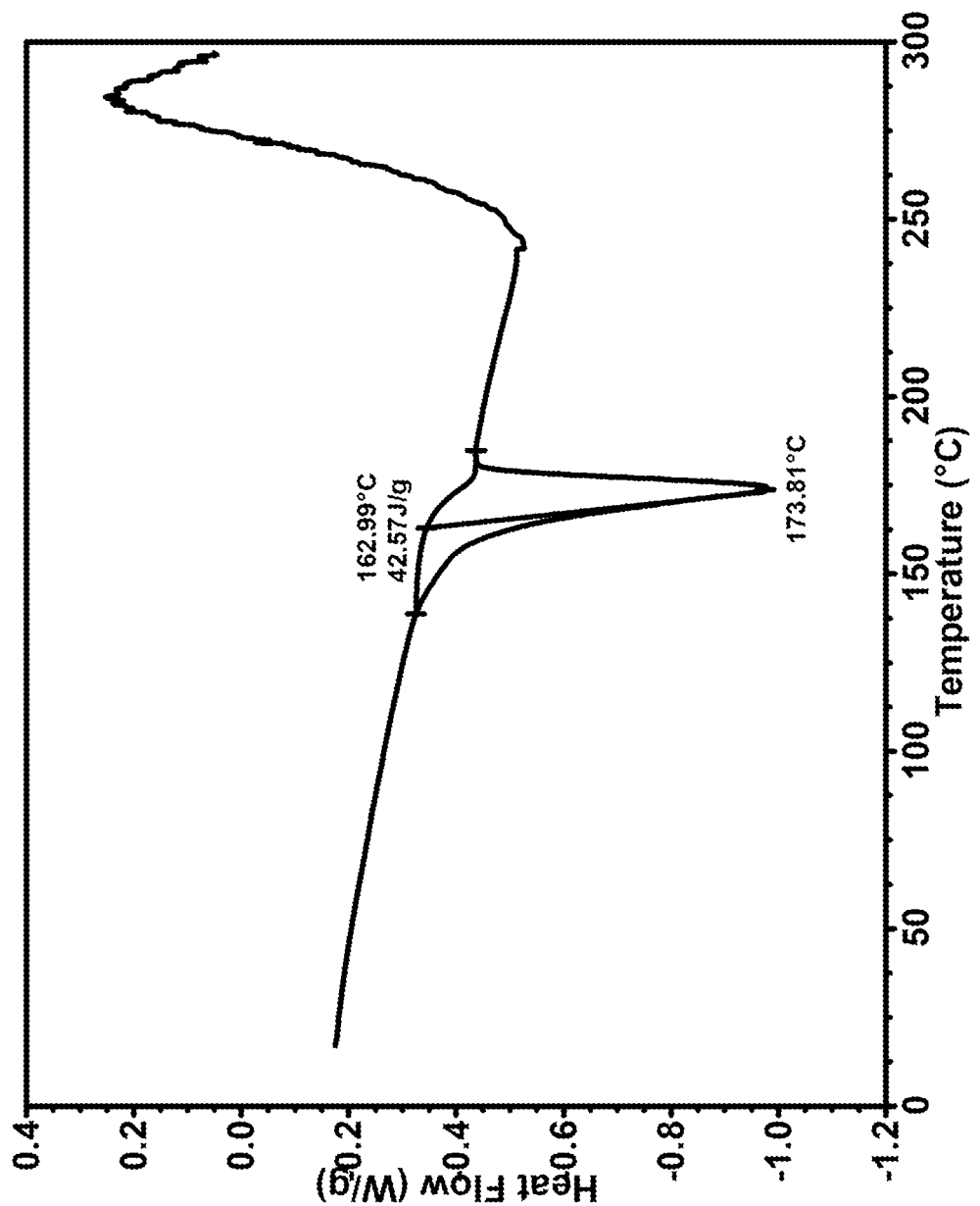
FIG. 37 provides a DSC thermogram for Compound 1—Polymorph Form II.
Figure 38:
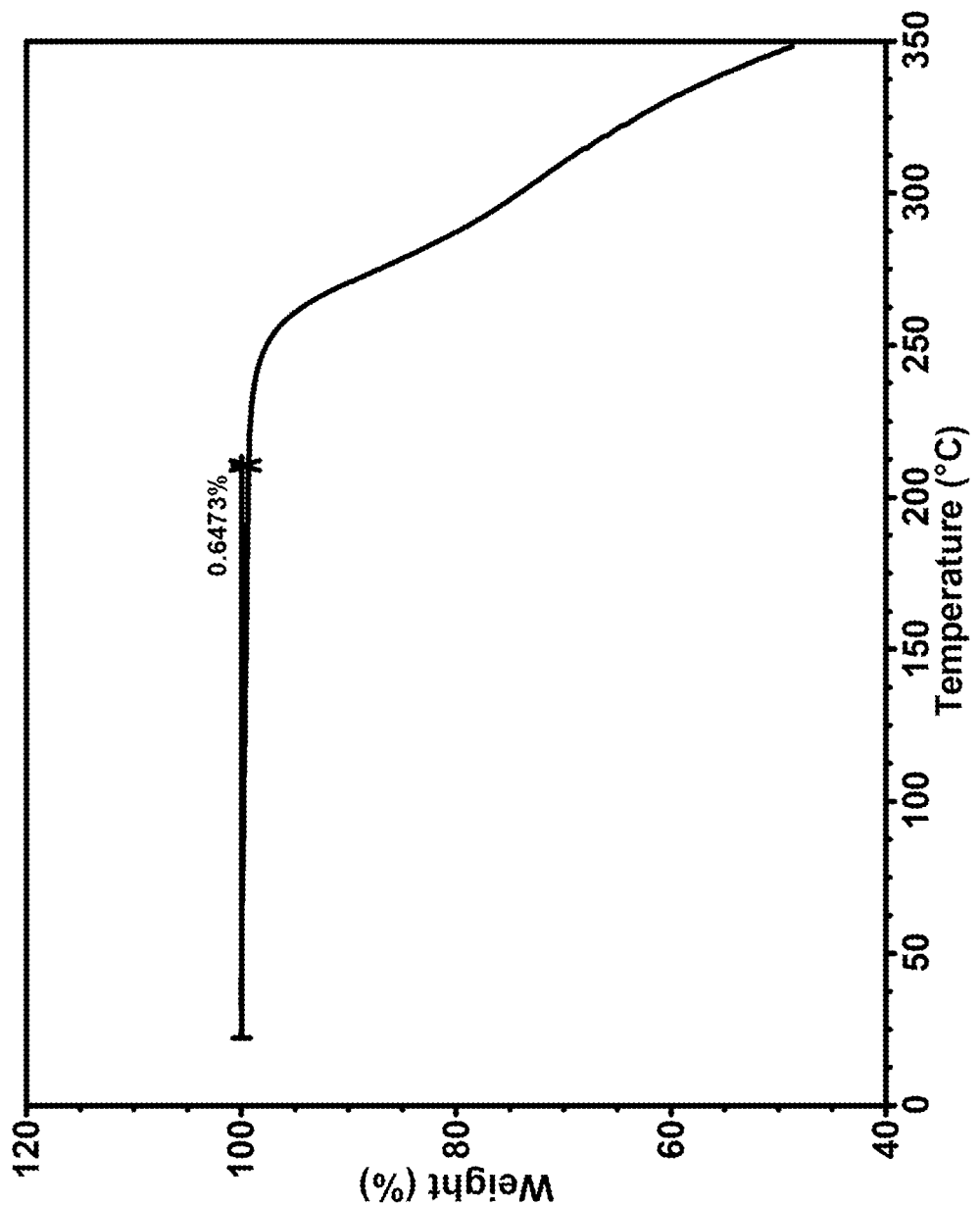
FIG. 38 provides a TGA thermogram for Compound 1—Polymorph Form II.

The DSC thermogram of Form II is shown in FIG. 37. The DSC data shows an endothermic event with an onset temperature at about 163° C. attributed to the melt of Form II. The TGA thermogram of Form II is shown in FIG. 38. The continuous weight loss of about 0.6% was observed from ambient temperature to about 210° C. and most likely corresponds to the residual solvent. DVS analysis (FIG. 39) shows that Form II is slightly hygroscopic, absorbing up to about 1.1 wt % water at about 25° C. and between 0% and 90% RH. XRPD analysis of the sample post DVS showed no form change.

D. Compound 1—Polymorph Form III ("Form III")

Method 1: Form III is a desolvated form. Form III was prepared during a co-crystal study of the Na Salt Form 1 of Compound 1 in MeOH with oxalic acid, phosphoric acid, citric acid, malic acid, and malonic acid. Each vial was charged with the Na Salt (about 60-70 mg) and about 1 mL of MeOH, followed by the addition of about 1.1 eq. co-former, followed by stirring at about 50° C. for about 30 min and then at ambient temperature for about 16 h. Solids were isolated by filtration and dried under vacuum at about 50° C. to afford Form III.

Figure 40:
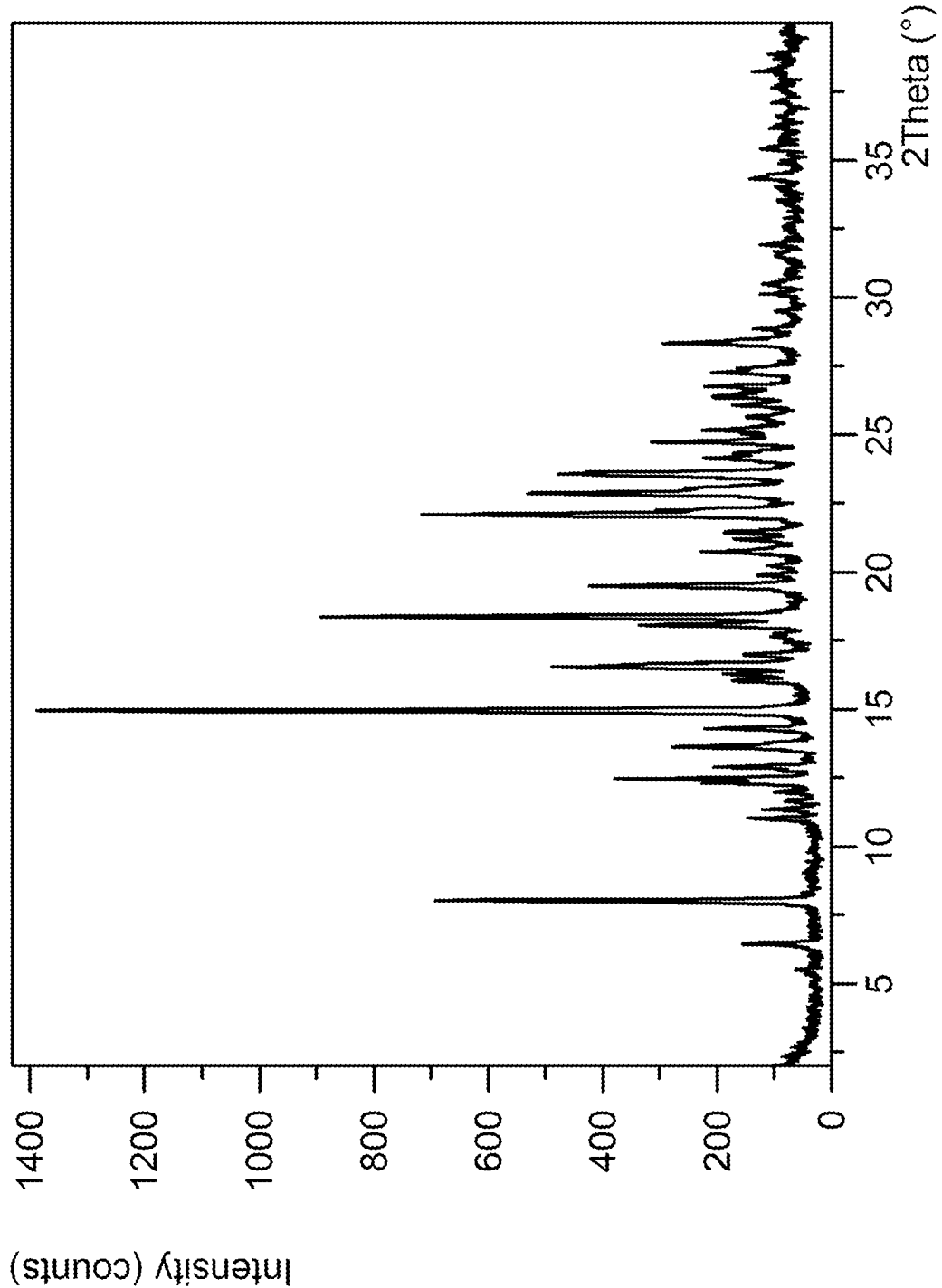
FIG. 40 provides an XRPD pattern for Compound 1—Polymorph Form III.

Method 2: Form III was also obtained after drying of the MeOH solvate of Compound 1 (prepared below) under vacuum at about 50° C. The XRPD pattern of Form III is shown in FIG. 40, and is characterized by sharp reflections, indicating crystallinity. Table 11a shows characteristic peaks of Form III. Table 11b shows extended peak list of Form III.

TABLE 11a

List of characteristic peaks of Form III

| Pos. [°2 Th.] | Rel. Int. [%] |
|---|---|
| 8.0 | 46 |
| 15.0 | 100 |
| 18.4 | 60 |
| 16.5 | 31 |
| 22.1 | 46 |
| 22.9 | 33 |
| 12.5 | 24 |
| 19.5 | 26 |
| 23.6 | 27 |

TABLE 11b

Extended peak list of Form III

| Pos. [°2 Th.] | Rel. Int. [%] |
|---|---|
| 6.5 | 10 |
| 8.0 | 46 |
| 12.3 | 12 |
| 12.5 | 24 |
| 12.9 | 11 |
| 13.6 | 17 |
| 14.3 | 12 |
| 15.0 | 100 |
| 16.0 | 9 |
| 16.5 | 31 |
| 18.1 | 19 |
| 18.4 | 60 |
| 19.5 | 26 |
| 20.7 | 10 |
| 22.1 | 46 |
| 22.9 | 33 |
| 23.6 | 27 |
| 24.1 | 9 |
| 24.7 | 17 |

TABLE 11b-continued

Extended peak list of Form III

| Pos. [°2 Th.] | Rel. Int. [%] |
|---|---|
| 26.8 | 10 |
| 28.3 | 15 |

Figure 41:
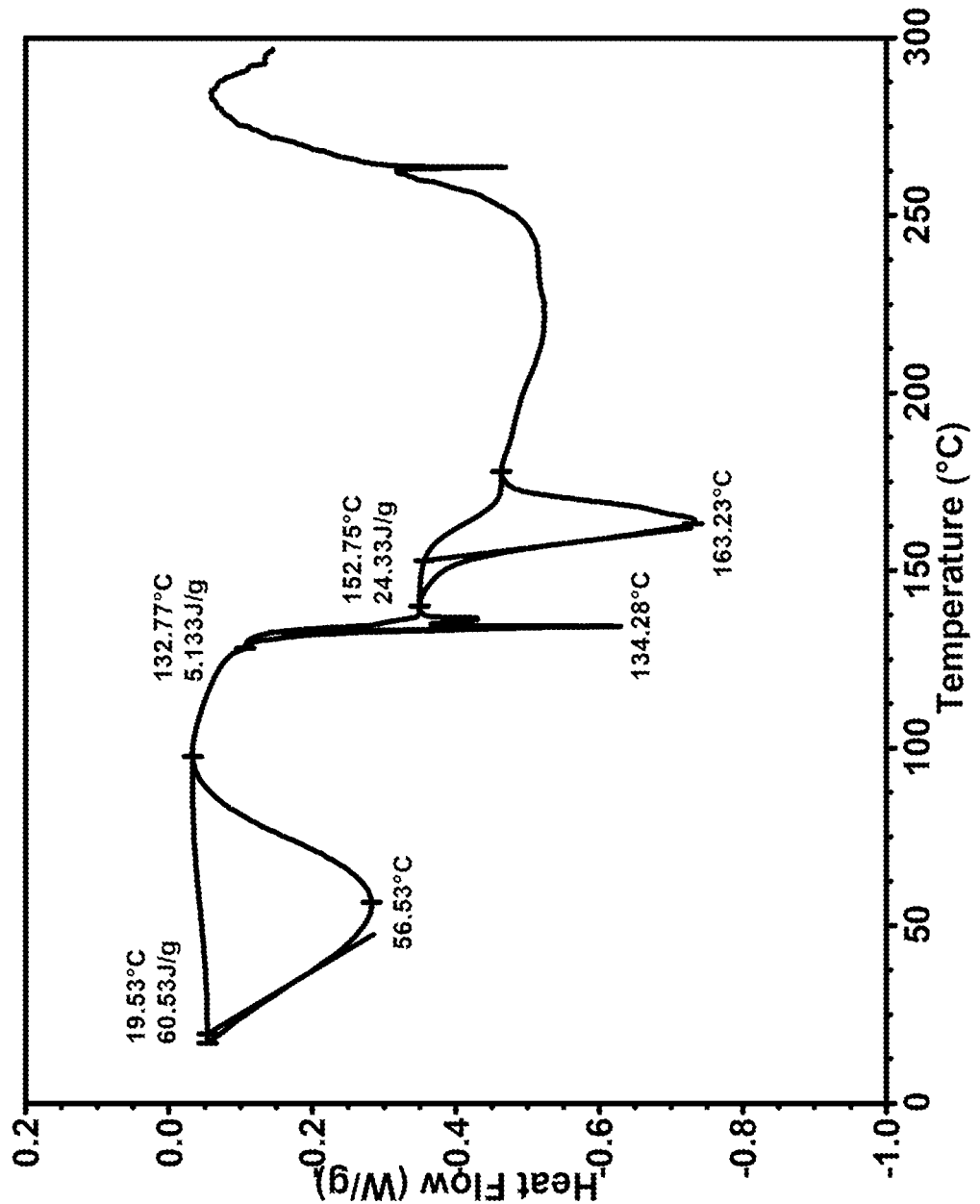
FIG. 41 provides a DSC thermogram for Compound 1—Polymorph Form III.
Figure 42:
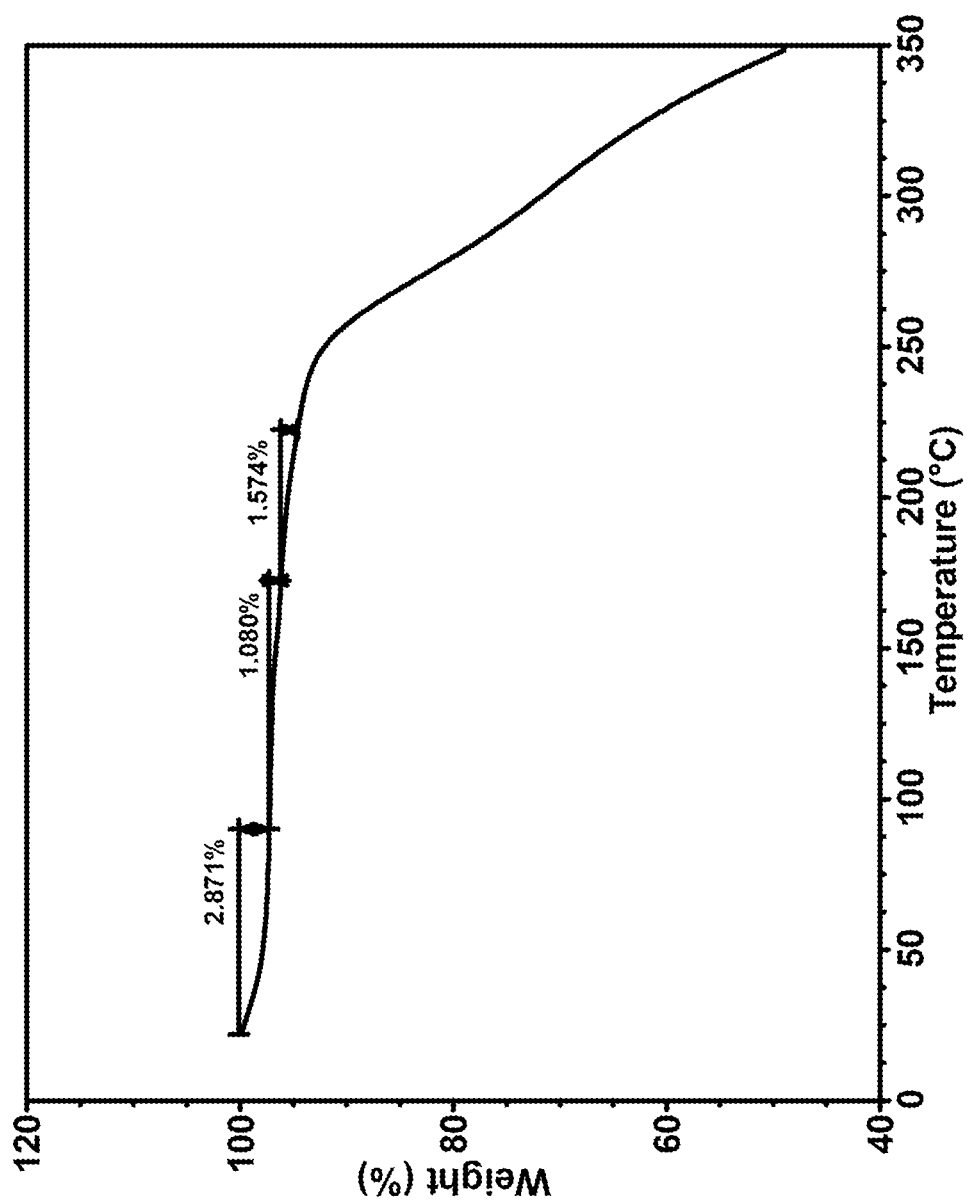
FIG. 42 provides a TGA thermogram for Compound 1—Polymorph Form III.

The DSC thermogram of Form III is shown in FIG. 41. The DSC data shows three endothermic events with onset temperatures at about 20° C., about 133° C., and about 153° C. The TGA thermogram of Form III is shown in FIG. 42. TGA thermogram shows weight loss of about 2.9% below about 90° C., weight loss of about 1.1% at about 90-175° C., and weight loss of about 1.6% at about 175-225° C. most likely corresponding to the residual solvents. DVS analysis (FIG. 43) shows that Form III is moderately hygroscopic, absorbing up to about 5 wt % water at about 25° C. and between 0% and 90% RH. XRPD analysis of Form III post DVS showed no form change.

E. Compound 1—Polymorph Form IV ("Form IV")

Figure 44:
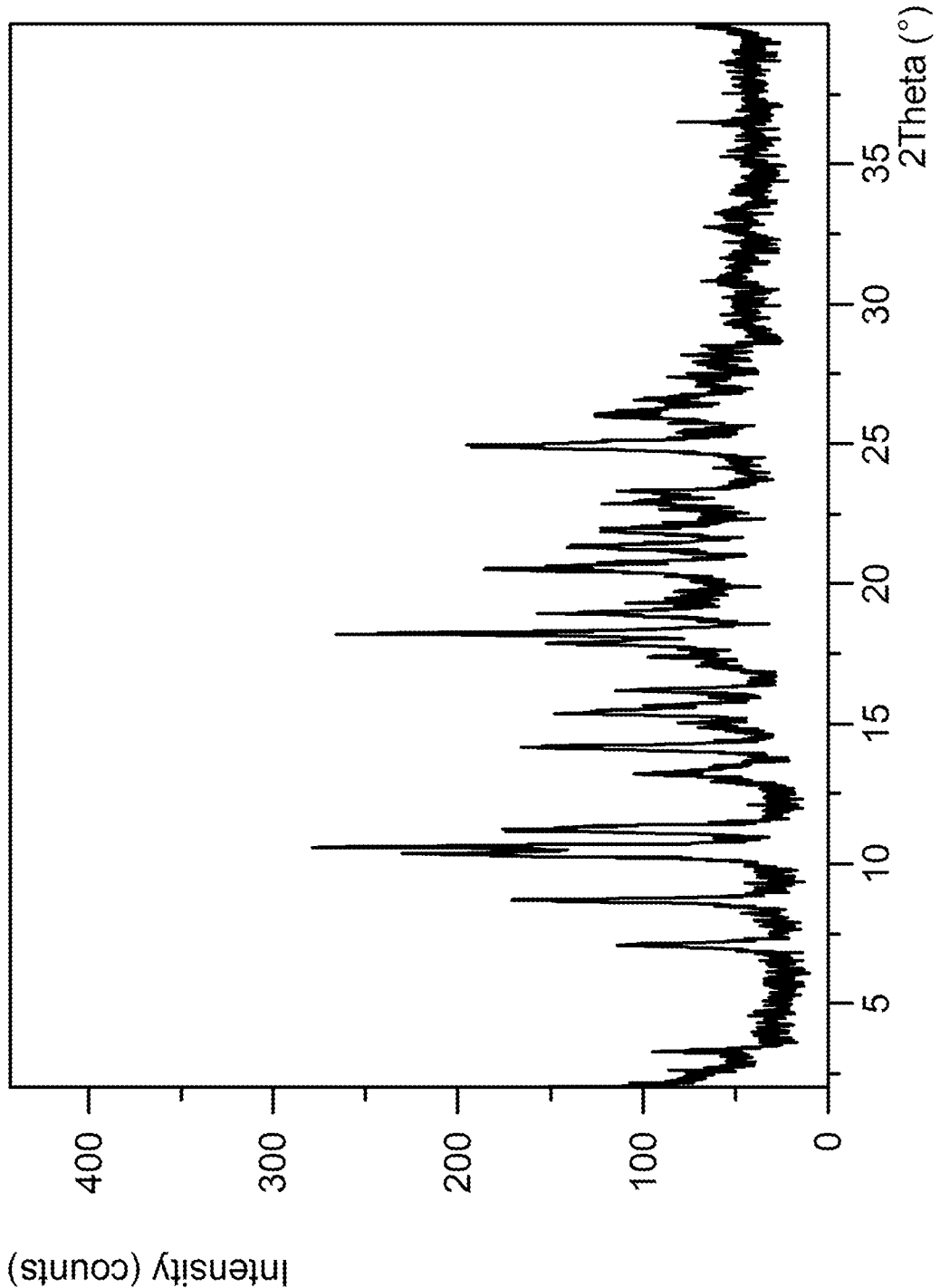
FIG. 44 provides an XRPD pattern for Compound 1—Polymorph Form IV.

Form IV is a desolvated form and was prepared by slurrying amorphous Compound 1 in EtOH for about 16 h or in heptane for about 2 weeks at ambient temperature. The XRPD pattern of Form IV is shown in FIG. 44, and is characterized by sharp reflections, indicating crystallinity. Table 12a shows characteristic peaks of Form IV. Table 12b shows extended peak list of Form IV.

TABLE 12a

List of characteristic peaks of Form IV

| Pos. [°2 Th.] | Rel. Int. [%] |
|---|---|
| 7.1 | 35 |
| 8.7 | 62 |
| 10.6 | 100.0 |
| 10.3 | 76 |
| 11.2 | 62 |
| 18.2 | 79 |
| 14.2 | 53 |
| 20.5 | 46 |
| 24.9 | 59 |

TABLE 12b

Extended peak list of Form IV

| Pos. [°2 Th.] | Rel. Int. [%] |
|---|---|
| 3.3 | 14 |
| 7.1 | 35 |
| 8.7 | 62 |
| 10.3 | 76 |
| 10.6 | 100.0 |
| 11.2 | 62 |
| 13.2 | 28 |
| 14.2 | 53 |
| 15.4 | 42 |
| 16.2 | 27 |
| 17.9 | 42 |
| 18.2 | 79 |
| 19.0 | 35 |
| 20.5 | 46 |
| 21.3 | 31 |
| 21.9 | 27 |
| 23.3 | 27 |
| 24.9 | 59 |
| 26.1 | 26 |
| 28.3 | 8.5 |

Figure 45:
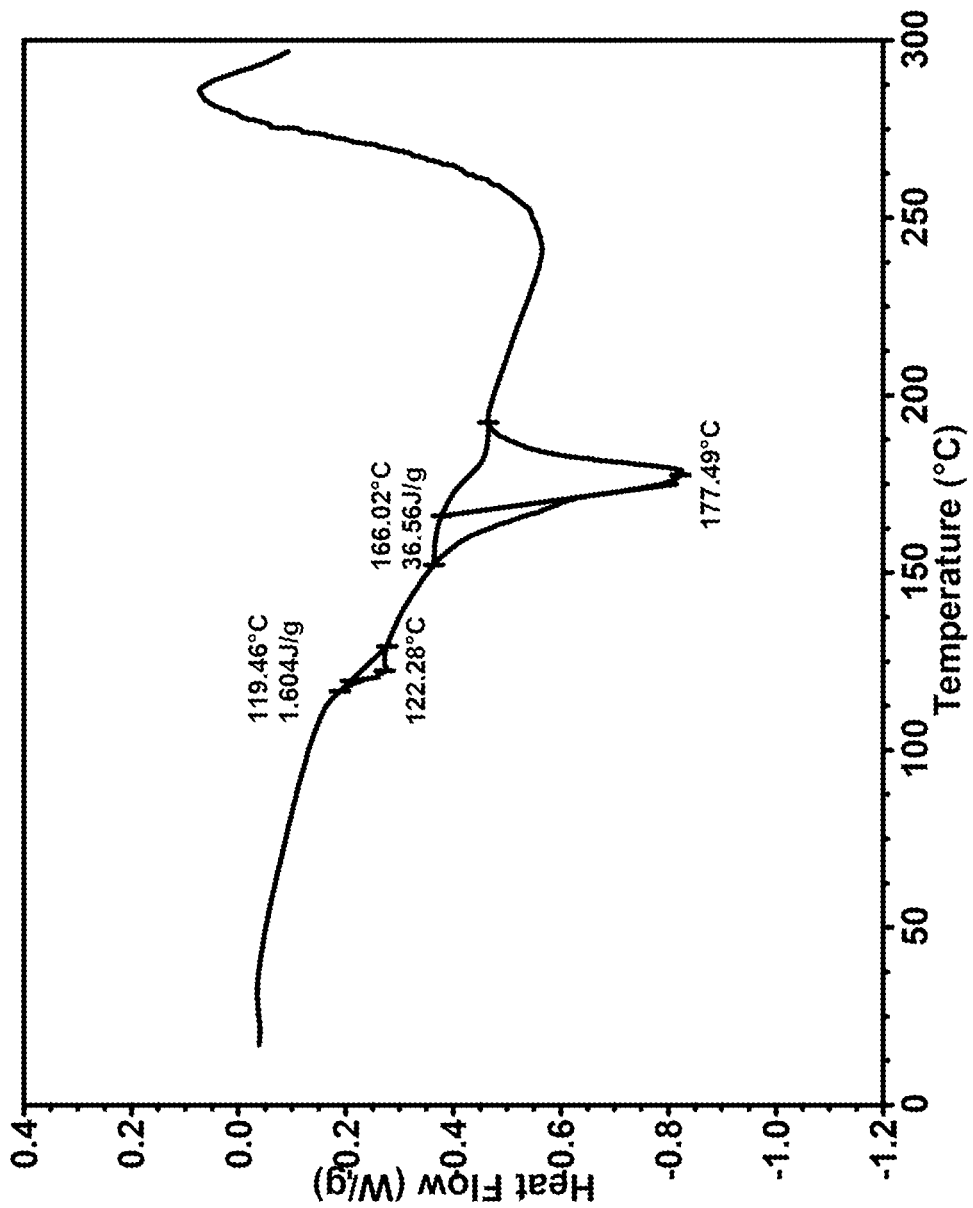
FIG. 45 provides a DSC thermogram for Compound 1—Polymorph Form IV.
Figure 46:
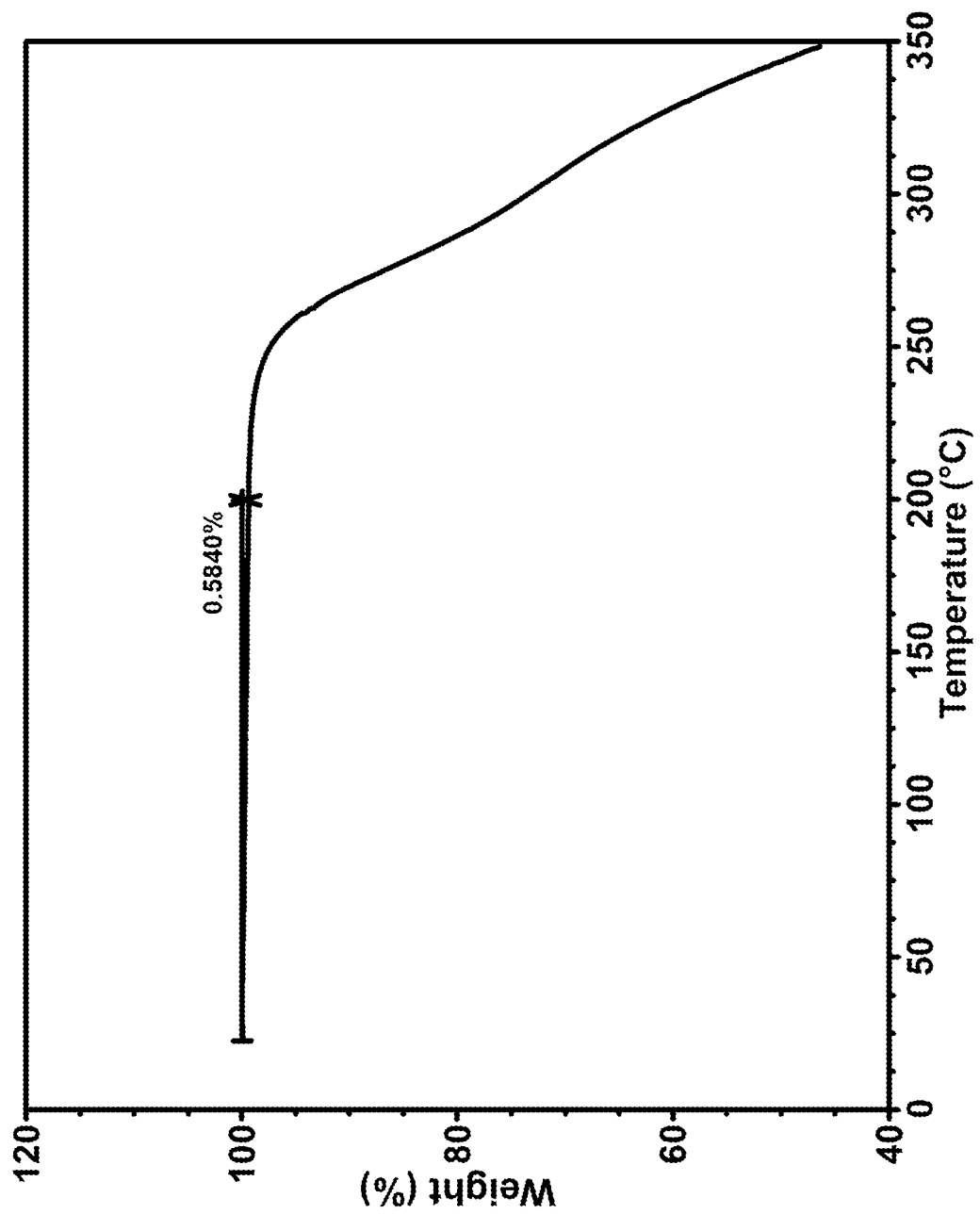
FIG. 46 provides a TGA thermogram for Compound 1—Polymorph Form IV.

The DSC thermogram of Form IV is shown in FIG. 45. The DSC data shows two endothermic events with an onset temperature at about 119° C. and about 166° C. The TGA thermogram of Form IV is shown in FIG. 46. TGA thermogram shows continuous weight loss at about 0.6% below about 200° C. most likely corresponding to the residual solvent.

F. Compound 1—MeCN Solvate

The MeCN solvate of Compound 1 was obtained by slurrying amorphous Compound 1 (prepared according to WO 2021/108254) in MeCN. The XRPD pattern of MeCN solvate is shown in FIG. 47, and is characterized by sharp reflections, indicating crystallinity.

G. Compound 1—MeOH Solvate

The MeOH solvate of Compound 1 was obtained by slurrying amorphous Compound 1 (prepared according to WO 2021/108254) in MeOH. The XRPD pattern of MeOH solvate is shown in FIG. 48, and is characterized by sharp reflections, indicating crystallinity.

H. Compound 1—EtOAc Solvate

The EtOAc solvate of Compound 1 was obtained by slurrying Form I in EtOAc. The XRPD pattern of EtOAc solvate is shown in FIG. 49, and is characterized by sharp reflections, indicating crystallinity. After drying at about 50° C. for about 24 h, the EtOAc solvate partially converted to potential desolvated form as shown in FIG. 50.

I. Compound 1—MeTHF Solvate

The MeTHF solvate of Compound 1 was obtained by slurrying Form I in 2-MeTHF at ambient temperature. The XRPD pattern of 2-MeTHF solvate is shown in FIG. 51, and is characterized by sharp reflections, indicating crystallinity.

J. Compound 1—Toluene Solvate

The toluene solvate of Compound 1 was obtained by slurrying Form I in toluene at ambient temperature. The XRPD pattern of the toluene solvate is shown in FIG. 52, and is characterized by sharp reflections, indicating crystallinity. The toluene solvate converted to disordered desolvated form after drying under vacuum at about 50° C.

K. Compound 1—nBuOAc Solvate

The n-BuOAc solvate of Compound 1 was obtained by slurrying Form I in n-BuOAc at ambient temperature. The XRPD pattern of n-BuOAc solvate is shown in FIG. 53, and is characterized by sharp reflections, indicating crystallinity. The n-BuOAc solvate converted to disordered desolvated form after drying under vacuum at about 50° C.

L. Compound 1—MTBE Solvate 1

A first MTBE solvate ("MTBE Solvate 1") was obtained by slurrying Form I in MTBE. The XRPD pattern of MTBE Solvate 1 is shown in FIG. 54, and is characterized by sharp reflections, indicating crystallinity.

M. Compound 1—MTBE Solvate 2

A second MTBE solvate ("MTBE Solvate 2") was obtained by slurrying Form I in MTBE. The XRPD pattern of MTBE Solvate 2 is shown in FIG. 55, and is characterized by sharp reflections, indicating crystallinity.

N. Compound 1—Isopropanol Hemi-Solvate

The isopropanol hemi-solvate of Compound 1 was obtained by dissolving Form I in EtOAc (about 24 mL) at about 65° C. EtOAc/iPrOH (4:1, about 10 mL) was added, followed by slow addition (over about 2.5 h) of iPrOH (about 46 mL). The reaction was cooled to about 20° C. over about 4 h and subsequently cooled to about 0° C. over about 1.5 h. The obtained slurry was stirred at about 0° C. over about 4 h. Solids were isolated by vacuum filtration, washed with EtOAc/iPrOH (1:2, about 12 mL), and dried under vacuum at about 65° C. with nitrogen sweep for about 45 h to afford Compound 1—Isopropanol Hemi-Solvate. The XRPD pattern of the Isopropanol Hemi-Solvate is shown in FIG. 56, and is characterized by sharp reflections, indicating crystallinity.

Example 3. Isostructural Solvated Forms of Form I

Figure 57:
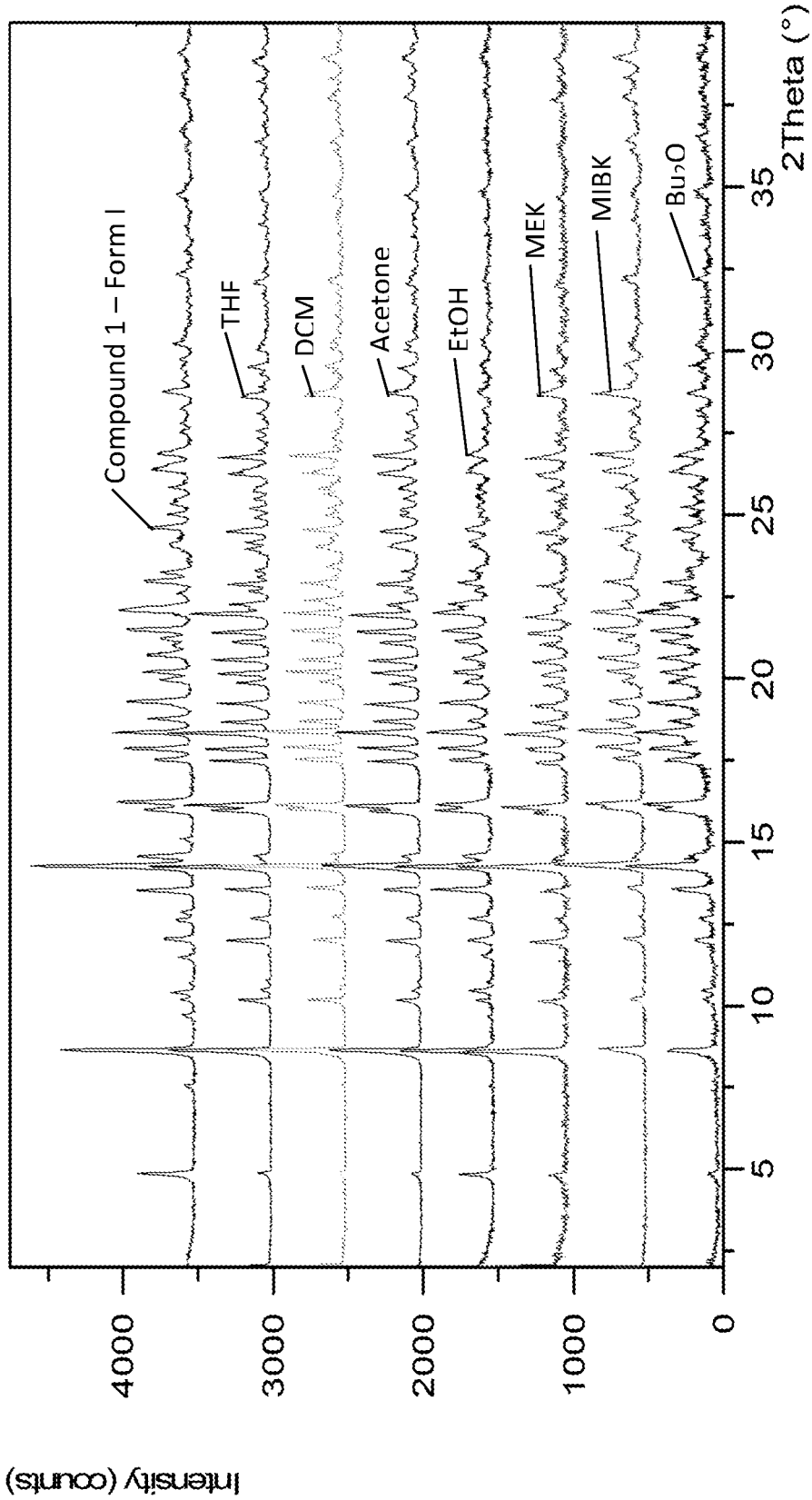
FIG. 57 provides an XRPD pattern for Compound 1—Form I as well as various isostructural forms of Compound 1.
Figure 58:
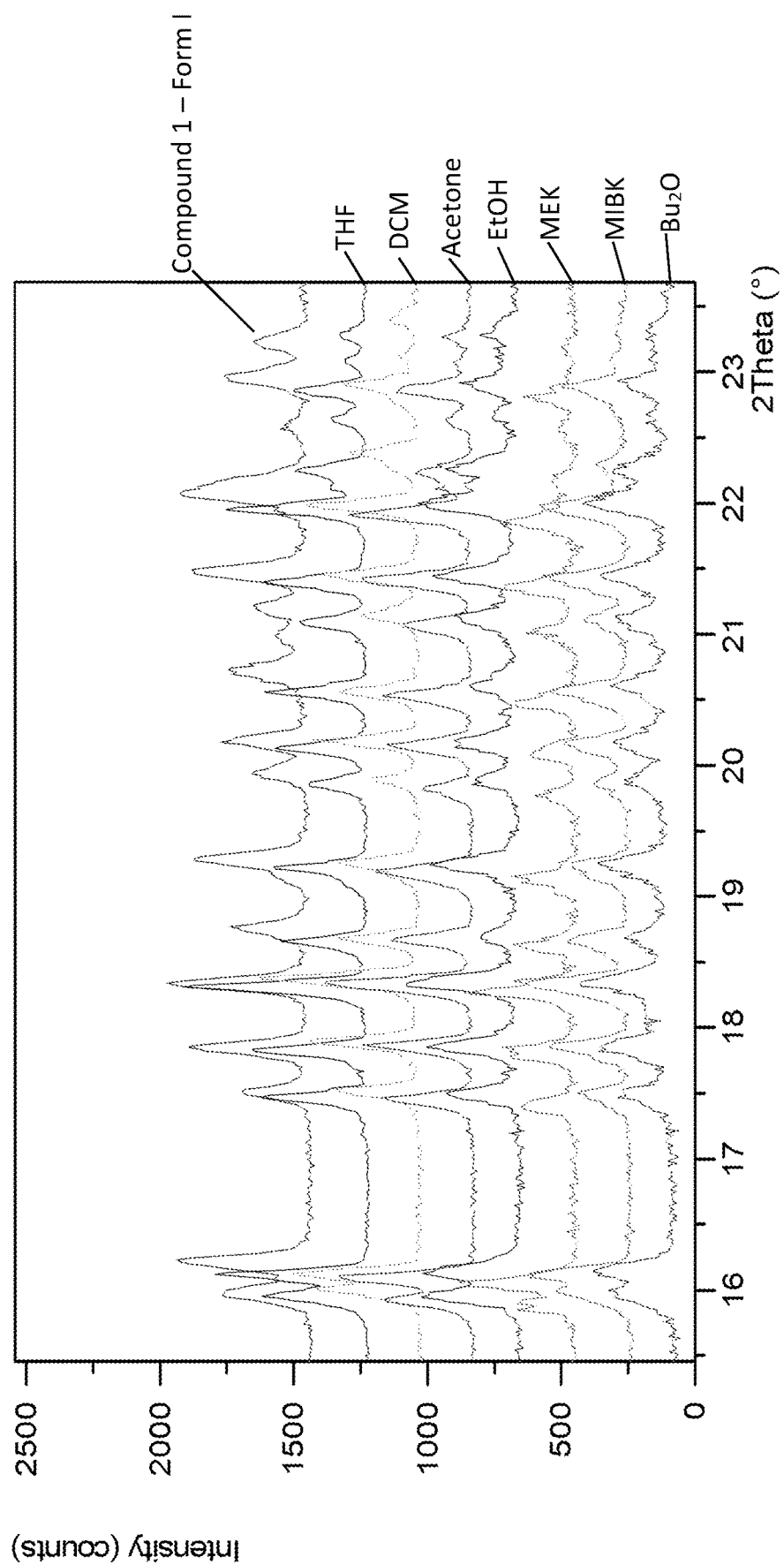
FIG. 58 provides an enlargement of a section of the XRPD pattern disclosed in FIG. 57.

Slurries of Form I of Compound 1 in several solvents, such as acetone, MEK, MIBK, butyl ether ($Bu_2O$), THF, DCM, EtOH and IPA afforded solids with XRPD patterns very similar to Form I with some peak shifts and additional small peaks, suggesting formation of isostructural solvated forms (FIG. 57 and FIG. 58). These isostructural solvates retain non-stoichiometric amounts of residual solvents after drying. However, extensive drying at elevated temperature and reduction of particle size (by grinding and milling) afford Form I, which could still retain small amount of a residual solvent.

Single crystal X-Ray analysis of EtOH solvate and acetone solvate afforded unit cell parameters similar to Form I (Table 13) confirming isostructural nature of these solvates with Form I, which also retains some water inside void volumes of crystal lattice even after drying due to some hygroscopicity.

TABLE 13

Single crystal X-ray data

| Attribute | Hydrate | Ethanol solvate | Acetone solvate |
|---|---|---|---|
| Crystal system | orthorhombic | orthorhombic | orthorhombic |
| Space group | $P2_12_12$ | $P2_12_12$ | $P2_12_12$ |
| Unit cell parameters | a = 36.6499(10) Å | a = 36.3278(5) Å | a = 36.5579(3) Å |
| | $\alpha = 90°$ | $\alpha = 90°$ | $\alpha = 90°$ |
| | b = 12.4742(3) Å | b = 12.35653(18) Å | b = 12.35303(11) Å |
| | $\beta = 90°$ | $\beta = 90°$ | $\beta = 90°$ |
| | c = 8.5346(2) Å | c = 8.51659(13) Å | c = 8.52899(8) Å |
| | $\gamma = 90°$ | $\gamma = 90°$ | $\gamma = 90°$ |
| Unit cell volume (Å$^3$) | 3901.83(18) | 3822.98(10) | 3849.18(6) |
| Cell formula units, Z | 4 | 4 | 4 |
| Calculated density (g/cm$^3$) | 1.267 | 1.314 | 1.321 |

EQUIVALENTS

The foregoing written specification is considered to be sufficient to enable one skilled in the art to practice the embodiments. The foregoing description and Examples detail certain embodiments and describes the best mode contemplated by the inventors. It will be appreciated, however, that no matter how detailed the foregoing may appear in text, the embodiment may be practiced in many ways and should be construed in accordance with the appended claims and any equivalents thereof.

What is claimed is:

1. A crystalline form of Compound

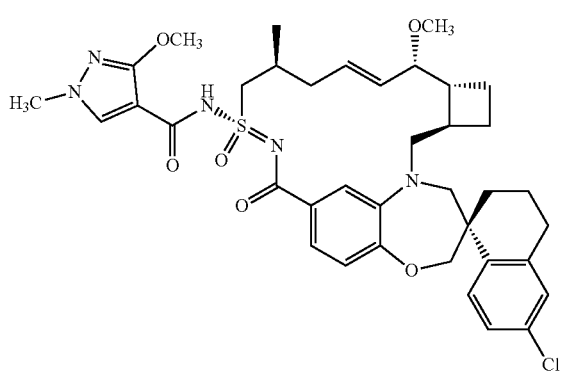

Compound 1 wherein the crystalline form of Compound 1 is characterized by an x-ray powder diffraction pattern comprising peaks at about 4.9°±0.2°, 8.6°±0.2° and 14.3°±0.2° 2-θ.

2. The crystalline form according to claim 1, wherein the x-ray powder diffraction pattern comprises one or more additional peaks selected from peaks at about 16.2°±0.2°, 18.3°±0.2° and 22.1°±0.2° 2-θ.

3. The crystalline form according to claim 1, wherein the x-ray powder diffraction pattern comprises one or more additional peaks selected from peaks at about 17.8°±0.2°, 19.3°±0.2° and 21.5°±0.2° 2-θ.

4. The crystalline form according to claim 3, wherein the x-ray powder diffraction pattern comprises one or more additional peaks selected from peaks at about 13.5°±0.2°, 14.6°±0.2°, 16.0°±0.2°, 17.5°±0.2°, 18.8°±0.2°, 20.2°±0.2°, 20.7°±0.2°, 23.0°±0.2°, 24.6°±0.2°, 26.3°±0.2° and 26.8°±0.2° 2-θ.

5. A pharmaceutical composition comprising the crystalline form of claim 1 and a pharmaceutically acceptable carrier or excipient.

6. A method for inhibiting MCL-1 in a patient comprising administering to the patient the crystalline form of claim 1.

* * * * *